United States Patent
Stoller et al.

(10) Patent No.: US 6,268,308 B1
(45) Date of Patent: Jul. 31, 2001

(54) HERBICIDAL S-SUBSTITUTED 1,2,4,6-THIATRIAZINES

(75) Inventors: André Stoller, Blotzheim (FR); Walter Kunz, Oberwil (CH); Helmut Zondler, Bottmingen (CH); Christoph Lüthy, Münchenstein (CH); Jean Wenger, Wallbach (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/242,596

(22) PCT Filed: Aug. 25, 1997

(86) PCT No.: PCT/EP97/04627

§ 371 Date: Dec. 17, 1999

§ 102(e) Date: Dec. 17, 1999

(87) PCT Pub. No.: WO98/08845

PCT Pub. Date: Mar. 5, 1998

(30) Foreign Application Priority Data

Aug. 27, 1996 (CH) .................................................. 2106/96

(51) Int. Cl.⁷ .......................... A01N 43/72; C07D 417/04
(52) U.S. Cl. ............................................... 504/222; 544/7
(58) Field of Search .................................. 544/7; 504/222

(56) References Cited

FOREIGN PATENT DOCUMENTS

| 113 006 | 5/1975 | (DE) . |
| WO 96/01814 | 1/1996 | (WO) . |

OTHER PUBLICATIONS

Chem. Ber. 121, pp. 383–388 (1988) (contains English abstract).
Z. Naturforsch. 43, pp. 763–768 (1988) (contains English abstract).
Chem. Ber. 126, pp. 2601–2607 (1993) (contains English abstract).
J. Am. Chem. Soc. 1989, 111, pp. 1180–1185.
Derwent Abstract 46231W/28 (1975) (abstract of DE 113006).
$1\lambda^4$–UND $1\lambda^6$.2.4.6"Thiatriazine aus Sulfodiimiden" Dissertation of Winfried Jürgler, 1988, Philipps–Universität, Marburg/Lanh, Germany (Chem. Abstract 109:230962, 1988).
Chem. Ber. 124, pp. 1347–1352 (1991) (contains English abstract).
Z. Chem. 16, pp. 358–359 (1976) (describes preparation of compounds of formula II, see p. 358, right col., compound 2) (Chem. Abstract 86:89774, 1977).
Chem. Rev. vol. 90, No. 6, pp. 879–933 (1990).
J. Chem. Soc. Perkin I Trans., pp. 887–893 (1977).
Synthesis, pp. 583–585 (1996).
J. Org. Chem. 49, pp. 5250–5253 (1984).
Chem. Abstract 109:230962 (1988).
Chem. Abstract 86:89774 (1977).

*Primary Examiner*—Richard L. Raymond
*Assistant Examiner*—Venkataraman Balasubramanian
(74) *Attorney, Agent, or Firm*—William A. Teoli, Jr.

(57) ABSTRACT

Compounds of formula (I) in which $Q_i$ is an unsaturated five-membered optionally substituted or condensed heterocyclic ring and X is O, S, SO or SO2, and agronomically tolerated salts/N-oxides/isomers/enantiomers of these compounds are suitable as herbicides

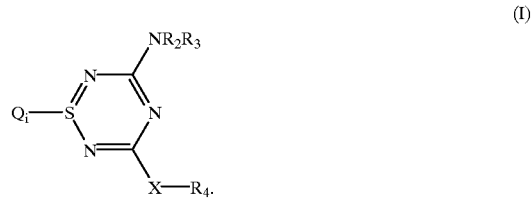

(I)

6 Claims, No Drawings

HERBICIDAL S-SUBSTITUTED 1,2,4,6-THIATRIAZINES

The present invention relates to novel herbicidally active thiatriazine derivatives, processes for their preparaiton, compositions which comprise these compounds, and their use for controlling weeds, in particular in crops of useful plants, or for inhibiting plant growth.

Thiatriazine compounds are described, for example in Chem. Ber. 121, 383–386 (1988), Z. Naturforsch. 43, 763–768 (1988), Chem. Ber. 126, 2601–2607 (1993), J. Am. Chem. Soc. 1989, 111, 1180–1185, DD 113 006 and in WO 96/01814. Novel thiatriazine derivatives having herbicidal and growth-inhibiting properties have now been found.

The present invention thus relates to compounds of the formula I in which $Q_i$ is the group Q16 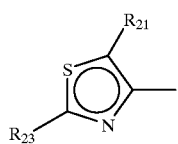
Q17 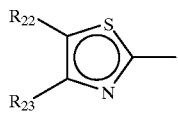
Q18 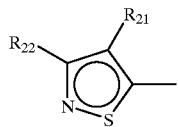
Q19 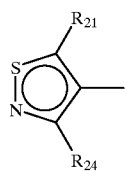
Q20 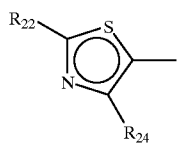
Q21 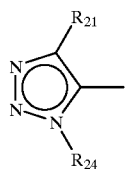
Q22 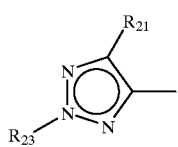
Q23 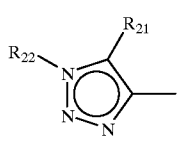
Q24 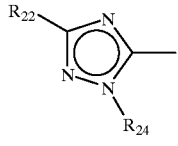
Q25 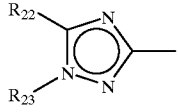
Q26 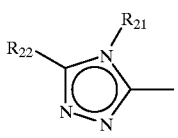
Q27 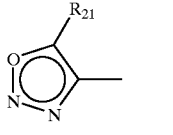
Q28 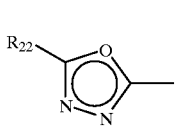
Q29 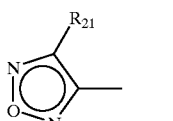
Q30 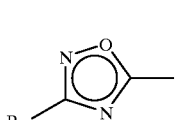
Q31 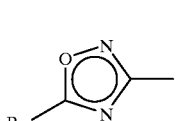
Q32 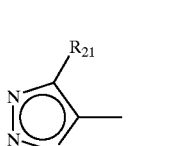
Q33 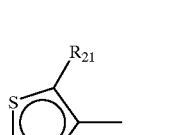
Q34 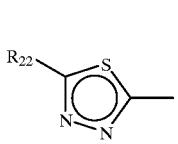
Q35 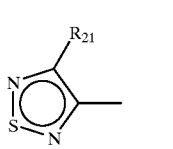
Q36 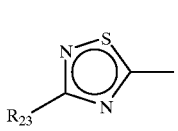

-continued

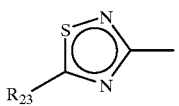
Q37

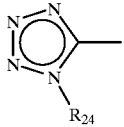
Q38

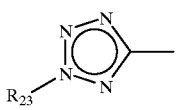
Q39

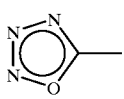
Q40

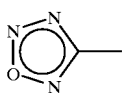
Q41

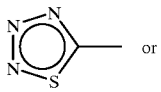
Q42

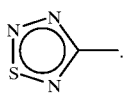
Q43 or

Q44

$R_2$ and $R_3$ independently of one another are hydrogen, $C_1$–$C_6$alkyl or $C_1$–$C_6$alkyl substituted by $S(O)_nR_6$, halogen, cyano, nitro, $C_1$–$C_8$alkoxy, $C_3$–$C_6$trialkylsilyl, hydroxyl, amino, ammonium, tri-$C_1$–$C_4$alkylammonium, —COOH, —COOM, in which M is ammonium or an alkali metal or alkaline earth metal atom, $C_3$–$C_8$cycloalkyl, $C_1$–$C_5$alkylcarbonyloxy, phenylcarbonyloxy, naphthylcarbonyloxy, $C_1$–$C_6$alkylamino, $C_1$–$C_5$alkylcarbonyl, $C_2$–$C_{12}$dialkylamino, phenyl, naphthyl, phenoxy, naphthoxy, biphenyl, biphenyloxy, phenthio or naphthio, it being possible for the aromatic rings mentioned to be substituted by halogen, cyano, nitro, —$OR_5$, —$NR_{10}R_{11}$, $C_1$–$C_4$alkyl, formyl, $C_1$–$C_4$alkylcarbonyl, $COOR_7$, $C_1$–$C_4$alkylthio, $C_1$–$C_4$alkylsulfonyl or —$CONR_8R_9$, or $R_2$ and $R_3$ independently of one another are $C_2$–$C_6$alkenyl or $C_2$–$C_6$alkenyl substituted by halogen, cyano, nitro, $C_1$–$C_8$alkoxy, $C_3$–$C_6$trialkylsilyl, hydroxyl, amino, ammonium, tri-$C_1$–$C_4$alkylammonium, —COOH, —COOM, in which M is ammonium or an alkali metal or alkaline earth metal atom, $C_3$–$C_8$cycloalkyl, $C_2$–$C_5$alkylcarbonyloxy, phenylcarbonyloxy, naphthylcarbonyloxy, $C_1$–$C_6$alkylamino, $C_2$–$C_5$alkoxycarbonyl, $C_2$–$C_2$dialkylamino, phenyl, naphthyl, phenoxy, naphthoxy, biphenyl, biphenyloxy, phenthio or naphthio, it being possible for the aromatic rings mentioned to be substituted by halogen, cyano, nitro, —$OR_5$, —$NR_{10}R_{11}$, $C_1$–$C_4$alkyl, formyl, $C_1$–$C_4$alkylcarbonyl, $COOR_7$, $C_1$–$C_4$alkylthio, $C_1$–$C_4$alkylsulfonyl or —$CONR_8R_9$, or $R_2$ and $R_3$ independently of one another are $C_3$–$C_6$alkynyl or $C_3$–$C_6$alkynyl substituted by halogen, cyano, nitro, $C_1$–$C_8$alkoxy, $C_3$–$C_6$trialkylsilyl, hydroxyl, amino, ammonium, tri-$C_1$–$C_4$alkylammonium, —COOH, —COOM, in which M is ammonium or an alkali metal or alkaline earth metal atom, $C_3$–$C_8$cycloalkyl, $C_1$–$C_5$alkylcarbonyloxy, phenylcarbonyloxy, naphthylcarbonyloxy, $C_1$–$C_6$alkylamino, $C_1$–$C_5$alkoxycarbonyl, $C_2$–$C_{12}$dialkylamino, phenyl, naphthyl, phenoxy, naphthoxy, biphenyl, biphenyloxy, phenthio or naphthio, it being possible for the aromatic rings mentioned to be substituted by halogen, cyano, nitro, —$OR_5$, —$NR_{10}R_{11}$, $C_1$–$C_4$alkyl, formyl, $C_1$–$C_4$alkylcarbonyl, $COOR_7$, $C_1$–$C_4$alkylthio, $C_1$–$C_4$alkylsulfonyl or —$CONR_8R_9$, or $R_2$ and $R_3$ independently of one another are formyl, $C_1$–$C_{15}$alkylcarbonyl, $C_2$–$C_{15}$alkenylcarbonyl, $C_4$–$C_9$cycloalkylcarbonyl, $C_6$–$C_9$cycloalkenylcarbonyl or $C_3$–$C_8$cycloalkyl-$C_1$–$C_6$alkylcarbonyl, it being possible for these substituents to be substituted by halogen, cyano, nitro, hydroxyl, amino, $C_1$–$C_6$alkylamino, $C_2$–$C_{12}$dialkylamino, —COOH, —COOM, in which M is ammonium or an alkali metal or alkaline earth metal atom, $C_1$–$C_8$alkoxycarbonyl, $C_4$–$C_{10}$cycloalkoxycarbonyl, $C_1$–$C_8$alkylaminocarbonyl or $C_2$–$C_{12}$dialkylaminocarbonyl, or $R_2$ and $R_3$ independently of one another are heterocyclyl, heterocyclylcarbonyl, heterocyclyl substituted by halogen, cyano, nitro, $C_1$–$C_5$alkyl, $C_1$–$C_5$alkoxy, $C_1$–$C_5$alkylcarbonyl, $C_1$–$C_5$alkylcarbonyloxy, $C_1$–$C_6$alkoxycarbonyl, aminocarbonyl, $C_1$–$C_6$alkylaminocarbonyl or $C_2$–$C_{11}$dialkylaminocarbonyl, or heterocyclylcarbonyl substituted by halogen, cyano, nitro, $C_1$–$C_5$alkyl, $C_1$–$C_5$alkoxy, $C_1$–$C_5$alkylcarbonyl, $C_1$–$C_6$alkoxycarbonyl, aminocarbonyl, $C_1$–$C_6$alkylamino or $C_1$–$C_5$alkylcarbonyloxy, or $R_2$ and $R_3$ independently of one another are phenylcarbonyl, biphenylcarbonyl, naphthylcarbonyl, phenyl-$C_1$–$C_6$alkylcarbonyl, biphenyl-$C_1$–$C_6$alkylcarbonyl, naphthyl-$C_1$–$C_6$alkylcarbonyl, phenyl-$C_2$–$C_6$alkenylcarbonyl, biphenyl-$C_2$–$C_6$alkenylcarbonyl, naphthyl-$C_2$–$C_6$alkenylcarbonyl, phenyl-$C_3$–$C_6$alkynylcarbonyl, biphenyl-$C_3$–$C_6$alkynylcarbonyl or naphthyl-$C_3$–$C_6$alkynylcarbonyl, it being possible for these substituents to be substituted by $C_1$–$C_5$alkyl, $C_1$–$C_5$alkoxy, $C_1$–$C_5$alkylthio, $C_1$–$C_5$halogenoalkyl, $C_1$–$C_5$alkylcarbonyl, halogen, cyano, amino, nitro, —$COOR_7$, $C_1$–$C_8$alkoxycarbonyl, hydroxyl, $C_1$–$C_5$alkylsulfinyl, $C_1$–$C_5$alkylsulfonyl, $C_1$–$C_6$alkylaminocarbonyl or $C_2$–$C_{12}$dialkylaminocarbonyl, or $R_2$ and $R_3$ independently of one another are phenyl or naphthyl, it being possible for there substituents to be substituted by halogen, cyano, nitro, $C_1$–$C_5$alkyl, $C_1$–$C_5$alkoxy, $C_1$–$C_5$alkylthio, —COOH, —$CONH_2$, $C_1$–$C_6$alkylaminocarbonyl, $C_2$–$C_{10}$dialkylaminocarbonyl, $C_1$–$C_5$alkylcarbonyl or $C_1$–$C_5$alkoxycarbonyl, or $R_2$ and $R_3$, together with the nitrogen atom to which they are bonded, form a heterocyclic ring, which can be substituted by $C_1$–$C_5$alkyl, $C_1$–$C_5$alkoxy, halogen, cyano or nitro, or $R_2$ and $R_3$ independently of one another are amino, $C_1$–$C_6$alkylamino, $C_2$–$C_8$dialkylamino, phenylamino, naphthylamino, $C_1$–$C_6$alkylcarbonylamino, $C_1$–$C_{10}$alkoxycarbonylamino, hydroxyl, $C_1$–$C_6$alkoxy, $C_1$–$C_6$alkylcarbonyloxy, phenoxy, biphenyloxy or naphthoxy, X is oxygen or $S(O)_x$, in which x is the number 0, 1 or 2, and $R_4$ is $C_1$–$C_8$alkyl, $C_2$–$C_8$alkenyl, $C_3$–$C_8$alkynyl, $C_3$–$C_8$cycloalkyl, $C_5$–$C_8$cycloalkenyl, $C_3$–$C_8$cycloalkyl-$C_1$–$C_4$alkyl or $C_1$–$C_4$alkyl-$C_3$–$C_8$cycloalkyl, it being possible for these substituents to be substituted by halogen, cyano, nitro, =O or —$OR_5$, or $R_4$ is phenyl, biphenyl, naphthyl, heterocyclyl, $C_1$–$C_4$alkylphenyl, $C_1$–$C_4$alkylnaphthyl, phenyl-$C_1$–$C_4$alkyl or naphthyl-$C_1$–$C_4$alkyl, it being possible for these substituents to be substituted by halogen, cyano, nitro, amino, —COOH, hydroxyl, $C_1$–$C_{10}$alkyl, $C_1$–$C_{10}$alkyloxy, $C_1$–$C_6$alkylamino, di-$C_2$–$C_8$alkylamino, $C_1$–$C_{10}$alkylthio, $C_1$–$C_{10}$halogenoalkyl, $C_1$–$C_{10}$halogenoalkoxy, $C_1$–$C_{10}$halogenoalkylthio, $C_2$–$C_{10}$alkoxycarbonylalkoxy, $C_1$–$C_6$alkylsulfinyl, $C_1$–$C_6$alkylsulfonyl, $C_1$–$C_6$alkyloxycarbonyl, $C_1$–$C_6$alkylcarbonyl, —$CONH_2$, formyl, $C_1$–$C_7$alkylaminocarbonyl, $C_2$–$C_{11}$dialkylaminocarbonyl, $C_3$–$C_6$trialkylsilyl, $C_1$–$C_{10}$alkylcarbonylamino, $C_1$–$C_{10}$alkylcarbonyloxy, phenoxy, halophenoxy, pyridyloxy or by pyridyloxy substituted by halogen, $C_1$–$C_4$alkyl, $C_1$–$C_4$alkoxy, cyano, nitro or amino, or two substituents adjacent to each other on the phenyl or naphthyl ring $R_4$ form a carbocyclic or heterocyclic ring, which can be substituted by halogen, cyano, nitro, amino, —COOH, oxo, $C_1$–$C_{10}$alkyl, $C_1$–$C_{10}$alkoxy, $C_1$–$C_{10}$alkylthio, $C_1$–$C_{10}$halogenoalkyl, hydroxyl, $C_3$–$C_{10}$alkoxycarbonylalkoxy, $C_1$–$C_6$alkylsulfinyl, $C_1$–$C_6$alkylsulfonyl, $C_2$–$C_6$alkyloxycarbonyl, $C_2$–$C_6$alkylcarbonyl, —$CONH_2$, formyl, $C_2$–$C_7$alkylaminocarbonyl, $C_3$–$C_{11}$dialkylaminocarbonyl, $C_3$–$C_6$trialkylsilyl, $C_2$–$C_{10}$alkylcarbonylamino, $C_2$–$C_{10}$alkylcarbonyloxy, phenoxy, pyridyloxy or by pyridyloxy substituted by halogen, $C_1$–$C_4$alkyl, $C_1$–$C_4$alkoxy, cyano, nitro or amino, $R_5$ is hydrogen, $C_1$–$C_6$alkyl, $C_1$–$C_6$halogenoalkyl, $C_2$–$C_5$alkoxyalkyl, $C_1$–$C_6$cyanoalkyl, phenyl, phenyl-$C_1$–$C_4$alkyl, formyl, $C_2$–$C_7$alkylcarbonyl, $C_2$–$C_7$alkoxycarbonyl, $C_1$–$C_6$alkylaminocarbonyl, $C_2$–$C_8$dialkylaminocarbonyl, benzoyl, halogenobenzoyl, $C_1$–$C_6$alkylamino, $C_2$–$C_8$dialkylamino, —$N=CH_2$, —N=CH—$C_1$–$C_4$alkyl, —N=C($C_1$–$C_4$alkyl)$_2$, tri($C_1$–$C_4$alkyl)silyl, $C_3$–$C_7$cycloalkyl, $C_2$–$C_7$alkenyl, $C_3$–$C_7$alkynyl or heterocyclyl, n is the number 0, 1 or 2, $R_6$ is hydrogen or cyano, if n is the number 0, or $R_6$ is $C_1$–$C_5$alkyl, $C_2$–$C_5$alkenyl, $C_3$–$C_5$alkynyl, $C_1$–$C_6$alkoxyalkyl, $C_1$–$C_5$halogenalkyl, $C_1$–$C_5$hydroxyalkyl, phenyl, phenyl-$C_1$–$C_4$alkyl, heterocyclyl, heterocyclyl-$C_1$–$C_4$alkyl or $C_3$–$C_7$cycloalkyl, $R_7$ is hydrogen, $C_1$–$C_{12}$alkyl, $C_1$–$C_{12}$halogenoalkyl, $C_1$–$C_6$nitroalkyl, $C_1$–$C_6$cyanoalkyl, phenyl, $C_2$–$C_{10}$alkoxyalkyl, $C_2$–$C_{10}$alkylcarbonylalkyl, $C_2$–$C_{10}$alkoxycarbonylalkyl, heterocyclyl, $C_3$–$C_7$cycloalkyl, $C_1$–$C_7$halogenocycloalkyl, —$N=CH_2$, —N=CH—$C_1$–$C_4$alkyl, —N=C($C_1$–$C_4$alkyl)$_2$ or $C_2$–$C_6$dialkylamino, $R_8$ and $R_9$ independently of one another are hydrogen, phenyl, $C_1$–$C_8$alkyl, $C_1$–$C_8$halogenoalkyl, $C_1$–$C_8$alkoxy, phenoxy, $C_2$–$C_7$cyanoalkyl, $C_3$–$C_7$alkenyl, $C_3$–$C_7$alkynyl, $C_2$–$C_8$alkoxyalkyl, $C_1$–$C_6$alkylamino or $C_2$–$C_6$dialkylamino, or $R_8$ and $R_9$, together with the nitrogen atom to which they are bonded, form a three- to seven-membered heterocyclic radical, which can contain one or two further heteroatoms and can in turn be substituted by $C_{1-6}$ alkyl groups or halogen, $R_{10}$ and $R_{11}$ independently of one another are hydrogen, phenyl, $C_1$–$C_8$alkyl, $C_1$–$C_8$haloalkyl, $C_1$–$C_8$alkoxy, phenoxy, $C_2$–$C_7$cyanoalkyl, $C_3$–$C_7$alkenyl, $C_3$–$C_7$alkynyl, $C_2$–$C_8$alkoxyalkyl, $C_1$–$C_6$alkylamino, ($C_1$–$C_6$alkylamino)-carbonyl, $C_2$–$C_6$dialkylamino, ($C_2$–$C_2$–$C_6$dialkylamino)-carbonyl, formyl, ($C_1$–$C_7$alkyl)-carbonyl, ($C_1$–$C_6$alkoxy)-carbonyl, phenylcarbonyl, phenoxycarbonyl, benzyloxycarbonyl, heterocyclylcarbonyl or heterocyclyloxycarbonyl, or $R_{10}$ and $R_{11}$, together with the nitrogen atom to which they are bonded, form a three- to seven-membered heterocyclic radical, which can contain one or two further heteroatoms and can in turn be substituted by $C_{1-6}$ alkyl groups or halogen, $R_{12}$ is $C_1$–$C_8$alkyl, $C_1$–$C_8$alkoxy, $C_1$–$C_8$alkenyloxy, $C_1$–$C_8$alkynyloxy, $C_1$–$C_8$halogenoalkyl, phenyl, phenyloxy, phenyl-$C_1$–$C_4$alkyloxy, $C_3$–$C_8$alkoxycarbonylalkyloxy or $C_3$–$C_8$alkylcarbonylalkyloxy, $R_{13}$ and $R_{14}$ independently of one another are hydrogen, $C_1$–$C_6$alkyl, $C_2$–$C_6$alkylcarbonyl or phenyl, $R_{21}$, $R_{22}$, $R_{23}$ and $R_{24}$ independently of one another are $C_1$–$C_{10}$alkyl, $C_3$–$C_6$cycloalkyl, $C_3$–$C_6$cycloalkyl-$C_1$–$C_4$alkyl, $C_1$–$C_{alkyl-C3}$–$C_6$cycloalkyl, $C_2$–$C_{10}$alkenyl, $C_3$–$C_6$cycloalkyl-$C_2$–$C_4$alkenyl, $C_2$–$C_6$alkenyl-$C_3$–$C_6$cycloalkyl, $C_2$–$C_{10}$alkynyl, $C_3$–$C_6$cycloalkyl-$C_2$–$C_4$alkynyl, $C_2$–$C_6$alkynyl-$C_3$–$C_6$cycloalkyl, $C_5$–$C_6$cycloalkenyl, $C_5$–$C_6$cycloalkenyl-$C_1$–$C_4$alkyl, $C_1$–$C_6$alkyl-$C_5$–$C_6$cycloalkenyl, $C_5$–$C_6$cycloalkenyl-$C_2$–$C_4$alkenyl, $C_2$–$C_6$alkenyl-$C_5$–$C_6$cycloalkenyl, $C_5$–$C_6$cycloalkenyl-$C_2$–$C_4$alkynyl, $C_2$–$C_6$alkynyl-$C_5$–$C_6$cycloalkenyl, $C_3$–$C_6$cycloalkyl-$C_3$–$C_6$cycloalkyl, $C_5$–$C_6$cycloalkenyl-$C_3$–$C_6$cycloalkyl, $C_5$–$C_6$cycloalkenyl-$C_3$–$C_6$cycloalkyl, $C_5$–$C_6$cycloalkenyl-$C_5$–$C_6$cycloalkenyl, $C_3$–$C_6$cycloalkyl, $C_2$–$C_8$alkynyl-$C_2$–$C_8$alkenyl, $C_2$–$C_8$alkenyl-$C_2$–$C_8$alkynyl, phenyl, phenyl-$C_1$–$C_4$alkyl, phenyl-$C_2$–$C_4$alkenyl, phenyl-$C_2$–$C_4$alkynyl, heterocyclyl, heterocyclyl-$C_1$–$C_4$alkyl, heterocyclyl-$C_1$–$C_4$alkenyl or heterocyclyl-$C_1$–$C_4$alkynyl, it being possible for these groups in turn to be substituted independently of one another by halogen, cyano, azido, nitro, —$OR_5$, oxo, —$S(O)_nR_6$, —$COOR_7$, —$CONR_8R_9$, —$NR_{10}R_{11}$, =$NR_{12}$ or =N—$NR_{13}R_{14}$, or $R_{21}$, $R_{22}$, $R_{23}$ and $R_{24}$ independently of one another are hydrogen, halogen, cyano, azido, nitro, —$OR_5$, —S(O)$_n$R$_6$, —COOR$_7$, —CONR$_8$R$_9$, —NR$_{10}$R$_{11}$, tri(C$_1$–C$_4$-alkyl)-silyl, tri(C$_1$–C$_4$-alkyl)-stannyl, tri(C$_1$–C$_4$-alkyl)-silyl-C$_1$–C$_4$alkyl, tri(C$_1$–C$_4$alkyl)-stannyl-C$_1$–C$_4$-alkyl, tri(C$_1$–C$_4$-alkyl)-silyl-C$_2$–C$_4$alkenyl, tri(C$_1$–C$_4$alkyl)-stannyl-C$_2$–C$_4$alkenyl, tri(C$_1$–C$_4$alkyl)-silyl-C$_2$–C$_4$alkynyl, tri(C$_1$–C$_4$alkyl)-stannyl-C$_2$–C$_4$alkynyl, —B(OH)$_2$ or —B(C$_1$–C$_4$alkoxy)$_2$, it being possible for in each case two adjacent substituents R$_{21}$, R$_{22}$, R$_{23}$ and R$_{24}$ to form a five- to eight-membered ring with the two ring atoms to which they are bonded, it being possible for this ring system to be aromatic or partly saturated, carbocyclic or heterocyclic and furthermore to be substituted by halogen, cyano, azido, nitro, —OR$_5$, =O, —S(O)$_n$R$_6$, —COOR$_7$, —CONR$_8$R$_9$, —NR$_{10}$R$_{11}$, =NR$_{12}$ or =N—NR$_{13}$R$_{14}$, and agronomically tolerated salts/N-oxides/isomers/enantiomers of these compounds.

The alkyl groups which occur in the substituent definitions can be straight-chain or branched and are, for example, methyl, ethyl, propyl, butyl, pentyl, hexyl, heptyl, octyl, nonyl, decyl, undecyl, dodecyl, tetradecyl, hexadecyl, octadecyl or eicosyl, and branched isomers thereof. Alkoxy, alkenyl and alkynyl radicals are derived from the alkyl groups mentioned. The alkenyl and alkynyl groups can be mono- or polyunsaturated.

Suitable cycloalkyl substituents contain 3 to 8 carbon atoms and are, for example, cyclopropyl, cyclobutyl, cyclopentyl, cyclohexyl, cycloheptyl or cyclooctyl. Corresponding cycloalkenyl substituents can be mono- or also polyunsaturated, for example cyclopentadienyl or cyclooctatetraenyl.

If alkyl, alkenyl or alkynyl occur as substituents on a cycloalkyl, cycloalkenyl, phenyl, biphenyl, naphthyl or heterocyclyl, these ring systems can also be polysubstituted by alkyl, alkenyl or alkynyl.

Halogen is as a rule fluorine, chlorine, bromine or iodine. The same also applies to halogen in combination with other definitions, such as halogenoalkyl or halogenophenyl.

Phenyl can be unsubstituted or substituted by halogen, cyano, nitro, —OR$_5$, —NR$_{10}$R$_{11}$, C$_1$–C$_4$alkyl, C$_1$–C$_4$halogenoalkyl, formyl, C$_1$–C$_4$alkylcarbonyl, COOR$_7$, C$_1$–C$_4$alkylthio, C$_1$–C$_4$alkylsulfonyl or —CONR$_8$R$_9$.

Carbocyclic radicals which are formed by two adjacent substituents R$_{21}$, R$_{22}$, R$_{23}$ and R$_{24}$ and the two ring atoms to which they are bonded are, for example, benzene, where the group Q$_i$ can be, for example, indol-2-yl

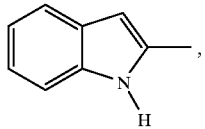

or 1H-indazol-3-yl

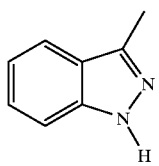

or cyclohexene, where the group Q$_i$ can be, for example, 4,5,6,7-tetrahydro-benzo[b]thien-2-yl

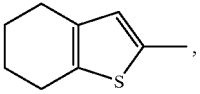

or cyclooctane, where the group Q$_i$ can be, for example, 4,5,6,7,8,9-hexahydrocycloocta[c]isothiazol-3-yl

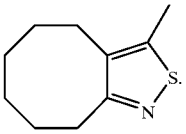

Heterocyclyl is to be understood as meaning ring systems which, in addition to carbon atoms, contain at least one heteroatom, such as nitrogen, oxygen and/or sulfur. They can be saturated or unsaturated. Such ring systems preferably contain 3 to 8 ring atoms. This also applies to those heterocyclic radicals which, in the case of groups such as —NR$_{10}$R$_{11}$, are formed by two substituents bonded to a nitrogen atom.

Heterocyclyl ring systems in the context of the present invention can also be substituted. Suitable substituents are, for example, C$_1$–C$_4$alkyl, C$_1$–C$_4$halogenoalkyl, C$_1$–C$_4$alkoxy, cyano, nitro or C$_3$–C$_6$cycloalkyl.

Heterocyclyl as a substituent of a group Q$_i$ can be, for example, epoxidyl, dioxolanyl, pyrrolidinyl, piperidinyl, morpholinyl, pyridyl, pyrrolyl, furyl, thienyl, imidazolyl, tetrahydrofuryl, tetrahydropyranyl, dihydrofuryl, dihydropyranyl, isoxazolyl, oxazolyl, thiazolyl, oxazolinyl (for example:

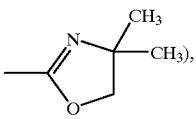

oxazolidinyl, imidazolinyl, imidazolidinyl or dioxanyl.

Heterocyclic radicals which are formed by two adjacent substituents R$_{21}$, R$_{22}$, R$_{23}$ and R$_{24}$ and the two ring atoms to which they are bonded are, for example, pyridine, where the group Q$_i$ can be, for example, thieno[3,2-b]pyridin-2-yl

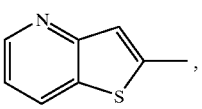

or pyrimidine, where the group Q$_i$ can be, for example, thieno[2,3-d]pyrimidin-6-yl

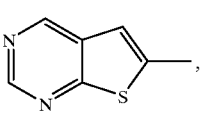

or dihydrothiophene, where the group Q$_i$ can be, for example, thieno[2,3-c]isothiazol-3yl

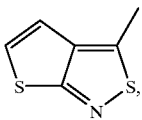

or tetrahydrofuran, where the group $Q_i$ can be, for example, 2,6-dihydro-4H-furo[3,4-c]pyrazol-3yl

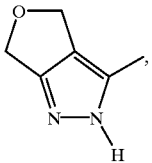

or thiophene, where the group $Q_i$ can be, for example, thieno[3,2-b]thiophen-2-yl

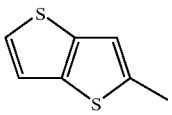

where these examples do not represent a restriction to the invention.

Heterocyclic radicals $R_6$ are preferably, inter alia, pyridyl, pyrimidinyl and triazinyl.

Preferred heterocyclic radicals $R_7$ are, for example, oxetanyl, pyridyl, thienyl and furyl.

$R_8$ and $R_9$ preferably form rings, such as piperidinyl, morpholinyl and pyrrolidinyl.

Preferred examples of heterocyclic radicals formed by $R_{10}$ and $R_{11}$ or $R_2$ and $R_3$ with the nitrogen atom to which the substituents are bonded are piperidinyl, morpholinyl, pyrrolidinyl, triazolyl, tetrazolyl and imidazolyl.

Heterocyclic radicals $R_9$ are preferably thienyl, furyl, pyridyl and oxetanyl.

Phenyl and naphthyl rings $R_4$ can be substituted by carbo or heterocyclic radicals which are formed by 2 substituents adjacent to one another on these phenyl or naphthyl rings. The carbocyclic radicals preferably contain 4 to 6 carbon atoms, such as cyclobutyl, cyclopentyl and cyclohexyl. Heterocyclic groups are, in particular, dioxolanyl and tetrahydrofuryl.

Heterocyclic radicals $R_4$ such as succinimidyl, pyridyl, thienyl or furyl, can contain fused-on carbocyclic radicals, such as phenyl or cyclohexenyl.

Heterocyclic radicals $R_2$ and $R_3$ are preferably pyridyl, pyrrolyl and pyrimidinyl.

Heterocyclic radicals formed from $-NR_2R_3$ include, for example, succinimidyl, imidazolyl and triazolyl, it being possible for such groups to contain fused-on carbocyclic radicals, such as phenyl or cyclohexene.

Heterocyclylcarbonyl $R_2$ or $R_3$ is, for example, pyridyl, pyrrolidinyl, triazolyl, thienyl, furyl or isoxazolyl.

In substituents such as $-N=C(C_1-C_4alkyl)_2$, the alkyl groups can be identical or different. They preferably have the same meaning. The same also applies to the alkyl groups in dialkylamino, dialkylaminocarbonyl, trialkylammonium and trialkylsilyl substituents.

Alkali metals and alkaline earth metals are, for example, lithium, sodium, potassium, magnesium, calcium or barium.

The invention also relates to the salts which the compounds of the formula I can form, in particular, with amines, alkali metal and alkaline earth metal bases or quaternary ammonium bases.

The alkali metal and alkaline earth metal hydroxides as salt-forming agents include the hydroxides of lithium, sodium, potassium, magnesium or calcium, but in particular those of sodium or potassium.

Examples of amines which are suitable for ammonium salt formation are both ammonia and primary, secondary and tertiary $C_1-C_{18}$alkylamines, $C_1-C_4$hydroxyalkylamines and $C_2-C_4$alkoxyalkylamines, for example methylamine, ethylamine, n-propylamine, isopropylamine, the four isomeric butylamines, n-amylamine, iso-amylamine, hexylamine, heptylamine, octylamine, nonylamine, decylamine, pentadecylamine, hexadecylamine, heptadecylamine, octadecylamine, methyl-ethylamine, methyl-iso-propylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, di-iso-propylamine, di-n-butylamine, di-n-amylamine, di-iso-amylamine, dihexylamine, diheptylamine, dioctylamine, ethanolamine, n-propanolamine, iso-propanolamine, N,N-diethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine, propylenediamine, trimethylamine, triethylamine, tri-n-propylamine, tri-iso-propylamine, tri-n-butylamine, tri-iso-butylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; and primary arylamines, for example anilines, methoxyanilines, ethoxyanilines, o-, m- and p-toluidines, phenylenediamines, benzidines, naphthylamines and o-, m- and p-chloroanilines; but in particular triethylamine, iso-propylamine and di-iso-propylamine.

The compounds of the formula I contain a centre of asymmetry in the sulfur atom of the thiatriazine ring. Racemates, which can be separated into the corresponding enantiomers by customary separation processes, are therefore formed during preparation of these compounds. If further centres of asymmetry are present in the substituents of the thiatriazine ring, the corresponding diastereoisomers can also be separated in the customary manner. The present invention also relates to such diastereoisomers and enantiomers.

In preferred compounds of the formula I, $Q_i$ is the group $Q_1$, $Q_2$, $Q_3$, $Q_4$, $Q_5$, $Q_7$, $Q_8$, $Q_{11}$, $Q_{13}$, $Q_{16}$, $Q_{17}$, $Q_{18}$, $Q_{19}$, $Q_{20}$, $Q_{21}$, $Q_{30}$, $Q_{33}$, $Q_{36}$, $Q_{39}$ or $Q_{40}$.

Compounds of the formula I which are furthermore preferred are those in which $R_{21}$, $R_{22}$, $R_{23}$ and $R_{24}$ independently of one another are $C_1-C_{10}$alkyl, $C_3-C_6$cycloalkyl, $C_2-C_{10}$alkenyl, $C_2-C_{10}$alkynyl, $C_5-C_6$cycloalkenyl, $C_2-C_8$alkynyl-$C_2-C_8$alkenyl or $C_2-C_8$alkynyl, phenyl, phenyl-$C_1-C_4$alkyl, phenyl-$C_2-C_4$alkenyl, phenyl-$C_2-C_4$alkynyl, heterocyclyl, heterocyclyl-$C_1-C_4$alkyl, heterocyclyl-$C_2-C_4$alkenyl or heterocyclyl-$C_2-C_4$alkynyl, it being possible for these groups in turn to be substituted indepently of one another by halogen, cyano, $-OR_5$, $=O$, $-S(O)_nR_6$, $-COOR_7$, $-CONR_8R_9$ or $-NR_{10}R_{11}$, or $R_{21}$, $R_{22}$, $R_{23}$ and $R_{24}$ independently of one another are halogen, cyano, tri($C_1-C_4$alkyl)-silyl, tri($C_1-C_4$alkyl)-silyl-$C_1-C_4$alkyl, tri($C_1-C_4$alkyl)-silyl-$C_2-C_4$alkenyl, tri($C_1-C_4$alkyl)-silyl-$C_2-C_4$alkynyl, $-OR_5$, $-S(O)_nR_6$, $-COOR_7$, $-CONR_8R_9$ or $-NR_{10}R_{11}$, it being possible for in each case two substituents $R_{21}$, $R_{22}$, $R_{23}$ and $R_{24}$ which are adjacent to form a five- to six-membered ring with the two ring atoms to which they are bonded, it being possible for this ring system to be aromatic or partly saturated, carbocyclic or heterocyclic and optionally substituted by halogen, cyano, —$OR_5$, =O, —$S(O)_nR_6$, —$COOR_7$, —$CONR_8R_9$ or —$NR_{10}R_{11}$, $R_5$ is hydrogen, $C_1$–$C_6$alkyl, $C_1$–$C_6$halogenoalkyl, $C_2$–$C_5$alkoxyalkyl, phenyl, phenyl-$C_1$–$C_4$alkyl, $C_2$–$C_7$alkylcarbonyl, $C_1$–$C_6$alkylaminocarbonyl, $C_2$–$C_8$dialkylaminocarbonyl, tri($C_1$–$C_4$alkyl)-silyl, $C_2$–$C_7$alkenyl or $C_3$–$C_7$alkynyl or heterocyclyl, $R_6$ is hydrogen, if n is the number 0, or $R_6$ is $C_1$–$C_5$alkyl, phenyl, phenyl-$C_1$–$C_4$alkyl or heterocyclyl, $R_7$ is hydrogen, $C_1$–$C_6$alkyl, $C_1$–$C_6$halogenoalkyl, $C_1$–$C_6$cyanoalkyl, $C_2$–$C_{10}$alkoxycarbonylalkyl, heterocyclyl, $C_3$–$C_6$cycloalkyl or $C_2$–$C_6$dialkylamino, $R_8$ and $R_9$ independently of one another are hydrogen or $C_1$–$C_8$alkyl, or $R_8$ and $R_9$, together with the nitrogen atom to which they are bonded, form a three- to seven-membered heterocyclic radical, which can contain one or two further heteroatoms and can be substituted by $C_{1-6}$ alkyl groups, $R_{10}$ and $R_{11}$ independently of one another are hydrogen, phenyl, $C_1$–$C_8$alkyl, $C_3$–$C_7$alkenyl, ($C_1$–$C_6$alkylamino)-carbonyl, ($C_2$–$C_6$dialkylamino)-carbonyl, ($C_1$–$C_7$alkyl)-carbonyl, ($C_1$–$C_6$alkoxy)-carbonyl or heterocyclylcarbonyl, or $R_{10}$ and $R_{11}$, together with the nitrogen atom to which they are bonded, form a three to seven-membered heterocyclic radical, which can contain one or two further heteroatoms and can be substituted by $C_{1-6}$ alkyl groups.

A prominent group is formed by those compounds of the formula I in which $R_2$ and $R_3$ independently of one another are hydrogen, $C_1$–$C_6$alkyl or $C_1$–$C_6$alkyl substituted by halogen, cyano, nitro, $C_1$–$C_4$alkoxy, $C_3$–$C_6$trialkylsilyl, hydroxyl, amino, ammonium, tri-$C_1$–$C_4$alkylammonium, —COOH, —COOM, in which M is ammonium or an alkali metal or alkaline earth metal atom, $C_3$–$C_8$cycloalkyl, $C_1$–$C_5$alkylcarbonyloxy, phenylcarbonyloxy, naphthylcarbonyloxy, $C_1$–$C_6$alkylamino, $C_1$–$C_5$alkoxycarbonyl, $C_2$–$C_6$dialkylamino or phenyl, it being possible for the phenyl ring to be substituted by halogen, cyano, nitro, —$OR_5$, —$NR_{10}R_{11}$, $C_1$–$C_4$alkyl, formyl, $C_1$–$C_4$alkylcarbonyl, $COOR_7$, $C_1$–$C_4$alkylthio, $C_1$–$C_4$alkylsulfonyl or —$CONR_8R_9$, or $R_2$ and $R_3$ independently of one another are $C_2$–$C_6$alkenyl or $C_2$–$C_6$alkenyl substituted by halogen, cyano, nitro, $C_1$–$C_4$alkoxy, $C_3$–$C_6$-trialkylsilyl, hydroxyl, amino, ammonium, tri-$C_1$–$C_4$alkylammonium, —COOH, —COOM, in which M is ammonium or an alkali metal or alkaline earth metal atom, $C_1$–$C_6$alkylamino, $C_2$–$C_5$alkoxycarbonyl, $C_2$–$C_6$dialkylamino or phenyl, it being possible for the phenyl ring to be substituted by halogen, cyano, nitro, —$OR_5$, —$NR_{10}R_{11}$, $C_1$–$C_4$alkyl, formyl, $C_1$–$C_4$alkylcarbonyl, $COOR_7$, $C_1$–$C_4$alkylthio, $C_1$–$C_4$-alkylsulfonyl or —$CONR_8R_9$, or $R_2$ and $R_3$ independently of one another are $C_3$–$C_6$alkynyl or $C_3$–$C_6$alkynyl substituted by halogen, cyano, nitro, $C_1$–$C_8$alkoxy, $C_3$–$C_6$trialkylsilyl, hydroxyl, amino, ammonium, tri-$C_1$–$C_4$alkylammonium, —COOH, —COOM, in which M is ammonium or an alkali metal or alkaline earth metal atom, $C_1$–$C_6$alkylamino, $C_2$–$C_5$alkoxycarbonyl, $C_2$–$C_6$dialkylamino or phenyl, it being possible for the phenyl ring to be substituted by halogen, cyano, nitro, —$OR_5$, —$NR_{10}R_{11}$, $C_1$–$C_4$alkyl, formyl, $C_1$–$C_4$alkylcarbonyl, $COOR_7$, $C_1$–$C_4$alkylthio, $C_1$–$C_4$alkylsulfonyl or —$CONR_8R_9$, or $R_2$ and $R_3$ independently of one another are formyl, $C_1$–$C_8$alkylcarbonyl, $C_2$–$C_8$alkenylcarbonyl, $C_4$–$C_9$cycloalkylcarbonyl, $C_6$–$C_9$cycloalkenylcarbonyl or $C_3$–$C_8$cycloalkyl-$C_1$–$C_6$alkylcarbonyl, it being possible for these substituents to be substituted by halogen, cyano, nitro, hydroxyl, amino, $C_1$–$C_6$alkylamino, $C_2$–$C_7$dialkylamino, —COOH, —COOM, in which M is ammonium or an alkali metal or alkaline earth metal atom, $C_2$–$C_8$alkoxycarbonyl, $C_4$–$C_{10}$cycloalkoxycarbonyl, $C_1$–$C_8$alkylaminocarbonyl or $C_2$–$C_8$dialkylaminocarbonyl, or $R_2$ and $R_3$ independently of one another are heterocyclyl, heterocyclylcarbonyl, heterocyclyl substituted by halogen, cyano, nitro, $C_1$–$C_5$alkyl, $C_1$–$C_5$alkoxy, $C_1$–$C_5$alkylcarbonyl, $C_1$–$C_5$alkylcarbonyloxy, $C_1$–$C_6$alkoxycarbonyl, aminocarbonyl, $C_1$–$C_6$alkylaminocarbonyl or $C_2$–$C_8$dialkylaminocarbonyl, or heterocyclylcarbonyl substituted by halogen, cyano, nitro, $C_1$–$C_4$alkyl, $C_1$–$C_4$alkoxy, $C_1$–$C_4$alkylcarbonyl, $C_1$–$C_4$alkoxycarbonyl, aminocarbonyl, $C_1$–$C_6$alkylamino or $C_1$–$C_5$alkylcarbonyloxy, or $R_2$ and $R_3$ independently of one another are phenylcarbonyl, biphenylcarbonyl, naphthylcarbonyl, phenyl-$C_1$–$C_6$alkylcarbonyl, biphenyl-$C_1$–$C_6$alkylcarbonyl, naphthyl-$C_1$–$C_6$alkylcarbonyl, phenyl-$C_2$–$C_6$alkenylcarbonyl, biphenyl-$C_2$–$C_6$alkenylcarbonyl or naphthyl-$C_2$–$C_6$alkenylcarbonyl, it being possible for these substituents to be substituted by $C_1$–$C_4$alkyl, $C_1$–$C_4$alkoxy, $C_1$–$C_4$alkylthio, $C_1$–$C_4$halogenoalkyl, $C_1$–$C_4$alkylcarbonyl, halogen, cyano, amino, nitro, —$COOR_7$, $C_1$–$C_5$alkoxycarbonyl, hydroxyl, $C_1$–$C_4$alkylsulfonyl, $C_1$–$C_5$alkylaminocarbonyl or $C_2$–$C_6$dialkylaminocarbonyl, or $R_2$ and $R_3$ independently of one another are phenyl or naphthyl, it being possible for these substituents to be substituted by halogen, cyano, nitro, $C_1$–$C_4$alkyl, $C_1$–$C_4$alkoxy, $C_1$–$C_4$alkylthio, —COOH, —$CONH_2$, $C_1$–$C_5$alkylaminocarbonyl, $C_2$–$C_7$dialkylaminocarbonyl, $C_1$–$C_4$alkylcarbonyl or $C_1$–$C_5$alkoxycarbonyl, or $R_2$ and $R_3$, together with the nitrogen atom to which they are bonded, form a heterocyclic ring, which can be substituted $C_1$–$C_4$alkyl, $C_1$–$C_4$alkoxy, halogen, cyano or nitro, or $R_2$ and $R_3$ independently of one another are amino, $C_1$–$C_4$alkylamino, $C_2$–$C_6$dialkylamino, phenylamino, $C_1$–$C_5$alkylcarbonylamino, $C_1$–$C_5$alkoxycarbonylamino, hydroxyl, $C_1$–$C_4$alkoxy, $C_1$–$C_5$alkylcarbonyloxy or phenoxy, $R_5$ is hydrogen, $C_1$–$C_6$alkyl, $C_1$–$C_6$halogenoalkyl, $C_2$–$C_6$alkoxyalkyl, $C_1$–$C_6$cyanoalkyl, phenyl, halogenophenyl, $C_1$–$C_4$alkoxyphenyl, phenyl-$C_1$–$C_4$alkyl, $C_1$–$C_4$alkylcarbonyl, benzoyl, halogenobenzoyl, $C_1$–$C_4$alkylamino, $C_2$–$C_6$dialkylamino, $C_3$–$C_6$trialkylsilyl, $C_3$–$C_6$cycloalkyl, $C_2$–$C_4$alkenyl or $C_3$–$C_4$alkynyl, $R_7$ is hydrogen, $C_1$–$C_4$alkyl, $C_1$–$C_4$halogenoalkyl, $C_1$–$C_4$cyanoalkyl, phenyl, halogenophenyl, $C_2$–$C_4$alkoxyalkyl, heterocyclyl or halogenoheterocyclyl, $R_8$ and $R_9$ independently of one another are hydrogen, phenyl, halogenophenyl, $C_1$–$C_4$alkyl, $C_1$–$C_4$halogenoalkyl, $C_1$–$C_4$cyanoalkyl, $C_3$–$C_4$alkenyl, $C_3$–$C_4$alkynyl or $C_2$–$C_4$alkoxyalkyl, or $R_8$ and $R_9$, together with the nitrogen atom to which they are bonded, form a heterocyclic radical, which can be substituted by $C_1$–$C_4$alkyl, $R_{10}$ and $R_{11}$ independently of one another are hydrogen, phenyl, halogenophenyl, $C_1$–$C_4$alkyl, $C_1$–$C_4$haloalkyl, $C_1$–$C_4$cyanoalkyl, $C_3$–$C_4$alkenyl, $C_3$–$C_4$alkynyl, $C_2$–$C_4$alkoxyalkyl, formyl, $C_1$–$C_4$alkylcarbonyl or phenylcarbonyl, it being possible for the phenyl moiety therein to be substituted by $C_1$–$C_4$alkyl, halogen, $C_1$–$C_4$alkoxy, hydroxyl, cyano, nitro or $C_1$–$C_4$alkoxycarbonyl, or $R_{10}$ and $R_{11}$, together with the nitrogen atom to which they are bonded, form a heterocyclic radical, which can be substituted by $C_1$–$C_4$alkyl.

Compounds of the formula I which are of particular interest are furthermore those in which $R_2$ and $R_3$ independently of one another are hydrogen, $C_1$–$C_6$alkyl or $C_1$–$C_6$alkyl substituted by halogen, hydroxyl, amino, ammonium, tri-$C_1$–$C_4$alkylammonium, —COOH, —COOM, in which M is ammonium or an alkali metal or alkaline earth metal atom, $C_1$–$C_5$alkylcarbonyloxy, phenylcarbonyloxy, $C_1$–$C_6$alkylamino, $C_1$–$C_5$alkoxycarbonyl or $C_2$–$C_6$dialkylamino, or $R_2$ and $R_3$ independently of one another are formyl, $C_1$–$C_8$alkylcarbonyl, $C_2$–$C_8$alkenylcarbonyl, $C_4$–$C_9$cycloalkylcarbonyl, $C_6$–$C_9$cycloalkenylcarbonyl or $C_3$–$C_8$cycloalkyl-$C_1$–$C_6$alkylcarbonyl, it being possible for these substituents to be substituted by halogen, cyano, hydroxyl, amino, —COOH or —COOM, in which M is ammonium or an alkali metal or alkaline earth metal atom, or $R_2$ and $R_3$ independently of one another are heterocyclyl, heterocyclylcarbonyl, heterocyclyl substituted by halogen, cyano, nitro, $C_1$–$C_5$alkyl, $C_1$–$C_5$alkoxy or $C_1$–$C_6$alkoxycarbonyl, or heterocyclylcarbonyl substituted by halogen, cyano, nitro, $C_1$–$C_4$alkyl, $C_1$–$C_4$alkoxy or $C_1$–$C_4$alkoxycarbonyl, or $R_2$ and $R_3$ independently of one another are phenylcarbonyl, biphenylcarbonyl, naphthylcarbonyl, phenyl-$C_1$–$C_6$alkylcarbonyl, biphenyl-$C_1$–$C_6$alkylcarbonyl, naphthyl-$C_1$–$C_6$alkylcarbonyl, phenyl-$C_2$–$C_6$alkenylcarbonyl, biphenyl-$C_2$–$C_6$alkenylcarbonyl or naphthyl-$C_2$–$C_6$alkenylcarbonyl, it being possible for these substituents to be substituted by $C_1$–$C_4$alkyl, $C_1$–$C_4$alkoxy, $C_1$–$C_4$alkylthio, $C_1$–$C_4$halogenoalkyl, $C_1$–$C_4$alkylcarbonyl, halogen, cyano, amino, nitro, —COOH, $C_1$–$C_5$alkoxycarbonyl, hydroxyl or $C_1$–$C_4$alkylsulfonyl, or $R_2$ and $R_3$ independently of one another are phenyl or naphthyl, it being possible for these substitutents to be substituted by halogen, cyano, $C_1$–$C_4$alkyl, $C_1$–$C_4$alkoxy, $C_1$–$C_4$alkylthio, —COOH or $C_1$–$C_6$alkoxycarbonyl, or $R_2$ and $R_3$, together with the nitrogen atom to which they are bonded, form a heterocyclic ring, which can be substituted by $C_1$–$C_4$alkyl, $C_1$–$C_4$alkoxy, halogen or cyano and in which, in particular, $R_2$ and $R_3$ are hydrogen, or $R_2$ and $R_3$ independently of one another are formyl, $C_1$–$C_8$alkylcarbonyl, $C_2$–$C_8$alkenylcarbonyl, $C_4$–$C_9$cycloalkylcarbonyl, $C_6$–$C_9$cycloalkenylcarbonyl or $C_3$–$C_8$cycloalkyl-$C_1$–$C_6$alkylcarbonyl, it being possible for these substituents to be substituted by halogen, cyano, hydroxyl or amino, or $R_2$ and $R_3$ are phenylcarbonyl, it being possible for the phenyl ring to be substituted by $C_1$–$C_4$alkyl, $C_1$–$C_4$alkoxy, $C_1$–$C_4$alkylthio, $C_1$–$C_4$halogenoalkyl, halogen, cyano, nitro, —COOH, $C_1$–$C_5$alkoxycarbonyl, hydroxyl or $C_1$–$C_4$alkylsulfonyl.

Another preferred sub-group is formed by those compounds of the formula I in which X is oxygen or $S(O)_x$, in which x is the number 0, 1 or 2, and $R_4$ is methyl substituted by halogen, cyano, nitro or $OR_5$, or $R_4$ is $C_2$–$C_8$alkyl, $C_3$–$C_8$alkenyl, $C_3$–$C_8$alkynyl, $C_3$–$C_8$cycloalkyl, $C_5$–$C_8$cycloalkenyl, $C_3$–$C_8$cycloalkyl-$C_1$–$C_4$alkyl or $C_1$–$C_4$alkyl-$C_3$–$C_8$cycloalkyl, it being possible for these substituents to be substituted by halogen, cyano, nitro, =O or —$OR_5$, or $R_4$ is phenyl substituted by halogen, cyano, nitro, amino, —COOH, hydroxyl, $C_1$–$C_4$alkyl, $C_1$–$C_4$alkyloxy, $C_1$–$C_4$alkylthio, $C_1$–$C_4$halogenoalkyl, $C_1$–$C_4$halogenoalkoxy, $C_1$–$C_4$halogenalkylthio, $C_2$–$C_6$alkoxycarbonylalkoxy, $C_1$–$C_4$alkylsulfinyl, $C_1$–$C_4$alkylsulfonyl, $C_1$–$C_6$alkyloxycarbonyl, $C_1$–$C_6$alkylcarbonyl, —$CONH_2$, formyl, $C_1$–$C_5$alkylaminocarbonyl, $C_2$–$C_7$dialkylaminocarbonyl, $C_1$–$C_4$alkylamino, $C_2$–$C_6$dialkylamino, $C_3$–$C_6$trialkylsilyl, $C_1$–$C_6$alkylcarbonylamino, $C_1$–$C_6$alkylcarbonyloxy, phenoxy, halogenophenoxy or pyridyloxy, or $R_4$ is biphenyl, naphthyl, heterocyclyl, $C_1$–$C_4$alkylphenyl, $C_1$–$C_4$alkylnaphthyl, phenyl-$C_1$–$C_4$alkyl or naphthyl-$C_1$–$C_4$alkyl, it being possible for these substituents to be substituted by halogen, cyano, nitro, amino, —COOH, hydroxyl, $C_1$–$C_4$alkyl, $C_1$–$C_4$alkyloxy, $C_1$–$C_4$alkylthio, $C_1$–$C_4$halogenoalkyl, $C_1$–$C_4$halogenoalkoxy, $C_1$–$C_4$halogenoalkylthio, $C_2$–$C_6$alkoxycarbonylalkoxy, $C_1$–$C_4$alkylsulfinyl, $C_1$–$C_4$alkylsulfonyl, $C_1$–$C_6$alkyloxycarbonyl, $C_1$–$C_6$alkylcarbonyl, —$CONH_2$, formyl, $C_1$–$C_5$alkylaminocarbonyl, $C_2$–$C_7$dialkylaminocarbonyl, $C_3$–$C_6$trialkylsilyl, $C_1$–$C_6$alkylcarbonylamino, $C_1$–$C_6$alkylcarbonyloxy, phenoxy, halogenophenoxy or pyridyloxy, and $R_5$ is hydrogen, $C_1$–$C_6$alkyl, $C_1$–$C_6$halogenoalkyl, $C_2$–$C_6$alkoxyalkyl, $C_1$–$C_6$cyanoalkyl, phenyl, halogenophenyl, $C_1$–$C_4$alkoxyphenyl, phenyl-$C_1$–$C_4$alkyl, $C_1$–$C_4$alkylcarbonyl, benzoyl, halogenobenzoyl, $C_1$–$C_4$alkylamino, $C_2$–$C_6$dialkylamino, $C_3$–$C_6$trialkylsilyl, $C_3$–$C_6$cycloalkyl, $C_2$–$C_4$alkenyl or $C_3$–$C_4$alkynyl.

Preferred compounds from this group are those in which X is oxygen or sulfur and $R_4$ is methyl substituted by halogen or cyano, or $R_4$ is $C_2$–$C_8$alkyl, $C_2$–$C_8$alkenyl, $C_3$–$C_8$alkynyl, $C_3$–$C_8$cycloalkyl, $C_5$–$C_8$cycloalkenyl, $C_3$–$C_8$cycloalkyl-$C_1$–$C_4$alkyl or $C_1$–$C_4$alkyl-$C_3$–$C_8$cycloalkyl, it being possible for these substituents in turn to be substituted by halogen or cyano, or $R_4$ is phenyl substituted by halogen, cyano, nitro, amino, $C_1$–$C_4$alkyl, $C_1$–$C_4$alkyloxy, $C_1$–$C_4$alkylthio, $C_1$–$C_4$halogenoalkyl, $C_1$–$C_4$halogenoalkoxy, $C_2$–$C_6$alkoxycarbonylalkoxy, $C_1$–$C_4$alkylsulfonyl, $C_1$–$C_6$alkyloxycarbonyl, $C_1$–$C_6$alkylcarbonyl, formyl, $C_1$–$C_4$alkylamino, $C_2$–$C_6$dialkylamino, $C_3$–$C_6$trialkylsilyl or $C_2$–$C_6$alkylcarbonyloxy, or $R_4$ is biphenyl, naphthyl, heterocyclyl, $C_1$–$C_4$alkylphenyl, $C_1$–$C_4$alkylnaphthyl, phenyl-$C_1$–$C_4$alkyl or naphthyl-$C_1$–$C_4$alkyl, it being possible for these substituents in turn to be substituted by halogen, cyano, nitro, amino, $C_1$–$C_4$alkyl, $C_1$–$C_4$alkyloxy, $C_1$–$C_4$alkylthio, $C_1$–$C_4$halogenoalkyl, $C_1$–$C_4$halogenoalkoxy, $C_2$–$C_6$alkoxycarbonylalkoxy, $C_1$–$C_4$alkylsulfonyl, $C_1$–$C_6$alkyloxycarbonyl, $C_1$–$C_6$alkylcarbonyl, $C_3$–$C_6$trialkylsilyl or $C_1$–$C_6$alkylcarbonyloxy, in particular compounds of the formula I in which X is oxygen and $R_4$ is phenyl or pyridyl substituted by halogen, cyano, nitro, amino, $C_1$–$C_4$alkyl, $C_1$–$C_4$alkyloxy, $C_1$–$C_4$alkylthio, $C_1$–$C_4$halogenoalkyl, halogenomethoxy, $C_1$–$C_4$alkylsulfonyl, $C_1$–$C_4$alkylamino or $C_2$–$C_6$dialkylamino.

Compounds of the formula I which have particular importance are those in which $Q_i$ is $Q_1$, $Q_2$, $Q_3$, $Q_4$, $Q_5$, $Q_7$, $Q_8$, $Q_{11}$, $Q_{13}$, $Q_{17}$, $Q_{18}$, $Q_{20}$ or $Q_{33}$ and $R_{21}$, $R_{22}$, $R_{23}$ and $R_{24}$ independently of one another are $C_1$–$C_4$alkyl, $C_2$–$C_4$alkenyl, $C_2$–$C_4$alkynyl, $C_1$–$C_4$alkoxy, fluorine, chlorine, bromine, phenyl, $C_1$–$C_4$alkoxy-$C_1$–$C_4$alkoxy, trimethlysilyl, trimethylsilyl-$C_1$–$C_4$alkyl, trimethylsilyl-$C_2$–$C_4$alkynyl, di-$C_1$–$C_4$alkylamino, di-$C_1$–$C_4$alkylamino-$C_1$–$C_4$alkyl, $C_1$–$C_4$alkylthio, $C_1$–$C_4$alkylsulfinyl, $C_1$–$C_4$alkylsulfonyl, $C_1$–$C_4$alkylcarbonyl, $C_1$–$C_4$alkoxy-$C_1$–$C_4$alkyl, trifluoromethyl, hydroxy, phenoxy, phenoxycarbonyl or $C_3$–$C_6$cycloalkyl, it being possible for in each case two substituents $R_{21}$, $R_{22}$, $R_{23}$ and $R_{24}$ which are adjacent to form a five- to six-membered ring with the two ring atoms to which they are bonded, $R_2$ is hydrogen, $R_3$ is hydrogen or methylcarbonyl, X is oxygen or sulfur and $R_4$ is phenyl, naphthyl, pyridyl, or thienyl, or phenyl, naphthyl, pyridyl or thienyl substituted by $C_1$–$C_4$alkyl, $C_1$–$C_4$alkoxy, fluorine, chlorine, nitro, cyano, $C_3$–$C_6$cycloalkyloxycarbonyl, $C_1$–$C_6$alkylthio, $C_1$–$C_4$hydroxycarbonyl, alkylsulfonyl, di-$C_1$–$C_4$alkylamino, $C_1$–$C_4$alkylsulfonyl or trifluoromethyl.

Compounds of the formula I which are of prominent importance are those in which $R_2$ and $R_3$ are hydrogen and $Q_i$ is $Q_2$, $Q_4$, $Q_{17}$, $Q_{18}$ or $Q_{20}$.

The compounds of the formula I can be prepared in various ways via process steps which are known per se using known starting materials.

Compounds of the formula I can be prepared, for example, by reacting a trihalogenated thiatriazine of the formula II

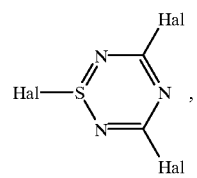

in which the Hal independently of one another are fluorine, bromine or, in particular, chlorine, with the corresponding organometallic compound, to introduce the heteroaryl ring $Q_1$, of the formula III $Q_i$—M    (III), in which $Q_i$ is as defined above and M is a mono- or polyvalent metal atom which can carry a number of $Q_i$ groups depending on the valency.

Compounds of the formula II and their preparation are described, for example, in Chem. Ber. (1991) 124 1347–1352 and Z. Chem. (1976) 16 358–359.

Examples of suitable metals M are, in particular, lithium, magnesium, zinc, aluminium, silicon and tin, and furthermore also manganese, mercury and titanium. In addition to one or more $Q_i$ groups, the polyvalent metal atoms can also carry further substituents, such as halogen, cyano, $C_1$–$C_4$alkyl, acetate, tetrafluoroborate or halogenated or non-halogenated alkanesulfonates. The organometallic compound of the formula III can furthermore be used in combination with salts, such as aluminium chloride, zinc chloride, tin chloride or cerium chloride or aluminium bromide and/or copper bromide, aluminium chloride and bromide and zinc chloride being preferred.

The compounds of the formula III can be prepared by customary methods, for example by reaction of the corresponding halide $Q_i$-halogen with the metal M, by a halogen-metal exchange reaction of the corresponding halide $Q_i$-halogen, in which halogen is preferably bromine or iodine, with a reactive organometallic compound, such as an alkyllithium compound, for example n-butyl-, s-butyl- or t-butyllithium, by treatment of the corresponding heteroaromatic $Q_i$—H with a strongly basic compound, for example lithium diisopropylamide, lithium bistrimethylsilylamide, lithium tetramethylpiperidide, n-butyl- s-butyl- or t-butyllithium and the like. Heteroaromatics of the formula $Q_i$—H can also carry functional groups which facilitate the deprotonation and/or influence the orientation (cf., for example, Snieckus V. Chem. Rev. (1990) 90, 879–933, or Derek J. Chadwick et al. J. Chem. Soc. Perkin I Trans. (1977) 887–893, or Benjamin A. Anderson et al. Synthesis (1996) 583–585), by a transmetallization reaction of an organometallic compound produced as described above with a derivative of another metal, for example a trialkylsilyl or trialkylstannyl halide (cf., for example, H. Zimmer et al. J. Org. Chem. (1984) 49, 5250–5253), by treatment of the corresponding heteroaromatic $Q_i$—H with a metal salt, for example mercury halide or acetate.

Compounds of the formula III and solutions thereof are known and are in some cases commercially obtainable. As a rule, the organometallic compound is not isolated, but is reacted directly with the thiatriazine halide, if appropriate in the presence of a metal salt. Compounds of the formula $Q_i$—H and $Q_i$-halogen are known or can be prepared analogously to known methods (cf., for example, Comprehensive Heterocyclic Chemistry: The Structure, Reactions, Synthesis and Uses of Heterocyclic Compounds, Alan R. Katritzky and Charles W. Rees, (Editor: Kevin T. Potts), Pergamon Press, (1984), volume 4–6 and the literature references contained therein).

The introduction of the group $Q_i$ can be carried out in an aprotic solvent, such as a hydrocarbon, for example hexane, heptane or toluene, or an ether, such as dioxane, diethyl ether or, in particular, tetrahydrofuran, at temperatures of (depending on the solvent) –100° C., to 150° C., in particular –80° C. to 50° C.

The introduction of the group $Q_i$ can also be carried out by a Friedel-Crafts reaction between the heteroaromatic $Q_i$—H and a compound of the formula II, in the presence or absence of a catalyst, for example a Lewis acid (for example $AlCl_3$, $SnCl_4$, and the like) or activated clay (for examplel montmorillonite). This reaction can be carried out in an aprotic solvent, such as a hydrocarbon, for example nitrobenzene, benzene, carbon tetrachloride and the like, or an ether, for example, diethyl ether or tetrahydrofuran, at temperatures of (depending on the solvent) –50° C. to 120° C., in particular –10° C. to 60° C.

The resulting compounds of the formula IV

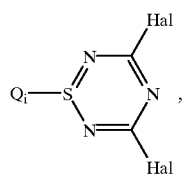

(IV)

are novel and the present invention also relates to them.

The —$NR_2R_3$—  and —$XR_4$ substituents can be introduced into the compound of the formula IV in any sequence.

The reaction of the compounds of the formula IV with the compoounds of the formula V

H—$XR_4$ (V), in which X and $R_4$ are as defined above, to give the compounds of the formula VI

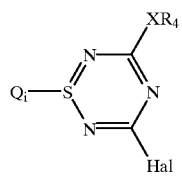

(VI)

is advantageously carried out by a procedure in which, before the reaction with the compounds of the formula IV, the compounds of the formula V are pretreated with a base, such as a metal hydride, for example lithium, sodium or potassium hydride, a metal hydroxide, such as sodium or potassium hydroxide, or a basic salt, such as sodium or potassium carbonate, preferably in equivalent amounts. Alternatively, the reaction mixture of the compounds of the formulae IV and V can be treated with the bases mentioned. Suitable solvents for this step are hydrocarbons, such as hexane or toluene, halogenated hydrocarbons, such as chlorobenzene, ethers, such as tetrahydrofuran, dioxane or diethyl ether, and tertiary amides, such as dimethylformamide. It is also possible to employ a mixture of these solvents with water, a phase transfer catalyst then advantageously being used. The reaction temperatures are as a rule between –50° C. and 100° C., preferably between 0° C. and 40° C.

The compounds of the formula V are known and can be prepared in a manner familiar to the expert.

The compounds of the formula VI are novel and the present invention also relates to them.

The compounds of the formula VI can be converted into the end products of the formula I by reaction with a compound of the formula VII $M_1$—$NR_2R_3$ (VII), in which $R_2$ and $R_3$ are as defined above and $M_1$ is hydrogen or a metal atom, such as lithium, sodium, potassium or calcium, the reaction advantageously being carried out in the presence of a base. Preferably, $M_1$ is hydrogen if $R_2$ and/or $R_3$ are hydrogen. If $R_2$ or $R_3$ is an acyl group, $M_1$ is preferably lithium, sodium or potassium.

Suitable solvents for this reaction are hydrocarbons, such as hexane or toluene, halogenated hydrocarbons, such as chlorobenzene or dichloromethane, ethers, such as diethyl ether, dioxane or tetrahydrofuran, alcohols, such as ethanol or isopropanol, esters, such as ethyl acetate, nitriles, such as acetonitrile, or water. The reaction temperatures are in the range from –70° C. to 100° C., in particular 0° C. to 40° C.

If $M_1$ is hydrogen, an acid-binding agent is preferably used in order to collect the Hal acid. This can be, for example, a second equivalent of the compound of the formula VII or a tertiary amine, such as triethylamine or pyridine, or an inorganic base, such as sodium carbonate or potassium carbonate or sodium bicarbonate. If $R_2$, $R_3$ and $M_1$ are hydrogen, an excess of base can be used. If appropriate, the reaction can be carried out under pressure.

The compounds of the formula VII and their preparation are described in the literature.

The reaction conditions to be maintained for the reaction of compound VI with compound VII are also to be observed if the compound of the formula IV is first to be reacted with the base of the formula VII. The compounds obtained in this manner, of the formula VIII

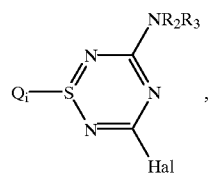

(VIII)

are likewise novel and the present invention relates to them.

The further reaction of the compounds of the formula (VIII) with the compounds of the formula (V) is carried out analogously to the procedure for the reaction of the compounds of the formulae (IV) and (V). In addition, however, a catalytic or, if desired, excess amount of an amine, such as trimethylamine, is added to the reaction mixture.

The end products of the formula I can be isolated in the customary manner by concentration and/or evaporation of the solvent and can be purified by recrystallization or trituration of the solid residue in solvents in which they do not readily dissolve, such as ethers, aromatic hydrocarbons or chlorinated hydrocarbons, or by chromatographic methods.

Other compounds of the formula I can be prepared by customary derivatization of compounds of the formula I. The same applies to the intermediate products of the formulae IV, VI and VIII; for example by cross-coupling, ipso-desilylation or ipso-destannylation on the heteroaryl or derivatization on other parts of the molecule.

The compounds of the formula I according to the invention or compositions comprising these can be used in all the application methods customary in agriculture, for example preemergence application, postemergence application and seed dressing, as well as various methods and techniques, for example controlled release of the active substance. For this, the active substance is applied in solution to mineral granule carriers or polymerized granules (urea/formaldehyde) and the granules are dried. If appropriate, a coating which allows the active substance to be released in metered form over a certain period of time can additionally be applied (coated granules).

The compounds of the formula I can be employed in unchanged form, i.e. as they are obtained in the synthesis, but they are preferably processed in the customary manner with the auxiliaries conventionally used in the art of formulation, for example to give emulsifiable concentrates, directly sprayable or dilutable solutions, dilute emulsions, wettable powders, soluble powders, dusts, granules or microcapsules. The methods of application, such as spraying, atomizing, dusting, wetting, scattering or pouring, like the nature of the composition, are chosen according to the desired aims and the given conditions.

The formulations, i.e. the compositions, formulations or mixtures comprising the active substance of the formula I or at least one active substance of the formula I and as a rule one or more solid or liquid formulation auxiliaries, are prepared in a known manner, for example by intimate mixing and/or grinding of the active substances with the formulation auxiliaries, for example solvents or solid carriers. Surface-active compounds (surfactants) can furthermore additionally be used in the preparation of the formulations.

Possible solvents are: aromatic hydrocarbons, preferably fractions $C_8$ to $C_{12}$, for example xylene mixtures or substituted naphthalenes, phthalic acid esters, such as dibutyl or dioctyl phthalate, aliphatic hydrocarbons, such as cyclohexane or paraffins, alcohols and glycols, and ethers and esters thereof, such as ethanol, ethylene glycol or ethylene glycol monomethyl or -ethyl ether, ketones, such as cyclohexanone, strongly polar solvents, such as N-methyl-2-pyrrolidone, dimethyl sulfoxide or N,N-dimethylformamide, and epoxidized or non-epoxidized vegetable oils, such as epoxidized coconut or soya oil; or water.

Solid carriers which are used, for example for dusts and dispersible powders, are as a rule natural rock powders, such as calcite, talc, kaolin, montmorillonite or attapulgite. Highly disperse silicic acid or highly disperse absorbent polymers can also be added to improve the physical properties of the formulation. Granular adsorptive granule carriers can be porous types, for example pumice, crushed brick, sepiolite or bentonite, and non-adsorptive carrier materials can be, for example, calcite or sand. A large number of pregranulated materials of inorganic or organic nature, such as, in particular, dolomite or comminuted plant residues, can furthermore be used.

Surface-active compounds can be, depending on the nature of the active substance of the formula I to be formulated, nonionic, cationic and/or anionic surfactants and surfactant mixtures having good emulsifying, dispersing and wetting properties.

Suitable anionic surfactants can be both so-called water-soluble soaps and water-soluble synthetic surface-active compounds.

Soaps are the alkali metal, alkaline earth metal or substituted or unsubstituted ammonium salts of higher fatty acids ($C_{10}$–$C_{22}$), for example the Na or K salts of oleic or stearic acid, or of naturally occurring fatty acid mixtures, which can be obtained, for example, from coconut oil or tallow oil. The fatty acid methyl-taurine salts are furthermore also to be mentioned.

More often, however, so-called synthetic surfactants are used, in particular fatty alcohol sulfonates, fatty alcohol sulfates, sulfonated benzimidazole derivatives or alkylarylsulfonates.

The fatty alcohol sulfonates or sulfates are as a rule in the form of alkali metal, alkaline earth metal or substituted or unsubstituted ammonium salts and have an alkyl radical having 8 to 22 C atoms, alkyl also including the alkyl moiety of acyl radicals, for example the Na or Ca salt of ligninsulfonic acid, of dodecylsulfuric acid ester or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain 2 sulfonic acid groups and a fatty acid radical having 8–22 C. Atoms. Alkylarylsulfonates are, for example, the Na, Ca or triethanolamine salts of dodecylbenzenesulfonic acid, of dibutylnaphthalenesulfonic acid or of a naphthalenesulfonic acid-formaldehyde condensation product.

Corresponding phosphates, for example salts of the phosphoric acid ester of a p-nonylphenol-(4-14)-ethylene oxide adduct or phospholipids, can furthermore also be used.

Nonionic surfactants which can be used are primarily polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 8 carbon atoms in the alkyl radical of the alkylphenols.

Further suitable nonionic surfactants are the water-soluble polyethylene oxide adducts, containing 20 to 250 ethylene glycol ether groups and 10 to 100 propylene glycol ether groups, on polypropylene glycol, ethylenediaminopolypropylene glycol and alkyl-polypropylene glycol having 1 to 10 carbon atoms in the alkyl chain. The compounds mentioned usually contain 1 to 5 ethylene glycol units per propylene glycol unit.

Examples of nonionic surfactants are nonylphenolpolyethoxyethanols, castor oil polyglycol ethers, polypropylene-polyethylene oxide adducts, tributylphenoxypolyethoxyethanol, polyethylene glycol and octylphenoxypolyethoxyethanol.

Fatty acid esters of polyoxyethylenesorbitan, such as polyoxyethylenesorbitan trioleate, can furthermore also be used.

The cationic surfactants are, in particular, quaternary ammonium salts, which contain at least one alkyl radical having 8 to 22 C atoms as N-substituents and having lower halogenated or non-halogenated alkyl, benzyl or lower hydroxyalkyl radicals as further substituents. The salts are preferably in the form of halides, methylsulfates or ethylsulfates, for example stearyltrimethylammonium chloride or benzyldi(2-chloroethyl)ethylammonium bromide.

The surfactants which are conventionally used in the art of formulation and can also be used in the compositions according to the invention are described, inter alia, in "McCutcheon's Detergents and Emulsifiers Annual" MC Publishing Corp., Ridgewood N.J., 1981, Stache, H., "Tensid-Taschenbuch [Surfactant Handbook]", Carl Hanser Verlag, Munich/Vienna, 1981 and M. und J. Ash, "Encyclopedia of Surfactants", Vol I–III, Chemical Publishing Co., New York, 1980–81.

The herbicidal formulations as a rule comprise 0.1 to 99% by weight, in particular 0.1 to 95% by weight, of herbicide, 1 to 99.9% by weight, in particular 5 to 99.8% by weight, of a solid or liquid formulation auxiliary and 0 to 25% by weight, in particular 0.1 to 25% by, weight, of a surfactant.

While concentrated compositions tend to be preferred as commercial goods, the end user as a rule uses dilute compositions.

The compositions can also comprise further additives, such as stabilizers, for example epoxidized or non-epoxidized vegetable oils (epoxidized coconut oil, rapeseed oil or soya oil), defoamers, for example silicone oil, preservatives, viscosity regulators, binders, tackifiers and also fertilizers or other active substances.

Preferred formulations have, in particular, the following composition:
(%=per cent by weight)

| Emulsifiable concentrates: | |
|---|---|
| Active substance: | 1 to 90%, preferably 5 to 50% |
| Surface-active agent: | 5 to 30%, preferably 10 to 20% |
| Solvent: | 15 to 94%, preferably 70 to 85% |

| Dusts: | |
|---|---|
| Active substance: | 0.1 to 50%, preferably 0.1 to 1% |
| Solid carrier: | 99.9 to 90%, preferably 99.9 to 99% |

| Suspension concentrates: | |
|---|---|
| Active substance: | 5 to 75%, preferably 10 to 50% |
| Water: | 94 to 24%, preferably 88 to 30% |
| Surface-active agent: | 1 to 40%, preferably 2 to 30% |

| Wettable powders: | |
|---|---|
| Active substance: | 0.5 to 90%, preferably 1 to 80% |
| Surface-active agent: | 0.5 to 20%, preferably 1 to 15% |
| Solid carrier: | 5 to 95%, preferably 15 to 90% |

| Granules: | |
|---|---|
| Active substance: | 0.1 to 30%, preferably 0.1 to 15% |
| Solid carrier: | 99.5 to 70%, preferably 97 to 85% |

The active substances of the formula I are as a rule employed successfully on the plants or their environment with rates of application of 0.001 to 4 kg/ha, in particular 0.005 to 2 kg/ha. The dosage required for the required action can be determined by experiments. It depends on the nature of the action, the stage of development of the crop plants and of the weeds, and the application (location, time, method), and can vary within wide ranges, determined by these parameters.

The compounds of the formula I are distinguished by herbicidal and growth-inhibiting properties, which enable them to be employed in crops of useful plants, in particular in cereals, cotton, soya, sugar beet, sugar cane, plantations, oilseed rape, maize and rice, and for non-selective weed control.

Crops are also to be understood as including those which have been made tolerant towards herbicides and herbicide classes by conventional breeding or genetic engineering methods. The weeds to be controlled can be both mono- and dicotyledon weeds, for example Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola and Veronica.

The following examples illustrate the invention further, without limiting it.

Preparation Examples

EXAMPLE H1

Preparation of 1-(2-benzol[-b-]thienyl)-3,5-dichlorothiatriazine

A 1.6 M solution of n-butyllithium in hexane (107 ml) is added dropwise to a solution of 22.8 g of benzo[-b-]thiophene (0.17 mol) in 200 ml of absolute tetrahydrofuran at a temperature of −70° C., with intensive stirring and cooling. The resulting mixture is stirred at a temperature of −70° C. for 30 minutes. After adding a portion of 23.2 g of $ZnCl_2$ (0.17 mol) and waiting for the exothermic reaction, the mixture is warmed to 0° C. in the course of 1 hour and then cooled to −60° C. A solution of 34.7 g of trichlorothiatriazine (0.17 mol) in 50 ml of tetrahydrofuran is added dropwise, while stirring and cooling. After the mixture has beer stirred at −70° C. for 1 hour, the cooling bath is removed. The reaction mixture is diluted with water at 15° C., crystals precipitating out. The organic solvent is evaporated and the suspension is separated off with a suction filter. After the residue has been rinsed with water and pentane and dried, 1-(2-benzo[-b-]thienyl)-3,5-dichlorothiatriazine is obtained in the form of pale grey crystals having a melting point of 122–123° C.

EXAMPLE H2

Preparation of 3-amino-5-chloro-1-(2-furyl)-thiatriazine

Ammonia is passed into a solution of 3,5dichloro-1-(2-furyl)-thiatriazine (9.44 g, 0.04 mol) in 150 ml of tetrahydrofuran at a temperature of 20° C., while stirring vigorously. When the reaction is complete, the suspension is separated off with a suction filter, and the residue is rinsed with tetrahydrofuran and diethyl ether, subsequently stirred in water, filtered through a suction filter and then dried. 3-Amino-5chloro-1-(2-furyl)-thiatriazine is obtained in the form of white crystals which have a melting point of 215° C. (decomposition).

EXAMPLE H3

Preparation of 3-amino-1-(2-benzo[-b-]furyl)-5-(2-methoxy-4-hydroxycarbonylphenoxy)-thiatriazine 2N sodium hydroxide solution (10.5 ml, 0.021 mol) and 1.5 g of trimethylamine solution (40% in water) are added to a mixture of 2.66 g of 3-amino-1-(2-benzo[-b-]furyl)-5-chloro-thiatriazine (0.010 mol), 80 ml of dichloromethane and 1.85 g of vanillic acid (0.011 mol). The mixture is then stirred at a temperature of 20° C. for 18 hours. Thereafter, the dichloromethane is distilled off in vacuo and 300 ml of water and 1 ml of 2N sodium hydroxide solution are added to the residue. The mixture is introduced onto a suction filter provided with an inert adsorption material (for example Hyflo, silica gel), and the filtrate is then brought to pH 3–4 by means of 2N hydrochloric acid. Crystals precipitate out during this operation. The suspension is separated off with a suction filter and the residue is rinsed with water and then ether and dried. After recrystallization from acetonitrile/tetrahydrofuran (4:1), 3-amino-1-(2-benzo[-b-]furyl)-5-(2-methoxy-4-hydroxycarbonylphenoxy)-thiatriazine is obtained in the form of white crystals which have a melting point of 185° C. (decomposition).

EXAMPLE H4

Preparation of 3,5-dichloro-1-(2-(5-trimethylsilyl)-thienyl)-thiatriazine

A small amount (one spatula-tip) of $AlCl_3$ is added to a solution of 5.71 g of 2,5-bistrimethylsilylthiophene (0.025 mol) and 5.11 g of trichlorothiatriazine (0.025 mol) in 55 ml of absolute dichloromethane at a temperature of 24° C. under a nitrogen atmosphere. The colour of the reaction mixture changes from yellow to red during the course of the exothermic reaction. After the starting materials have been converted, the reaction mixture is evaporated in vacuo, the oily residue is dissolved in a mixture of hexane and dichloromethane, the solution is filtered through silica gel with a suction filter and the silica gel column is rinsed with diethyl ether. The filtrate is concentrated, white crystals of 3,5-dichloro-1-(2-(5-trimethylsilyl)-thienyl)-thiatriazine, which have a melting point of 114–116° C. (decomposition) being isolated.

The nomenclature used in the following is based on the numbering shown below:

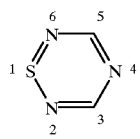

The compounds listed in the following tables can also be prepared in an analogous manner.

TABLE 1

Heteroaromatic ring $Q_i$:

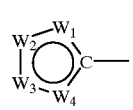

| $Q_i$ | $W_1$ | $W_2$ | $W_3$ | $W_4$ | Heterocyclic radical |
|---|---|---|---|---|---|
| $Q_1$ | $CR_{21}$ | $CR_{22}$ | $CR_{23}$ | $NR_{24}$ | 1H-Pyrrol-2-yl |

TABLE 1-continued

Heteroaromatic ring $Q_i$:

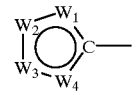

| $Q_i$ | $W_1$ | $W_2$ | $W_3$ | $W_4$ | Heterocyclic radical |
|---|---|---|---|---|---|
| $Q_2$ | $CR_{21}$ | $CR_{22}$ | $CR_{23}$ | O | 2-Furyl |
| $Q_3$ | $CR_{21}$ | $CR_{22}$ | O | $CR_{24}$ | 3-Furyl |
| $Q_4$ | $CR_{21}$ | $CR_{22}$ | $CR_{23}$ | S | 2-Thienyl |
| $Q_5$ | $CR_{21}$ | $CR_{22}$ | N | $NR_{24}$ | 2H-Pyrazol-3-yl |
| $Q_6$ | $CR_{21}$ | $CR_{22}$ | $NR_{23}$ | N | 1H-Pyrazol-3-yl |
| $Q_7$ | $CR_{21}$ | N | $NR_{23}$ | $CR_{24}$ | 1H-Pyrazol-4-yl |
| $Q_8$ | N | $CR_{22}$ | $CR_{23}$ | $NR_{24}$ | 1H-imidazol-2-yl |
| $Q_9$ | $CR_{21}$ | $CR_{22}$ | O | N | Isoxazol-3-yl |
| $Q_{10}$ | $CR_{21}$ | O | $CR_{23}$ | N | Oxazol-4-yl |
| $Q_{11}$ | O | $CR_{22}$ | $CR_{23}$ | N | Oxazol-2-yl |
| $Q_{12}$ | $CR_{21}$ | $CR_{22}$ | N | O | Isoxazol-5-yl |
| $Q_{13}$ | $CR_{21}$ | 0 | N | $CR_{24}$ | Isoxazol-4-yl |
| $Q_{14}$ | O | $CR_{22}$ | N | $CR_{24}$ | Oxazol-5-yl |
| $Q_{15}$ | $CR_{21}$ | $CR_{22}$ | S | N | Isothiazol-3-yl |
| $Q_{16}$ | $CR_{21}$ | S | $CR_{23}$ | N | Thiazol-4-yl |
| $Q_{17}$ | S | $CR_{22}$ | $CR_{23}$ | N | Thiazol-2-yl |
| $Q_{18}$ | $CR_{21}$ | $CR_{22}$ | N | S | Isothiazol-5-yl |
| $Q_{19}$ | $CR_{21}$ | S | N | $CR_{24}$ | Isothiazol-4-yl |
| $Q_{20}$ | S | $CR_{22}$ | N | $CR_{24}$ | Thiazol-5-yl |
| $Q_{21}$ | $CR_{21}$ | N | N | $NR_{24}$ | 3H-[1,2,3]-Triazol-4-yl |
| $Q_{22}$ | $CR_{21}$ | N | $NR_{23}$ | N | 2H-[1,2,3]-Triazol-4-yl |
| $Q_{23}$ | $CR_{21}$ | $NR_{22}$ | N | N | 1H-[1,2,3]-Triazol-4-yl |
| $Q_{24}$ | N | $CR_{22}$ | N | $NR_{24}$ | 2H-[1,2,4]-Triazol-3-yl |
| $Q_{25}$ | N | $CR_{22}$ | $NR_{23}$ | N | 1H-[1,2,4]-Triazol-3-yl |
| $Q_{26}$ | $NR_{21}$ | $CR_{22}$ | N | N | 4H-[1,2,4]-Triazol-3-yl |
| $Q_{27}$ | $CR_{21}$ | O | N | N | [1,2,3]Oxadiazol-4-yl |
| $Q_{28}$ | O | $CR_{22}$ | N | N | [1,3,4]Oxadiazol-2-yl |
| $Q_{29}$ | $CR_{21}$ | N | O | N | Furazan-3-yl |
| $Q_{30}$ | O | N | $CR_{23}$ | N | [1,2,4]Oxadiazol-5-yl |
| $Q_{31}$ | N | O | $CR_{23}$ | N | [1,2,4]Oxadiazol-3-yl |
| $Q_{32}$ | $CR_{21}$ | N | N | O | [1,2,3]Oxadiazol-5-yl |
| $Q_{33}$ | $CR_{21}$ | S | N | N | [1,2,3]Thiadiazol-4-yl |
| $Q_{34}$ | S | $CR_{22}$ | N | N | [1,3,4]Thiadiazol-2-yl |
| $Q_{35}$ | $CR_{21}$ | N | S | N | [1,2,5]Thiadiazol-3-yl |
| $Q_{36}$ | S | N | $CR_{23}$ | N | [1,2,4]Thiadiazol-5-yl |
| $Q_{37}$ | N | S | $CR_{23}$ | N | [1,2,4]Thiadiazol-3-yl |
| $Q_{38}$ | $CR_{21}$ | N | N | S | [1,2,3]Thiadiazol-5-yl |
| $Q_{39}$ | N | N | N | $NR_{24}$ | 1H-Tetrazol-5-yl |
| $Q_{40}$ | N | N | $NR_{23}$ | N | 2H-Tetrazol-5-yl |
| $Q_{41}$ | N | N | N | O | [1,2,3,4]Oxatriazol-5-yl |
| $Q_{42}$ | N | N | O | N | [1,2,3,5]Oxatriazol-4-yl |
| $Q_{43}$ | N | N | N | S | [1,2,3,4]Thiatriazol-5-yl |
| $Q_{44}$ | N | N | S | N | [1,2,3,5]Thiatriazol-4-yl |

TABLE 2
Compounds of the formula Ia:
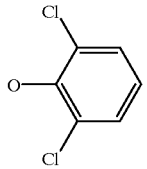
(Ia)
| Comp. No. | $Q_i$ | $R_{21}$ | $R_{22}$ | $R_{23}$ | $R_{24}$ | $XR_4$ |
|---|---|---|---|---|---|---|
| 2.001 | $Q_1$ | H | | —CH=CH—CH=N— | $CH_3$ | 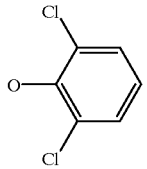 |
| 2.002 | $Q_1$ | $CH_3$ | | —C(Cl)=CH—CH=N— | $COCH_3$ | 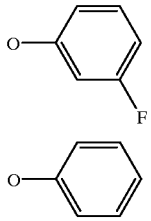 |
| 2.003 | $Q_1$ | | —S—CH=CH— | H | 4—$CH_3$—$C_6H_4$ | 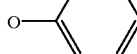 |
| 2.004 | $Q_1$ | | —CH=CH—S— | H | 4—$CH_3$—$C_6H_4$ | 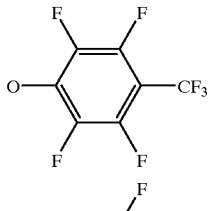 |
| 2.005 | $Q_2$ | H | $CH_3$ | H | — | 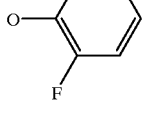 |
| 2.006 | $Q_2$ | H | H | H | — | 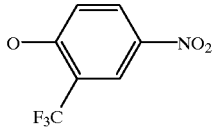 |
| 2.007 | $Q_2$ | H | H | —CH=$CHCH_3$ | — | 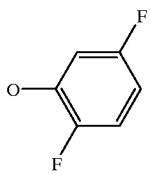 |
| 2.008 | $Q_2$ | H | | —CH=CH—CH=CH— | — | 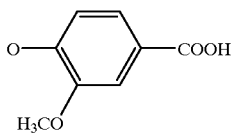 |

TABLE 2-continued
Compounds of the formula Ia:
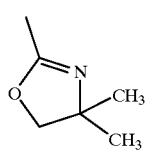
(Ia)
| Comp. No. | $Q_i$ | $R_{21}$ | $R_{22}$ | $R_{23}$ | $R_{24}$ | $XR_4$ |
|---|---|---|---|---|---|---|
| 2.009 | $Q_2$ | 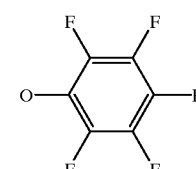 | H | H | — | 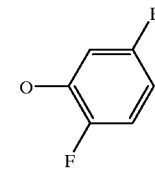 |
| 2.010 | $Q_2$ | H | H | $SCH_3$ | — | 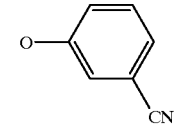 |
| 2.011 | $Q_2$ | H | H | $COOCH_3$ | — | 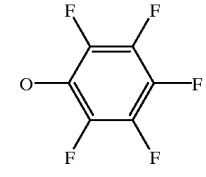 |
| 2.012 | $Q_2$ | H | H | —CH=$CH_2$ | — | 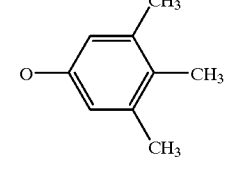 |
| 2.013 | $Q_2$ | H | H | $S(O)CH_3$ | — | 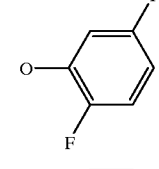 |
| 2.014 | $Q_2$ | H | H | $Si(CH_3)_3$ | — | 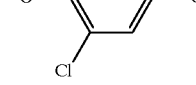 |
| 2.015 | $Q_2$ | H | —C(Cl)=CH—C(Cl)=CH— | | — |  |

TABLE 2-continued
Compounds of the formula Ia:
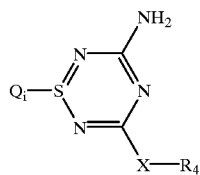
| Comp. No. | $Q_i$ | $R_{21}$ | $R_{22}$ | $R_{23}$ | $R_{24}$ | $XR_4$ |
|---|---|---|---|---|---|---|
| 2.016 | $Q_2$ | H | H | $COCH_3$ | — | pentafluorophenoxy |
| 2.017 | $Q_2$ | H | H | $OCH_3$ | — | 2,5-difluorophenoxy |
| 2.018 | $Q_2$ | H | H | Cl | — | pentafluorophenoxy |
| 2.019 | $Q_2$ | H | —C(OCH$_3$)=CH— CH=CH— | | — | 2,5-dichlorophenoxy |
| 2.020 | $Q_2$ | $CH_3$ | \[structure: H$_3$C—C(=CH$_2$)—C(=CH—)—C(=CH—)—O-i-C$_3$H$_7$\] | | — | 2,6-difluorophenoxy |
| 2.021 | $Q_2$ | H | —C(CH$_3$)=CH—CH=CH— | | — | 2,5-difluorophenoxy |

TABLE 2-continued

Compounds of the formula Ia:

(Ia)

| Comp. No. | $Q_i$ | $R_{21}$ | $R_{22}$ | $R_{23}$ | $R_{24}$ | $XR_4$ |
|---|---|---|---|---|---|---|
| 2.022 | $Q_2$ | H | | —CH=CH—CH=C(CH$_3$)— | — | 2,5-dimethylphenoxy |
| 2.023 | $Q_2$ | H | H | —C≡CH | — | pentafluorophenoxy |
| 2.024 | $Q_2$ | OH | | —CH=CH—CH=CH— | — | 3-methylphenoxy |
| 2.025 | $Q_2$ | H | | —CH=CH—CH=CH— | — | pentafluorophenoxy |
| 2.026 | $Q_2$ | CH$_3$ | | —CH=C(CH$_3$)—C(CH$_3$)=CH— | — | 3,4,5-trimethoxyphenoxy |
| 2.027 | $Q_2$ | H | H | H | — | 2,5-difluorophenoxy |
| 2.028 | $Q_2$ | CH$_3$ | H | H | — | 2,5-difluorophenoxy |

TABLE 2-continued
Compounds of the formula Ia:
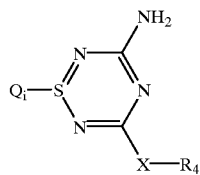
(Ia)
| Comp. No. | $Q_i$ | $R_{21}$ | $R_{22}$ | $R_{23}$ | $R_{24}$ | $XR_4$ |
|---|---|---|---|---|---|---|
| 2.029 | $Q_2$ | H | H | $C_2H_5$ | — | 4-nitro-2-(trifluoromethyl)phenoxy |
| 2.030 | $Q_2$ | Cl | H | H | — | pentafluorophenoxy |
| 2.031 | $Q_2$ | H | H | n-$C_6H_{13}$ | — | phenoxy |
| 2.032 | $Q_2$ | H | H | $CH_3$ | — | 2,5-difluorophenoxy |
| 2.033 | $Q_2$ | —$CH_2$—$C(CH_3)$=$C(CH_3)$—$CH_2$— | | H | — | 2,3-dimethoxyphenoxy |
| 2.034 | $Q_2$ | H | H | $Sn(n-C_4H_9)_3$ | — | 2,5-difluorophenoxy |
| 2.035 | $Q_2$ | H | $CH_3$ | H | — | 2,5-dichlorophenoxy |

TABLE 2-continued

Compounds of the formula Ia:

$$\text{(Ia)}$$

| Comp. No. | $Q_i$ | $R_{21}$ | $R_{22}$ | $R_{23}$ | $R_{24}$ | $XR_4$ |
|---|---|---|---|---|---|---|
| 2.036 | $Q_2$ | H | H | $SO_2CH_3$ | — | 2,5-difluorophenoxy |
| 2.037 | $Q_2$ | | —CH=C(CH₃)—C(CH₃)—CH— | H | — | 2-nitrophenoxy |
| 2.038 | $Q_2$ | H | H | $C_2H_5$ | — | 2,5-difluorophenoxy |
| 2.039 | $Q_2$ | H | H | H | — | pentafluorophenoxy |
| 2.040 | $Q_2$ | H | H | $t\text{-}C_4H_9$ | — | pentafluorophenoxy |
| 2.041 | $Q_2$ | H | H | $n\text{-}C_4H_9$ | — | 2,5-difluorophenoxy |
| 2.042 | $Q_2$ | H | H | I | — | 2,6-dichlorophenoxy |

TABLE 2-continued
Compounds of the formula Ia:
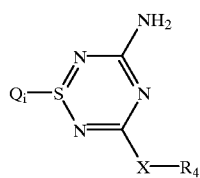
(Ia)
| Comp. No. | $Q_i$ | $R_{21}$ | $R_{22}$ | $R_{23}$ | $R_{24}$ | $XR_4$ |
|---|---|---|---|---|---|---|
| 2.043 | $Q_2$ | H | H | $SCH_3$ | — | 2,5-difluorophenoxy |
| 2.044 | $Q_2$ | H | H | $B(OH)_2$ | — | 4-chloro-2,3,5,6-tetrafluorophenoxy |
| 2.045 | $Q_2$ | H | H | $OCH_3$ | — | 2-fluoro-6-methylpyridin-3-yloxy |
| 2.046 | $Q_2$ | H | —CH=CH—CH=CH— | | — | 2,5-difluorophenoxy |
| 2.047 | $Q_2$ | H | —CO—NH—CH=CH— | | — | 2-methylphenoxy |
| 2.048 | $Q_2$ | H | $CH_3$ | F | — | 2-methylphenoxy |
| 2.049 | $Q_2$ | $OCH_3$ | H | H | — | 2,3,4,5,6-pentafluorophenoxy |

TABLE 2-continued

Compounds of the formula Ia:

(Ia)

| Comp. No. | $Q_i$ | $R_{21}$ | $R_{22}$ | $R_{23}$ | $R_{24}$ | $XR_4$ |
|---|---|---|---|---|---|---|
| 2.050 | $Q_3$ | H | H | — | $CH_3$ | 2-fluoropyridin-3-yloxy |
| 2.051 | $Q_3$ | H | H | — | $CON(C_2H_5)_2$ | 4-nitrophenoxy |
| 2.052 | $Q_3$ | H | H | — | Cl | pentafluorophenoxy |
| 2.053 | $Q_3$ | H | H | — | $OCH_3$ | 3,6-difluoropyridin-2-yloxy |
| 2.054 | $Q_3$ | H | $Si(CH_3)_3$ | — | $CON(C_2H_5)_2$ | 2,5-difluorophenoxy |
| 2.055 | $Q_3$ | H | H | — | $CH_2OCH_3$ | 3-(n-butoxy)phenoxy |
| 2.056 | $Q_3$ | | —CH=CH—CH=CH— | — | $CON(C_2H_5)_2$ | 2,5-difluoropyridin-3-yloxy |

TABLE 2-continued

Compounds of the formula Ia:

(Ia)

| Comp. No. | $Q_i$ | $R_{21}$ | $R_{22}$ | $R_{23}$ | $R_{24}$ | $XR_4$ |
|---|---|---|---|---|---|---|
| 2.057 | $Q_3$ | CONH-t-$C_4H_9$ | $CH_3$ | — | $CH_3$ | 2,6-difluoropyridin-3-yloxy (3,6-difluoropyridin-2-yloxy) |
| 2.058 | $Q_2$ | H | H | 2,4,4-trimethyl-4,5-dihydrooxazol-2-yl | — | pentafluorophenoxy |
| 2.059 | $Q_3$ | —CH=CH—CH=CH— | | — | $CH_2N(CH_3)_2$ | 3,5-dibromo-6-(methoxycarbonyl)pyridin-2-yloxy |
| 2.060 | $Q_3$ | —CH=CH—CH=CH— | | — | $H_2CN$-pyrrolidinyl | 4-methylthiazol-2-yloxymethyl |
| 2.061 | $Q_4$ | H | H | H | — | pentafluorophenoxy |
| 2.062 | $Q_4$ | H | —CH=CH—CH=CH— | | — | 4-chloro-2-nitrophenoxy |
| 2.063 | $Q_4$ | H | $CH_3$ | F | — | 2-methylphenoxy |

TABLE 2-continued
Compounds of the formula Ia:
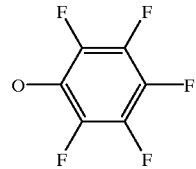
(Ia)
| Comp. No. | $Q_i$ | $R_{21}$ | $R_{22}$ | $R_{23}$ | $R_{24}$ | $XR_4$ |
|---|---|---|---|---|---|---|
| 2.064 | $Q_4$ | $OCH_3$ | H | H | — | 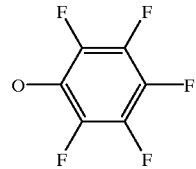 |
| 2.065 | $Q_4$ | H | —CH=CH—CH=CH— | | — | 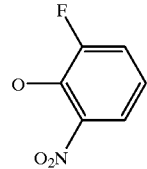 |
| 2.066 | $Q_4$ | H | H | $t\text{-}C_4H_9$ | — | 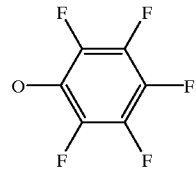 |
| 2.067 | $Q_4$ | H | H | $n\text{-}C_4H_9$ | — | 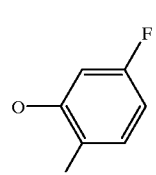 |
| 2.068 | $Q_4$ | H | H | H | — | 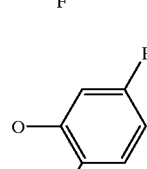 |
| 2.069 | $Q_4$ | H | H | $CH_3$ | — | 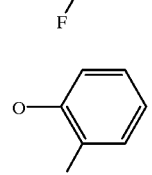 |
| 2.070 | $Q_4$ | $CH_3$ | H | H | — | 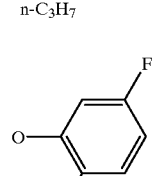 |

TABLE 2-continued
Compounds of the formula Ia:
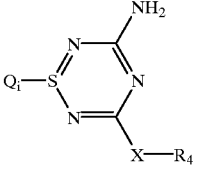
(Ia)
| Comp. No. | $Q_i$ | $R_{21}$ | $R_{22}$ | $R_{23}$ | $R_{24}$ | $XR_4$ |
|---|---|---|---|---|---|---|
| 2.071 | $Q_4$ | H | H | $C_2H_5$ | — | 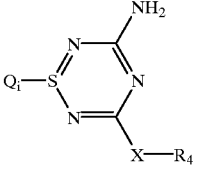 |
| 2.072 | $Q_4$ | Cl | H | H | — | 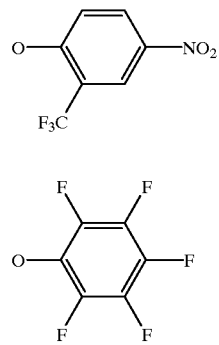 |
| 2.073 | $Q_4$ | H | H | $n\text{-}C_6H_{13}$ | — | 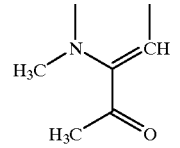 |
| 2.074 | $Q_4$ | H | H | $Si(CH_3)_3$ | — | 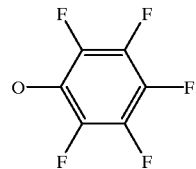 |
| 2.075 | $Q_4$ | H | H | $Sn(n\text{-}C_4H_9)_3$ | — | 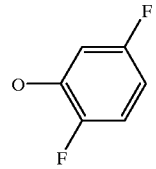 |
| 2.076 | $Q_4$ | H | H | H | — | 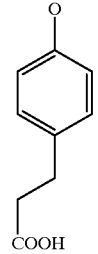 |

TABLE 2-continued

Compounds of the formula Ia:

(Ia)

| Comp. No. | $Q_i$ | $R_{21}$ | $R_{22}$ | $R_{23}$ | $R_{24}$ | $XR_4$ |
|---|---|---|---|---|---|---|
| 2.077 | $Q_4$ | H | H | $t\text{-}C_4H_9$ | — | 2,5-difluorophenoxy |
| 2.078 | $Q_4$ | H | H | I | — | 2,6-dichlorophenoxy |
| 2.079 | $Q_4$ | H | H | $B(OH)_2$ | — | 4-chloro-2,3,5,6-tetrafluorophenoxy |
| 2.080 | $Q_4$ | H | H | 2-thienyl | — | 4-(ethoxycarbonyl)phenoxy |
| 2.081 | $Q_4$ | H | $CH_3$ | H | — | 2,5-dichlorophenoxy |
| 2.082 | $Q_4$ | $CH_3$ | H | H | — | pentafluorophenoxy |
| 2.083 | $Q_4$ | | $-CH_2-CH_2-CH_2-$ $C(OCH_3)_2-$ | $SCH_3$ | — | 3-cyanophenoxy |

TABLE 2-continued

Compounds of the formula Ia:

$$\text{(Ia)}$$

Structure: 1,2,4,6-thiatriazine ring with $Q_i$ on S, $NH_2$ on one carbon, and $X-R_4$ on the other carbon.

| Comp. No. | $Q_i$ | $R_{21}$ | $R_{22}$ | $R_{23}$ | $R_{24}$ | $XR_4$ |
|---|---|---|---|---|---|---|
| 2.084 | $Q_4$ | H | H | $C_2H_5$ | — | O-(2,6-dimethylpyridin-4-yl) |
| 2.085 | $Q_4$ | H | =HC–N(–CH=)–(4-methylphenyl) | | — | O-(3-CO$_2$C$_2$H$_5$-phenyl) |
| 2.086 | $Q_4$ | H | H | $COCH_3$ | — | O-(pentafluorophenyl) |
| 2.087 | $Q_4$ | | $H_2C$–C($CH_3$)$_2$–CH($OC_3H_7$)–$CH_3$ | $SCH_3$ | — | O-(3-methyl-5-isopropyl-phenyl) |
| 2.088 | $Q_4$ | H | H | $CH_3$ | — | O-(3-SC$_5$H$_{11}$-phenyl) |
| 2.089 | $Q_4$ | H | $CH_2$–N(morpholine-like 1,3-oxazinane) | | — | O-(pentafluorophenyl) |
| 2.090 | $Q_4$ | H | —CH=CH—CH=CH— | | — | O-(pentafluorophenyl) |
| 2.091 | $Q_4$ | $CH_3$ | —C($CH_3$)=C($SCH_3$)—S— | | — | $SC_6H_5$ |

TABLE 2-continued

Compounds of the formula Ia:

(Ia)

| Comp. No. | $Q_i$ | $R_{21}$ | $R_{22}$ | $R_{23}$ | $R_{24}$ | $XR_4$ |
|---|---|---|---|---|---|---|
| 2.092 | $Q_4$ | H | | (N=C(OCH$_3$)N(CH$_3$)C(CH$_3$)=N-OCH$_3$ group) | — | 3,4-dimethylphenoxy |
| 2.093 | $Q_4$ | H | H | COOCH$_3$ | — | 3-cyanophenoxy |
| 2.094 | $Q_4$ | H | H | 2-thienyl | — | 2,5-difluorophenoxy |
| 2.095 | $Q_4$ | CH$_3$ | | (H$_3$C)$_2$CH—C(S-CH$_3$)=C(COOC$_4$H$_9$) | — | 3-chlorophenoxy |
| 2.096 | $Q_4$ | H | | —S—CH=CH— | — | 4-amino-2,3,5,6-tetrafluorophenoxy |
| 2.097 | $Q_4$ | H | | —CH=CH—CH=CH— | — | 2,5-difluorophenoxy |
| 2.098 | $Q_4$ | H | H | —C≡CH | — | pentafluorophenoxy |
| 2.099 | $Q_4$ | CH$_3$ | | —CH=N—CH=N— | — | 2-formylphenoxy |

TABLE 2-continued
Compounds of the formula Ia:
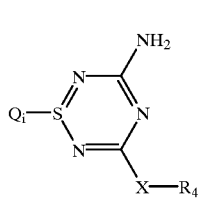
(Ia)
| Comp. No. | $Q_i$ | $R_{21}$ | $R_{22}$ | $R_{23}$ | $R_{24}$ | $XR_4$ |
|---|---|---|---|---|---|---|
| 2.100 | $Q_4$ | $CH_3$ | | —N=CH—N=CH— | — | 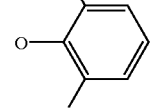 |
| 2.101 | $Q_4$ | $CH_3$ | | (see structure) | — | 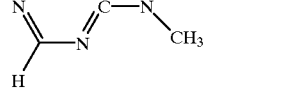 |
| 2.102 | $Q_4$ | H | H | —CH=$CH_2$ | — | 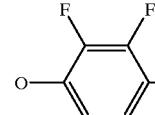 |
| 2.103 | $Q_4$ | H | H | $Si(CH_3)_3$ | — | 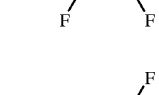 |
| 2.104 | $Q_4$ | H | | (see structure) | — | 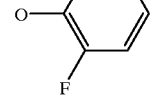 |
| 2.105 | $Q_4$ | H | H | $C_2H_5$ | — |  |
| 2.106 | $Q_4$ | H | | (see structure) | — | 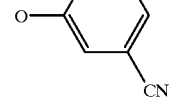 |

TABLE 2-continued

Compounds of the formula Ia:

(Ia)

[Structure: 1,2,4,6-thiatriazine ring with $Q_i$—S, $NH_2$ group, and X—$R_4$ substituent]

| Comp. No. | $Q_i$ | $R_{21}$ | $R_{22}$ | $R_{23}$ | $R_{24}$ | $XR_4$ |
|---|---|---|---|---|---|---|
| 2.107 | $Q_4$ | H | H | —CH=CHCH$_3$ | — | O-(2,5-difluorophenyl) |
| 2.108 | $Q_4$ | H | [=C(OCH$_3$)—C(CH$_3$)(OCH$_3$)—C(=O)NHC$_2$H$_5$] | | — | O-(4-(2-methylbutan-2-yl)phenyl) |
| 2.109 | $Q_4$ | C$_6$H$_5$ | [i-C$_3$H$_7$—S—C(CH$_3$)=N—CH=N—H] | | — | O-(4-methylthiophenyl) |
| 2.110 | $Q_4$ | H | H | CH$_3$ | — | O-pentafluorophenyl |
| 2.111 | $Q_4$ | —CH$_2$—C(CH$_3$)$_2$—CH=C(OCH$_3$)— | | SCH$_3$ | — | OCH$_2$CF$_3$ |
| 2.112 | $Q_4$ | CH$_3$ | —C(CH$_3$)=CH—S— | | — | O-(3,4,5-trimethylphenyl) |
| 2.113 | $Q_4$ | H | H | n-C$_6$H$_{13}$ | — | O-(2,5-difluorophenyl) |
| 2.114 | $Q_4$ | CH$_3$ | [pyrrolidin-1-yl—C(CH$_3$)=N—CH=N—H] | | — | O-(2,3,5,6-tetrafluoro-4-nitrophenyl) |

TABLE 2-continued
Compounds of the formula Ia:
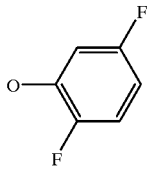
(Ia)
| Comp. No. | $Q_i$ | $R_{21}$ | $R_{22}$ | $R_{23}$ | $R_{24}$ | $XR_4$ |
|---|---|---|---|---|---|---|
| 2.115 | $Q_4$ | H | H | $SO_2CH_3$ | — | 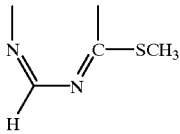 |
| 2.116 | $Q_4$ | $CH_3$ | 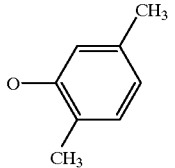 | | — | 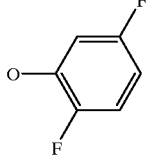 |
| 2.117 | $Q_4$ | $Si(CH_3)_3$ | H | H | — | 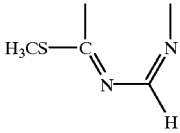 |
| 2.118 | $Q_4$ | $CH_3$ | 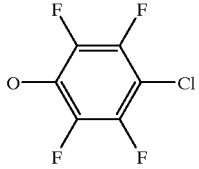 | | — | 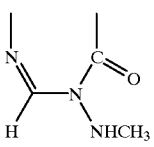 |
| 2.119 | $Q_4$ | H | 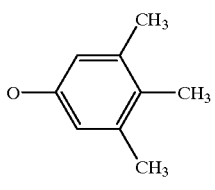 | | — | 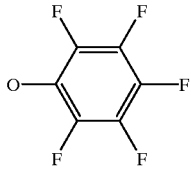 |
| 2.120 | $Q_4$ | H | H | $n$-$C_6H_{13}$ | — | 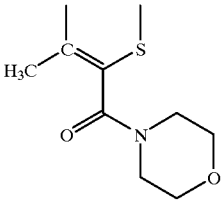 |
| 2.121 | $Q_4$ | $CH_3$ | 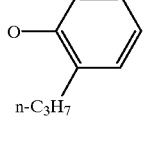 | | — |  |

TABLE 2-continued
Compounds of the formula Ia:
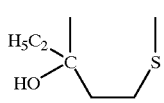
(Ia)
| Comp. No. | $Q_i$ | $R_{21}$ | $R_{22}$ | $R_{23}$ | $R_{24}$ | $XR_4$ |
|---|---|---|---|---|---|---|
| 2.122 | $Q_4$ | H | | 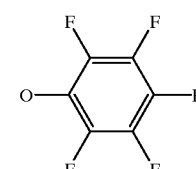 | — | 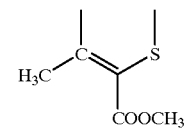 |
| 2.123 | $Q_4$ | $CH_3$ | | 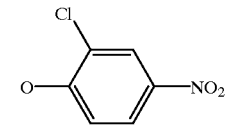 | — | 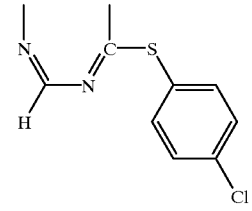 |
| 2.124 | $Q_4$ | $CH_3$ | | 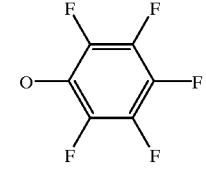 | — | 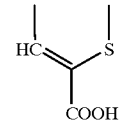 |
| 2.125 | $Q_4$ | H | | 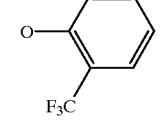 | — | 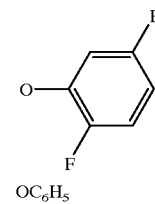 |
| 2.126 | $Q_4$ | H | $CH_3$ | H | — | 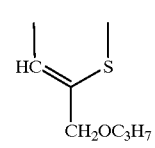 |
| 2.127 | $Q_4$ | H | | 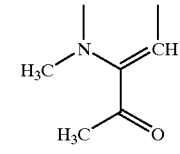 | — | $OC_6H_5$ |
| 2.128 | $Q_4$ | H | | 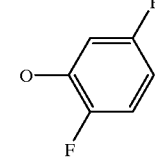 | — | 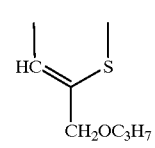 |

TABLE 2-continued

Compounds of the formula Ia:

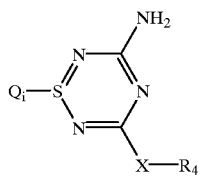

(Ia)

| Comp. No. | $Q_i$ | $R_{21}$ | $R_{22}$ | $R_{23}$ | $R_{24}$ | $XR_4$ |
|---|---|---|---|---|---|---|
| 2.129 | $Q_4$ | H | | ![structure with (CH3)2C=C(SCH3)-C(O)-N-morpholine] | — | ![3,3,5,5-tetramethylcyclohexyloxy] |
| 2.130 | $Q_4$ | H | H | I | — | ![2,5-difluorophenoxy] |
| 2.131 | $Q_4$ | H | | ![ClC(CH3)=C(SCH3)-C(O)-NHCH2C6H5] | — | ![4-(t-C4H9-CH2)phenoxy] |
| 2.132 | $Q_4$ | H | H | $S(O)CH_3$ | — | ![3,4,5-trimethylphenoxy] |
| 2.133 | $Q_4$ | H | | —CH=CH—CH=C(CH$_3$)— | — | ![2-(trifluoromethyl)phenoxy] |
| 2.134 | $Q_4$ | —(CH$_2$)$_2$NH$_2$ | | —CH=CH—C(OCH$_3$)=CH— | — | ![2,5-difluorophenoxy] |
| 2.135 | $Q_4$ | —(CH$_2$)$_2$N(CH$_3$)$_2$ | | —C(OCH$_3$)=CH—CH=CH— | — | ![4-(t-C4H9)phenoxy] |

TABLE 2-continued
Compounds of the formula Ia:
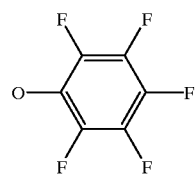
(Ia)
| Comp. No. | $Q_i$ | $R_{21}$ | $R_{22}$ | $R_{23}$ | $R_{24}$ | $XR_4$ |
|---|---|---|---|---|---|---|
| 2.136 | $Q_4$ | H | H | $B(OH)_2$ | — | 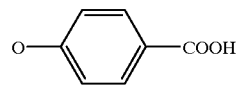 |
| 2.137 | $Q_4$ | —$(CH_2)_2OH$ | | —CH=CH—CH=CH— | — | 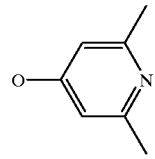 |
| 2.138 | $Q_4$ | —$CH_2SH$ | | —CH=CH—CH=CH— | — | 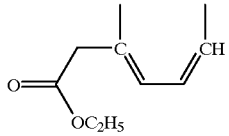 |
| 2.139 | $Q_4$ | $CH_3$ | | —CH=CF—CH=CH— | — | $OCH_2CF_3$ |
| 2.140 | $Q_4$ | H | | 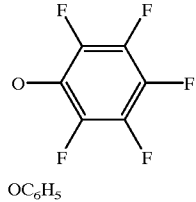 | — | $SCH_2C_6H_5$ |
| 2.141 | $Q_4$ | H | H | 2-thienyl | — | 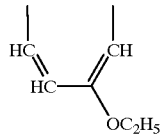 |
| 2.142 | $Q_4$ | $OCH_3$ | | 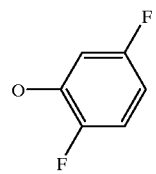 | — | $OC_6H_5$ |
| 2.143 | $Q_4$ | H | H | $SCH_3$ | — |  |

TABLE 2-continued

Compounds of the formula Ia:

$$\text{(Ia)}$$

Structure: 1,2,4,6-thiatriazine ring with $Q_i$-S, $NH_2$ on carbon, and X-$R_4$ substituent.

| Comp. No. | $Q_i$ | $R_{21}$ | $R_{22}$ | $R_{23}$ | $R_{24}$ | $XR_4$ |
|---|---|---|---|---|---|---|
| 2.144 | $Q_4$ | $(CH_2)_2OCOCH_3$ | | 4,5-bis(ethylidene)-2,2-dimethyl-1,3-dioxolane | — | $OCH_2C_7F_{15}$ |
| 2.145 | $Q_4$ | H | H | $Sn(CH_3)_3$ | — | 2,5-difluorophenoxy |
| 2.146 | $Q_4$ | $CH_2CON(CH_3)_2$ | —CH=CH—C(OCH_3)=CH— | | — | 3-(N,N-diethylamino)phenoxy |
| 2.147 | $Q_4$ | H | $CH_3$ | H | — | pentafluorophenoxy |
| 2.148 | $Q_4$ | $H_3CO-C(C_2H_5)(OCH_3)-$ | | —CH=CH—CH=CH— | — | 2-naphthyloxy |
| 2.149 | $Q_4$ | H | H | $OCH_3$ | — | 2,5-difluorophenoxy |
| 2.150 | $Q_4$ | H | —C(OH)=CH—CH=CH— | | — | 2,6-dichlorophenoxy |
| 2.151 | $Q_4$ | H | H | $Sn(n-C_4H_9)_3$ | — | pentafluorophenoxy |

TABLE 2-continued

Compounds of the formula Ia:

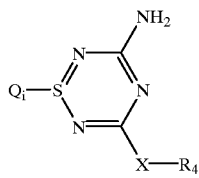

(Ia)

| Comp. No. | $Q_i$ | $R_{21}$ | $R_{22}$ | $R_{23}$ | $R_{24}$ | $XR_4$ |
|---|---|---|---|---|---|---|
| 2.152 | $Q_4$ | $CH_3$ | | —CH=CH—CH=CH— | — | 3,4-methylenedioxyphenoxy |
| 2.153 | $Q_4$ | $CH_2CO_2H$ | | —CH=CH—CH=CH— | — | 3-($SC_5H_{11}$)phenoxy |
| 2.154 | $Q_4$ | $CH_2CO_2C_2H_5$ | | —CH=C(Cl)—CH=CH— | — | pentafluorophenoxy |
| 2.155 | $Q_4$ | $CH_3$ | | —CH=C(Cl)—CH=CH— | — | pentafluorophenoxy |
| 2.156 | $Q_4$ | H | | —CH=C($CH_3$)—CH=CH— | — | 4-($CF_3$)phenoxy |
| 2.157 | $Q_4$ | H | H | Cl | — | pentafluorophenoxy |
| 2.158 | $Q_4$ | $CH_3$ | | —CH=C($CH_3$)—CH=CH— | — | 2-($C_2H_5$)phenoxy |
| 2.159 | $Q_4$ | H | $Si(CH_3)_3$ | H | — | pentafluorophenoxy |

TABLE 2-continued
Compounds of the formula Ia:
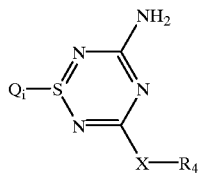
(Ia)
| Comp. No. | $Q_i$ | $R_{21}$ | $R_{22}$ | $R_{23}$ | $R_{24}$ | $XR_4$ |
|---|---|---|---|---|---|---|
| 2.160 | $Q_4$ | $NHC_4H_9$ | | —CH=CH—CH=CH— | — | pentafluorophenoxy |
| 2.161 | $Q_4$ | $CH_2N(CH_3)_2$ | | —CH=CH—CH=CH— | — | 2-(n-$C_3H_7$)phenoxy |
| 2.162 | $Q_4$ | $CH_2$—morpholinyl | | —CH=CH—CH=CH— | — | pentafluorophenoxy |
| 2.163 | $Q_4$ | H | H | n-$C_4H_9$ | — | pentafluorophenoxy |
| 2.164 | $Q_5$ | H | H | — | $C_6H_5$ | 2,4-bis(CF$_3$)phenoxy |
| 2.165 | $Q_5$ | H | $CH_3$ | — | $C_6H_5$ | pentafluorophenoxy |
| 2.166 | $Q_5$ | H | $CH_3$ | — | $CH_2OCH_3$ | 2-naphthyloxy |

TABLE 2-continued

Compounds of the formula Ia:

(Ia)

| Comp. No. | $Q_i$ | $R_{21}$ | $R_{22}$ | $R_{23}$ | $R_{24}$ | $XR_4$ |
|---|---|---|---|---|---|---|
| 2.167 | $Q_5$ | $C_6H_5$ | $CH_3$ | — | $CON(CH_3)_2$ | 2,5-difluorophenoxy |
| 2.168 | $Q_5$ |  | —CH=CH—CH=CH— | — | $CH_3$ | 2-fluoro-6-methylpyridin-3-yloxy |
| 2.169 | $Q_5$ | H | $C_2H_5$ | — | 2-Cl—$C_6H_4$ | 2-methylphenoxy |
| 2.170 | $Q_5$ | H | 3-($NH_2$)—$C_6H_4$ | — | $CH_3$ | 5-chloro-3-fluoropyridin-2-yloxy |
| 2.171 | $Q_5$ | H | $C(OCH_3)_3$ | — | i-$C_3H_7$ | 4-chloro-1-methyl-3-(trifluoromethyl)-1H-pyrazol-5-yloxy |
| 2.172 | $Q_5$ | H | $CH_3$ | — | t-$C_4H_9$ | pentafluorophenoxy |
| 2.173 | $Q_5$ | H | $SCH_3$ | — | t-$C_4H_9$ | pentafluorophenoxy |

TABLE 2-continued
Compounds of the formula Ia:
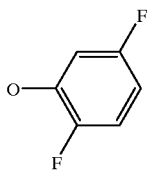
(Ia)
| Comp. No. | $Q_i$ | $R_{21}$ | $R_{22}$ | $R_{23}$ | $R_{24}$ | $XR_4$ |
|---|---|---|---|---|---|---|
| 2.174 | $Q_5$ | H | 2-Thiazolyl | — | $CH_3$ | 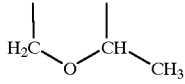 |
| 2.175 | $Q_5$ | \multicolumn{2}{l}{$H_2C$—$O$—$CH$ with $CH_3$, $CH_3$} | — | $CH_3$ | 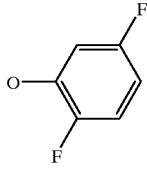 |
| 2.176 | $Q_5$ | H | 3-Cl—$C_6H_4$ | — | $CH_2OC_2H_5$ | 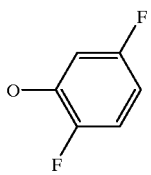 |
| 2.177 | $Q_5$ | H | $CF_3$ | — | $CH_3$ | 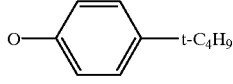 |
| 2.178 | $Q_5$ | H | $CH_3$ | — | $C_6H_5$ | 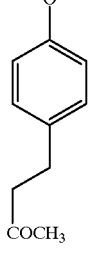 |
| 2.179 | $Q_7$ | H | — | $C_6H_5$ | H | 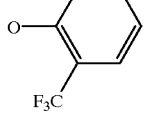 |
| 2.180 | $Q_7$ | $C_6H_5$ | — | $CH_3$ | H | 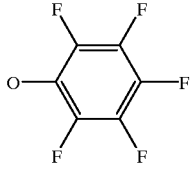 |

TABLE 2-continued
Compounds of the formula Ia:
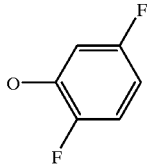
(Ia)
| Comp. No. | $Q_i$ | $R_{21}$ | $R_{22}$ | $R_{23}$ | $R_{24}$ | $XR_4$ |
|---|---|---|---|---|---|---|
| 2.181 | $Q_7$ | H | — | $CH_3$ | $C_6H_5$ | 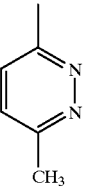 |
| 2.182 | $Q_7$ | $CH_3$ | — | 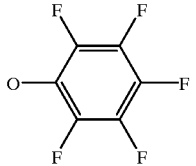 | $CH_3$ |  |
| 2.183 | $Q_7$ | H | — | $CH_3$ | $OCH_3$ | 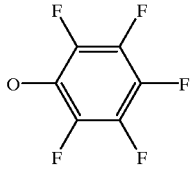 |
| 2.184 | $Q_7$ | $OCH_3$ | — | $CH_3$ | H |  |
| 2.185 | $Q_7$ | $N(CH_3)_2$ | — | $t\text{-}C_4H_9$ | $CH_3$ |  |
| 2.186 | $Q_7$ | $CH_3$ | — | $t\text{-}C_4H_9$ | $N(CH_3)_2$ |  |
| 2.187 | $Q_8$ | — | H | H | $CH_2C_6H_5$ |  |

TABLE 2-continued
Compounds of the formula Ia:
(Ia)
| Comp. No. | $Q_i$ | $R_{21}$ | $R_{22}$ | $R_{23}$ | $R_{24}$ | $XR_4$ |
|---|---|---|---|---|---|---|
| 2.188 | $Q_8$ | — | H | H | $SO_2C_6H_5$ | 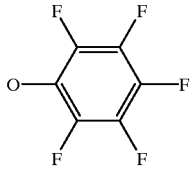 |
| 2.189 | $Q_8$ | — | H | H | COO-t-$C_4H_9$ | 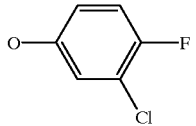 |
| 2.190 | $Q_8$ | — | H | H | CONHt-$C_4H_9$ | 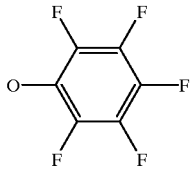 |
| 2.191 | $Q_8$ | — | H | H | $C_6H_5$ | 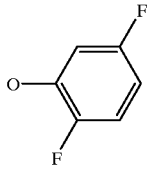 |
| 2.192 | $Q_8$ | — | H | H | $CH_3$ | 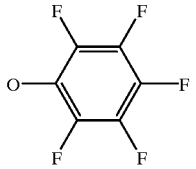 |
| 2.193 | $Q_8$ | — | —CH=CH—CH=CH— | | n-$C_3H_7$ | 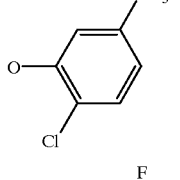 |
| 2.194 | $Q_8$ | — | Cl | Cl | $CH_2C_6H_5$ | 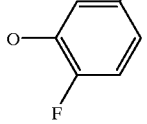 |

TABLE 2-continued

Compounds of the formula Ia:

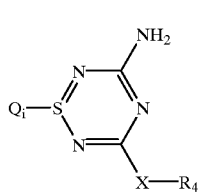

(Ia)

| Comp. No. | $Q_i$ | $R_{21}$ | $R_{22}$ | $R_{23}$ | $R_{24}$ | $XR_4$ |
|---|---|---|---|---|---|---|
| 2.195 | $Q_8$ | — | H | H | CONHCH$_3$ | pentafluorophenoxy |
| 2.196 | $Q_8$ | — | —CH=CH—CH=CH— | | CO-t-C$_4$H$_9$ | pentafluorophenoxy |
| 2.197 | $Q_8$ | — | —CH=CH—CH=CH— | | CONHt-C$_4$H$_9$ | 2,6-difluorophenoxy |
| 2.198 | $Q_8$ | — | CH$_3$ | CH$_3$ | CH$_2$OCH$_3$ | 2,5-difluorophenoxy |
| 2.199 | $Q_8$ | — | —CH$_2$—CH$_2$—CH$_2$—CH$_2$— | | CON(CH$_3$)$_2$ | 2-n-propylphenoxy |
| 2.200 | $Q_8$ | — | H | H | SO$_2$N(CH$_3$)$_2$ | pentafluorophenoxy |
| 2.201 | $Q_{11}$ | — | —CH=C(CH$_3$)—CH=CH— | | — | 2,5-difluorophenoxy |

TABLE 2-continued
Compounds of the formula Ia:
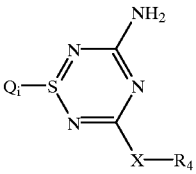
(Ia)
| Comp. No. | $Q_i$ | $R_{21}$ | $R_{22}$ | $R_{23}$ | $R_{24}$ | $XR_4$ |
|---|---|---|---|---|---|---|
| 2.202 | $Q_{11}$ | — | | —CH=CH—C(CH$_3$)=CH— | | — | 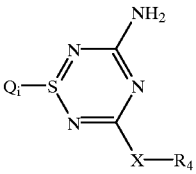 |
| 2.203 | $Q_{11}$ | — | | —CH=CH—C(Cl)=CH— | | — | 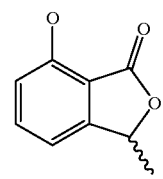 |
| 2.204 | $Q_{11}$ | — | | —CH=CH—CH=CH— | | — | 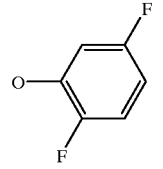 |
| 2.205 | $Q_{11}$ | — | 3-NH$_2$—C$_6$H$_4$ | H | — | 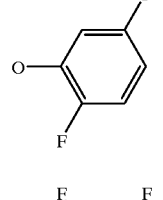 |
| 2.206 | $Q_{11}$ | — | C$_6$H$_5$ | H | — | 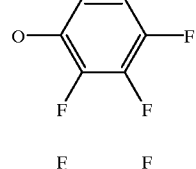 |
| 2.207 | $Q_{11}$ | — | 2-Cl—C$_6$H$_4$ | H | — | 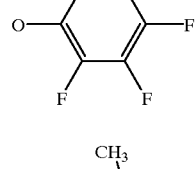 |
| 2.208 | $Q_{11}$ | — | 4-F—C$_6$H$_4$ | H | — | 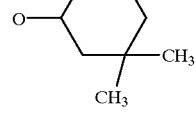 |

TABLE 2-continued
Compounds of the formula Ia:
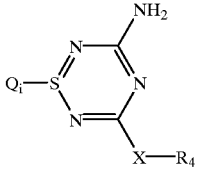
(Ia)
| Comp. No. | $Q_i$ | $R_{21}$ | $R_{22}$ | $R_{23}$ | $R_{24}$ | $XR_4$ |
|---|---|---|---|---|---|---|
| 2.209 | $Q_{11}$ | — | 2-Furyl | H | — | 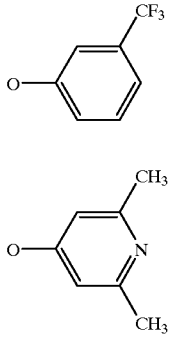 |
| 2.210 | $Q_{11}$ | — | 4-Tolyl | H | — | 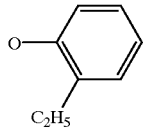 |
| 2.211 | $Q_{11}$ | — | 4-Anisyl | H | — | 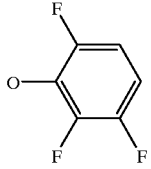 |
| 2.212 | $Q_{11}$ | — | 2-Thienyl | H | — | 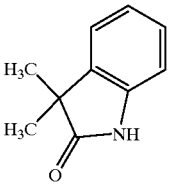 |
| 2.213 | $Q_{11}$ | — | 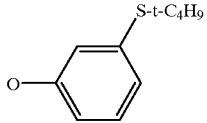 | H | — | 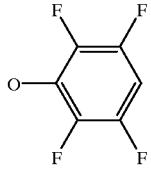 |
| 2.214 | $Q_{11}$ | — | 4-$CF_3$—$C_6H_4$ | $CO_2C_2H_5$ | — | $OC_8H_{17}$ |
| 2.215 | $Q_{11}$ | — | $C_6H_5$ | $CO_2C_2H_5$ | — | |

TABLE 2-continued
Compounds of the formula Ia:
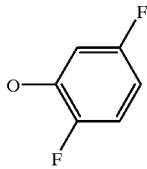
(Ia)
| Comp. No. | $Q_i$ | $R_{21}$ | $R_{22}$ | $R_{23}$ | $R_{24}$ | $XR_4$ |
|---|---|---|---|---|---|---|
| 2.216 | $Q_{11}$ | — | 2,4-Dichloro-phenyl | $CO_2C_2H_5$ | — | 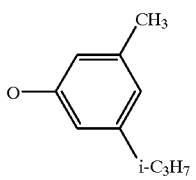 |
| 2.217 | $Q_{11}$ | — | 3-Cl—$C_6H_4$ | $CO_2C_2H_5$ | — | 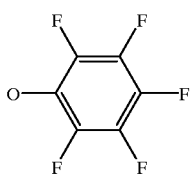 |
| 2.218 | $Q_{11}$ | — | $t$-$C_4H_9$ | $CO_2C_2H_5$ | — | 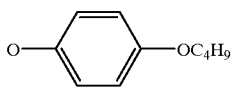 |
| 2.219 | $Q_{13}$ | H | — | — | H | 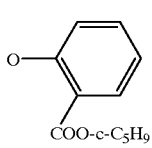 |
| 2.220 | $Q_{13}$ | NHCOOt-$C_4H_9$ | — | — | $CH_3$ | 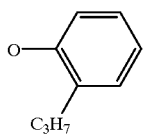 |
| 2.221 | $Q_{13}$ | $CH_3$ | — | — | $CH_3$ | 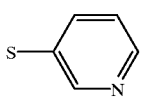 |
| 2.222 | $Q_{13}$ | $C_6H_5$ | — | — | $CH_3$ | 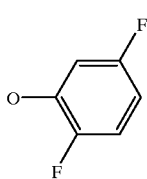 |
| 2.223 | $Q_{13}$ | H | — | — | $CH_3$ |  |

TABLE 2-continued

Compounds of the formula Ia:

| Comp. No. | $Q_i$ | $R_{21}$ | $R_{22}$ | $R_{23}$ | $R_{24}$ | $XR_4$ |
|---|---|---|---|---|---|---|
| 2.224 | $Q_{13}$ | H | — | — | 2-Thienyl | 2-methylphenoxy |
| 2.225 | $Q_{13}$ | $CH_3$ | — | — | $CON(CH_3)_2$ | 2-(ethylsulfonyl)phenoxy |
| 2.226 | $Q_{13}$ | $CH_3$ | — | — | $CH_2OC_2H_5$ | 4-(2-carboxyethyl)phenoxy |
| 2.227 | $Q_{13}$ | H | — | — | $CH(OC_2H_5)_2$ | 2-thienylthio |
| 2.228 | $Q_{13}$ | H | — | — | $HC(OCH_3)(C_3H_7)$ | 2,5-difluorophenoxy |
| 2.229 | $Q_{13}$ | 2,6-dimethyl-methoxyphenyl | — | — | $CH_3$ | pentafluorophenoxy |
| 2.230 | $Q_{13}$ | $C_6H_5$ | — | — | 2-Furyl | 2-nitrophenoxy |

TABLE 2-continued

Compounds of the formula Ia:

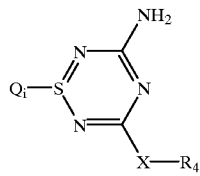

(Ia)

| Comp. No. | $Q_i$ | $R_{21}$ | $R_{22}$ | $R_{23}$ | $R_{24}$ | $XR_4$ |
|---|---|---|---|---|---|---|
| 2.231 | $Q_{13}$ | (CH₃)₃C-C(=O)-N(CH₃)₂ | — | — | 4-Cl—C₆H₄ | 3-pyridyl-S— |
| 2.232 | $Q_{13}$ | $C_6H_5$ | — | — | 2,4-Dichlorophenyl | 2-ethylphenoxy |
| 2.233 | $Q_{13}$ | $CH_3$ | — | — | 3-methyl-1-azabicyclo | 2,3,6-trifluorophenoxy |
| 2.234 | $Q_{13}$ | $(CH_2)_5Cl$ | — | — | $CH_2OCH_3$ | 2,6-dichlorophenoxy |
| 2.235 | $Q_{13}$ | $N(CH_3)C_6H_5$ | — | — | $t-C_4H_9$ | $OCH(CF_3)_2$ |
| 2.236 | $Q_{13}$ | 1-methyl-2-pyrrolidinyl | — | — | $CH_3$ | 2,3,5,6-tetrafluorophenoxy |
| 2.237 | $Q_{13}$ | $CH_3$ | — | — | 1-methyl-2-pyrrolidinyl | 3-(pentylthio)phenoxy |
| 2.238 | $Q_{13}$ | $CH_3$ | — | — | $CF_3$ | $OCH_2C_7F_{15}$ |
| 2.239 | $Q_{16}$ | $OC_2H_5$ | — | $CH_3$ | — | 2-ethylphenoxy |

TABLE 2-continued
Compounds of the formula Ia:
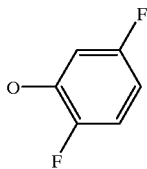
(Ia)
| Comp. No. | $Q_i$ | $R_{21}$ | $R_{22}$ | $R_{23}$ | $R_{24}$ | $XR_4$ |
|---|---|---|---|---|---|---|
| 2.240 | $Q_{18}$ | OH | — | i-$C_3H_7$ | — | 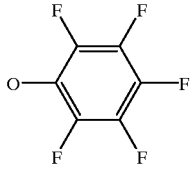 |
| 2.241 | $Q_{15}$ | $OCH_3$ | — | t-$C_4H_9$ | — | 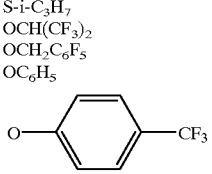 |
| 2.242 | $Q_{17}$ | — | H | H | — | S-i-$C_3H_7$ |
| 2.243 | $Q_{17}$ | — | H | $CH_3$ | — | $OCH(CF_3)_2$ |
| 2.244 | $Q_{17}$ | — | H | $C_6H_5$ | — | $OCH_2C_6F_5$ |
| 2.245 | $Q_{17}$ | — | H | CN | — | $OC_6H_5$ |
| 2.246 | $Q_{17}$ | — | —CH=CH—CH=CH— | | — | 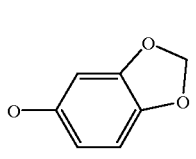 |
| 2.247 | $Q_{17}$ | — | —CF=CH—CH=CH— | | — | 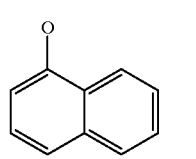 |
| 2.248 | $Q_{17}$ | — | —CH=CH—CH=CF— | | — | 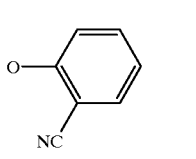 |
| 2.249 | $Q_{17}$ | — | —CH=CH—CCl=CH— | | — | 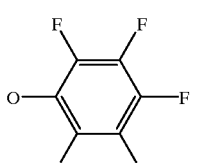 |
| 2.250 | $Q_{17}$ | — | —CH=CH—CH=CH— | | — | 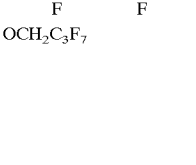 |
| 2.251 | $Q_{17}$ | — | Si($CH_3)_3$ | H | — | $OCH_2C_3F_7$ |

TABLE 2-continued

Compounds of the formula Ia:

(Ia)

| Comp. No. | $Q_i$ | $R_{21}$ | $R_{22}$ | $R_{23}$ | $R_{24}$ | $XR_4$ |
|---|---|---|---|---|---|---|
| 2.252 | $Q_{17}$ | — | $CH_3$ | H | — | 2,4,6-trichlorophenoxy |
| 2.253 | $Q_{17}$ | — | $C_6H_5$ | H | — | 4-(prop-2-ynyloxycarbonyl)phenoxy |
| 2.254 | $Q_{17}$ | — | $Si(CH_3)_3$ | $CH_2OCH_3$ | — | pentafluorophenoxy |
| 2.255 | $Q_{18}$ | $CH_2C_6H_5$ | H | — | — | pentafluorophenoxy |
| 2.256 | $Q_{18}$ | H | NHCOO-t-$C_4H_9$ | — | — | 2,3,5,6-tetrafluorophenoxy |
| 2.257 | $Q_{18}$ | $C_6H_5$ | NHCO-t-$C_4H_9$ | — | — | 2-(prop-2-ynyl)phenoxy |
| 2.258 | $Q_{16}$ | $C_6H_5$ | $CONHN(CH_3)_2$ | — | — | 4-nitrophenoxy |

TABLE 2-continued

Compounds of the formula Ia:

(Ia)

| Comp. No. | $Q_i$ | $R_{21}$ | $R_{22}$ | $R_{23}$ | $R_{24}$ | $XR_4$ |
|---|---|---|---|---|---|---|
| 2.259 | $Q_{18}$ | | —CH=CH—CH=CH— | — | — | 3-nitrophenoxy |
| 2.260 | $Q_{18}$ | H | H | — | — | pentafluorophenoxy |
| 2.261 | $Q_{18}$ | H | $CH_3$ | — | — | 2,5-difluorophenoxy |
| 2.262 | $Q_{18}$ | $NH_2$ | H | — | — | pentafluorophenoxy |
| 2.263 | $Q_{18}$ | $NH_2$ | $CH_3$ | — | — | 3-(N,N-diethylamino)phenoxy |
| 2.264 | $Q_{18}$ | $CON(C_2H_5)_2$ | H | — | — | 2,5-difluorophenoxy |
| 2.265 | $Q_{18}$ | $NHCOOC_2H_5$ | H | — | — | 2,4-bis(trifluoromethyl)phenoxy |

TABLE 2-continued
Compounds of the formula Ia:
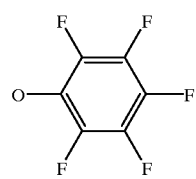
(Ia)
| Comp. No. | $Q_i$ | $R_{21}$ | $R_{22}$ | $R_{23}$ | $R_{24}$ | $XR_4$ |
|---|---|---|---|---|---|---|
| 2.266 | $Q_{18}$ | $NHCOC_6H_5$ | H | — | — | 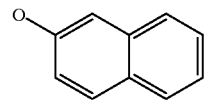 |
| 2.267 | $Q_{18}$ | $C_6H_5$ | $SCH_3$ | — | — | 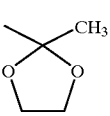 |
| 2.268 | $Q_{18}$ | 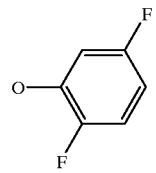 | $CH_3$ | — | — | 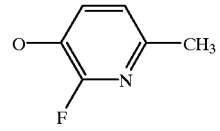 |
| 2.269 | $Q_{18}$ | 4-Tolyl | $SCH_3$ | — | — |  |
| 2.270 | $Q_{18}$ | 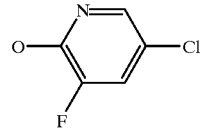 | H | — | — | 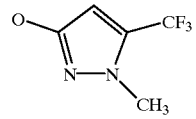 |
| 2.271 | $Q_{18}$ | H | $O\text{-}n\text{-}C_4H_9$ | — | — | 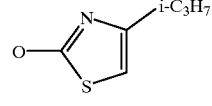 |
| 2.272 | $Q_{18}$ | | $—CH_2—(CH_2)_3—CH_2—$ | — | — | 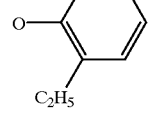 |
| 2.273 | $Q_{18}$ | H | $O\text{-}i\text{-}C_3H_7$ | — | — | |

TABLE 2-continued
Compounds of the formula Ia:
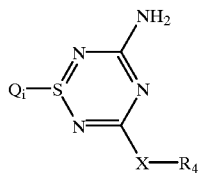
(Ia)
| Comp. No. | $Q_i$ | $R_{21}$ | $R_{22}$ | $R_{23}$ | $R_{24}$ | $XR_4$ |
|---|---|---|---|---|---|---|
| 2.274 | $Q_{18}$ |  | —CH$_2$—(CH$_2$)$_4$—CH$_2$— | — | — | 4-O-(2,6-dimethylpyridinyl) |
| 2.275 | $Q_{18}$ | CH$_3$ | 4-Tolyl | — | — | O-(2,5-difluorophenyl) |
| 2.276 | $Q_{18}$ | H | 2-Tolyl | — | — | S-(2-thienyl) |
| 2.277 | $Q_{18}$ | H | CBr$_3$ | — | — | OCH$_2$CH(CF$_3$)$_2$ |
| 2.278 | $Q_{18}$ | 4-Cl—C$_6$H$_4$ | H | — | — | O-(2-naphthyl) |
| 2.279 | $Q_{18}$ |  | —CH=CH—S— | — | — | O-(pentafluorophenyl) |
| 2.280 | $Q_{18}$ | CH(OC$_2$H$_5$)$_2$ | CH$_3$ | — | — | O-(2,5-difluorophenyl) |
| 2.281 | $Q_{18}$ | 4-Cl—C$_6$H$_4$ | CON(CH$_3$)$_2$ | — | — | O-(2-naphthyl) |
| 2.282 | $Q_{18}$ |  | —S—CH=CH— | — | — | O-(3-methylphenyl) |

TABLE 2-continued
Compounds of the formula Ia:
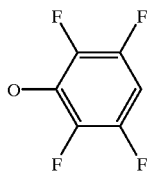
(Ia)
| Comp. No. | $Q_i$ | $R_{21}$ | $R_{22}$ | $R_{23}$ | $R_{24}$ | $XR_4$ |
|---|---|---|---|---|---|---|
| 2.283 | $Q_{18}$ | H | 4-Cl—$C_6H_4$ | — | — | 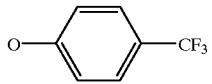 |
| 2.284 | $Q_{20}$ | — | $CH_3$ | — | $CH_3$ | 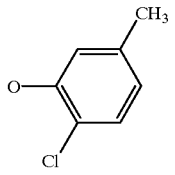 |
| 2.285 | $Q_{20}$ | — | NHCOO-t-$C_4H_9$ | — | H | 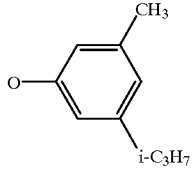 |
| 2.286 | $Q_{20}$ | — | NHCOO-t-$C_4H_9$ | — | $CH_3$ | 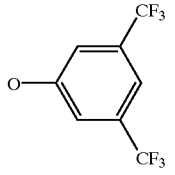 |
| 2.287 | $Q_{20}$ | — | i-$C_4H_9$ | — | H |  |
| 2.288 | $Q_{20}$ | — | i-$C_3H_7$ | — | $CH_3$ | 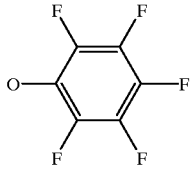 |
| 2.289 | $Q_{20}$ | — | $C_2H_5$ | — | $CH_3$ |  |

TABLE 2-continued
Compounds of the formula Ia:
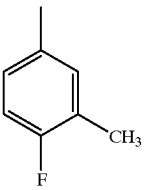
(Ia)
| Comp. No. | $Q_i$ | $R_{21}$ | $R_{22}$ | $R_{23}$ | $R_{24}$ | $XR_4$ |
|---|---|---|---|---|---|---|
| 2.290 | $Q_{20}$ | — | $NH_2$ | — | 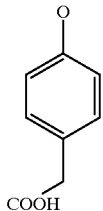 | 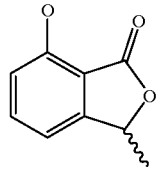 |
| 2.291 | $Q_{20}$ | — | $NH_2$ | — | 4-Cl—$C_6H_4$ | 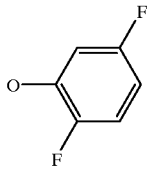 |
| 2.292 | $Q_{20}$ | — | $CH_3$ | — | $t$-$C_4H_9$ | 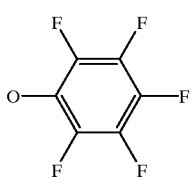 |
| 2.293 | $Q_{20}$ | — | $s$-$C_4H_9$ | — | H | 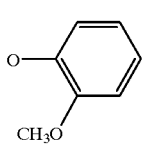 |
| 2.294 | $Q_{20}$ | — | $i$-$C_4H_9$ | — | $CH_3$ | O-$i$-$C_3H_7$ |
| 2.295 | $Q_{20}$ | — | $Si(CH_3)_3$ | — | H | 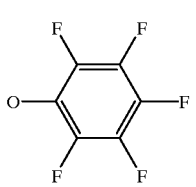 |
| 2.296 | $Q_{20}$ | — | $n$-$C_3H_7$ | — | H | O-$c$-$C_6H_{11}$ |
| 2.297 | $Q_{20}$ | — | $CH_3$ | — | $CH_3$ |  |

TABLE 2-continued
Compounds of the formula Ia:
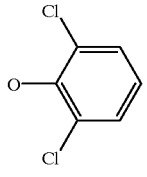
(Ia)
| Comp. No. | $Q_i$ | $R_{21}$ | $R_{22}$ | $R_{23}$ | $R_{24}$ | $XR_4$ |
|---|---|---|---|---|---|---|
| 2.298 | $Q_{20}$ | — | $OC_2H_5$ | — | H | 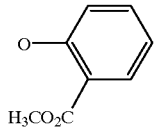 |
| 2.299 | $Q_{20}$ | — | $CH_3$ | — | CN | 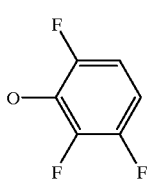 |
| 2.300 | $Q_{20}$ | — | H | — | $C_6H_5$ | 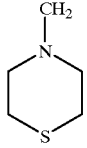 |
| 2.301 | $Q_{20}$ | — | $CH_3$ | — | 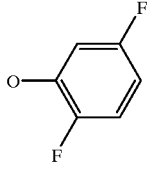 | 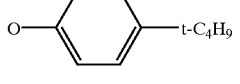 |
| 2.302 | $Q_{20}$ | — | $CH_3$ | — | 3-Pyridyl | 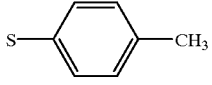 |
| 2.303 | $Q_{20}$ | — | $C_6H_5$ | — | $CONHCH_3$ | 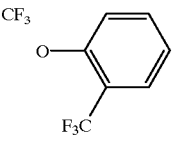 |
| 2.304 | $Q_{20}$ | — | $NHCOCH_3$ | — | $CF_3$ | 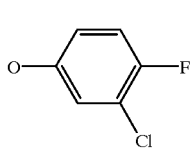 |
| 2.305 | $Q_{21}$ | H | — | — | $C_6H_5$ | |

TABLE 2-continued
Compounds of the formula Ia:
(Ia)
| Comp. No. | $Q_i$ | $R_{21}$ | $R_{22}$ | $R_{23}$ | $R_{24}$ | $XR_4$ |
|---|---|---|---|---|---|---|
| 2.306 | $Q_{21}$ | $CH_2OCH_3$ | — | — | $C_6H_5$ | 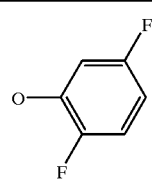 |
| 2.307 | $Q_{21}$ | $CH_3$ | — | — | 4-Cl—$C_6H_4$ | 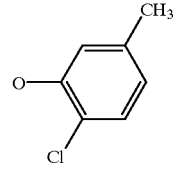 |
| 2.308 | $Q_{30}$ | — | — | $C_6H_5$ | — | 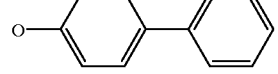 |
| 2.309 | $Q_{30}$ | — | — | n-$C_4H_9$ | — | 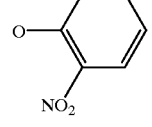 |
| 2.310 | $Q_{33}$ | $C_6H_5$ | — | — | — | 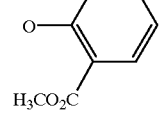 |
| 2.311 | $Q_{33}$ | t-$C_4H_9$ | — | — | — | 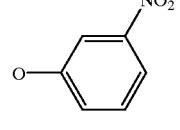 |
| 2.312 | $Q_{33}$ | i-$C_3H_7$ | — | — | — | 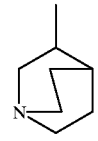 |
| 2.313 | $Q_{33}$ | $C_2H_5$ | — | — | — | 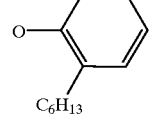 |

TABLE 2-continued

Compounds of the formula Ia:

(Ia)

| Comp. No. | $Q_i$ | $R_{21}$ | $R_{22}$ | $R_{23}$ | $R_{24}$ | $XR_4$ |
|---|---|---|---|---|---|---|
| 2.314 | $Q_{33}$ | $CH_3$ | — | — | — | 4-(pyridin-3-yl)phenoxy |
| 2.315 | $Q_{33}$ | $OCH_3$ | — | — | — | pentafluorophenoxy |
| 2.316 | $Q_{33}$ | $O\text{-}n\text{-}C_4H_9$ | — | — | — | 2-(trifluoromethyl)phenoxy |
| 2.317 | $Q_{33}$ | $N(C_2H_5)_2$ | — | — | — | pentafluorophenoxy |
| 2.318 | $Q_{33}$ | $SCH_3$ | — | — | — | naphthalen-1-yloxy |
| 2.319 | $Q_{33}$ | $S\text{-}c\text{-}C_6H_{11}$ | — | — | — | pentafluorophenoxy |
| 2.320 | $Q_{33}$ | 4-chlorophenylthio | — | — | — | $OC_8H_{17}$ |

TABLE 2-continued

Compounds of the formula Ia:

(Ia)

| Comp. No. | $Q_i$ | $R_{21}$ | $R_{22}$ | $R_{23}$ | $R_{24}$ | $XR_4$ |
|---|---|---|---|---|---|---|
| 2.321 | $Q_{33}$ | 4-Cl-C$_6$H$_4$-SO$_2$- | — | — | — | 2,6-dichlorophenoxy |
| 2.322 | $Q_{33}$ | 3-CF$_3$-C$_6$H$_4$-O- | — | — | — | 2,3,5,6-tetrafluorophenoxy |
| 2.323 | $Q_{39}$ | — | — | — | CH$_3$ | 1,3-benzodioxol-5-yloxy |
| 2.324 | $Q_{39}$ | — | — | — | C$_6$H$_5$ | 3,3,5,5-tetramethylcyclohexyloxy |
| 2.325 | $Q_{39}$ | — | — | — | n-C$_4$H$_9$ | 3-ethylphenoxy |
| 2.326 | $Q_4$ | H | H | OCH$_3$ | — | 2,3,4,5-tetrafluorophenoxy |

TABLE 2-continued
Compounds of the formula Ia:
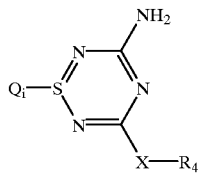
(Ia)
| Comp. No. | $Q_i$ | $R_{21}$ | $R_{22}$ | $R_{23}$ | $R_{24}$ | $XR_4$ |
|---|---|---|---|---|---|---|
| 2.327 | $Q_4$ | H | H | Cl | — | 2,5-difluorophenoxy |
| 2.328 | $Q_{20}$ | — | Cl | — | H | pentafluorophenoxy |
| 2.329 | $Q_{20}$ | — | O—CH$_2$CF$_3$ | — | H | 3,5-dimethylphenoxy |
| 2.330 | $Q_{20}$ | — | —CN | — | H | 2,5-dimethylphenoxy |
| 2.331 | $Q_{20}$ | — | 3,5-dimethylphenoxy | — | H | pentafluorophenoxy |
| 2.332 | $Q_{20}$ | — | 2,5-difluorophenoxy | — | H | 2,5-difluorophenoxy |

TABLE 2-continued

Compounds of the formula Ia:

(Ia)

| Comp. No. | $Q_i$ | $R_{21}$ | $R_{22}$ | $R_{23}$ | $R_{24}$ | $XR_4$ |
|---|---|---|---|---|---|---|
| 2.333 | $Q_{20}$ | — | pentafluorophenoxy | — | H | pentafluorophenoxy |
| 2.334 | $Q_{20}$ | — | Cl | — | H | $OCH_2CF_3$ |
| 2.335 | $Q_{20}$ | — | $OCH_2CF_3$ | — | H | $OCH_2CF_3$ |
| 2.336 | $Q_{20}$ | — | Cl | — | H | 3-(n-$C_3H_7$)phenoxy |
| 2.337 | $Q_2$ | $CH_3$ | —CH=C(CH$_3$)—C(N-pyrrolyl)=CH— | | — | 2,5-difluorophenoxy |

TABLE 3

Compounds of the formula Ib:

Ib

| Comp. No. | $Q_i$ | $R_{21}$ | $R_{22}$ | $R_{23}$ | $R_{24}$ | $XR_4$ |
|---|---|---|---|---|---|---|
| 3.001 | $Q_1$ | H | —CH=CH—CH=N— | | $CH_3$ | 2,6-dichlorophenoxy |

TABLE 3-continued
Compounds of the formula Ib:
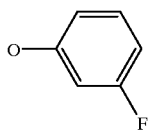
Ib
| Comp. No. | $Q_i$ | $R_{21}$ | $R_{22}$ | $R_{23}$ | $R_{24}$ | $XR_4$ |
|---|---|---|---|---|---|---|
| 3.002 | $Q_1$ | $CH_3$ | —C(Cl)=CH—CH=N— | | $COCH_3$ | 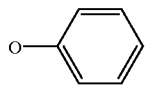 |
| 3.003 | $Q_1$ | | —S—CH=CH— | H | 4-$CH_3$—$C_6H_4$ | 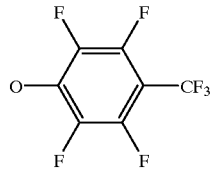 |
| 3.004 | $Q_1$ | | —CH=CH—S— | H | 4-$CH_3$—$C_6H_4$ | 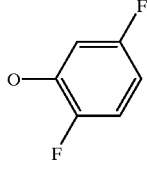 |
| 3.005 | $Q_2$ | H | $CH_3$ | H | — | 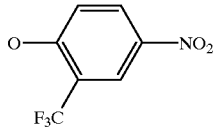 |
| 3.006 | $Q_2$ | H | H | H | — | 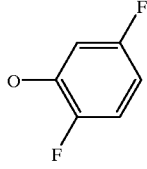 |
| 3.007 | $Q_2$ | H | H | —CH=$CHCH_3$ | — | 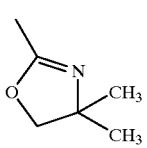 |
| 3.008 | $Q_2$ | 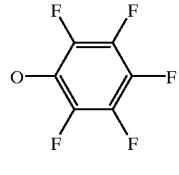 | H | H | — |  |

TABLE 3-continued
Compounds of the formula Ib:
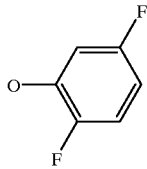
| Comp. No. | $Q_i$ | $R_{21}$ | $R_{22}$ | $R_{23}$ | $R_{24}$ | $XR_4$ |
|---|---|---|---|---|---|---|
| 3.009 | $Q_2$ | H | H | $SCH_3$ | — | 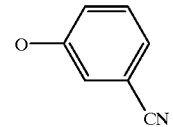 |
| 3.010 | $Q_2$ | H | H | $COOCH_3$ | — | 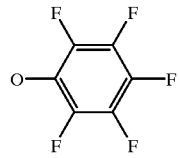 |
| 3.011 | $Q_2$ | H | H | —CH=OH$_2$ | — | 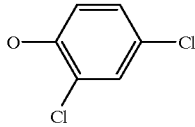 |
| 3.012 | $Q_2$ | H | —C(Cl)=CH—C(Cl)=CH— | | — | 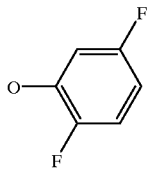 |
| 3.013 | $Q_2$ | H | H | $OCH_3$ | — | 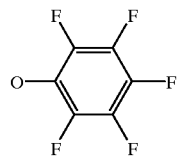 |
| 3.014 | $Q_2$ | H | H | Cl | — | 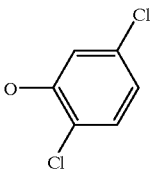 |
| 3.015 | $Q_2$ | H | —C(OCH$_3$)=CH—CH=CH— | | — |  |

TABLE 3-continued
Compounds of the formula Ib:
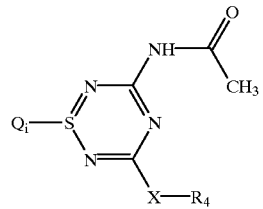
| Comp. No. | $Q_i$ | $R_{21}$ | $R_{22}$ | $R_{23}$ | $R_{24}$ | $XR_4$ |
|---|---|---|---|---|---|---|
| 3.016 | $Q_2$ | $CH_3$ | (structure: $H_3C$–C(=CH$_2$)–C(=CHCH$_3$)–C(O-i-C$_3$H$_7$)=CHCH$_3$) | | — | 2,3,6-trifluorophenoxy |
| 3.017 | $Q_2$ | H | —C(CH$_3$)=CH—CH=CH— | | — | 2,5-difluorophenoxy |
| 3.018 | $Q_2$ | H | —CH=CH—CH=C(CH$_3$)— | | — | 2,5-dimethylphenoxy |
| 3.019 | $Q_2$ | H | H | —C≡CH | — | pentafluorophenoxy |
| 3.020 | $Q_2$ | H | —CH=CH—CH=CH— | | — | pentafluorophenoxy |
| 3.021 | $Q_2$ | $CH_3$ | —CH=C(CH$_3$)—C(CH$_3$)=CH— | | — | 3,4,5-trimethoxyphenoxy |

TABLE 3-continued
Compounds of the formula Ib:
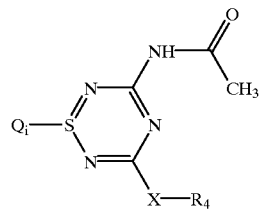
Ib
| Comp. No. | $Q_i$ | $R_{21}$ | $R_{22}$ | $R_{23}$ | $R_{24}$ | $XR_4$ |
|---|---|---|---|---|---|---|
| 3.022 | $Q_2$ | H | H | H | — | 2,5-difluorophenoxy |
| 3.023 | $Q_2$ | $CH_3$ | H | H | — | 2,5-difluorophenoxy |
| 3.024 | $Q_2$ | Cl | H | H | — | pentafluorophenoxy |
| 3.025 | $Q_2$ | H | H | n-$C_6H_{13}$ | — | phenoxy |
| 3.026 | $Q_2$ | H | H | $CH_3$ | — | 2,5-difluorophenoxy |
| 3.027 | $Q_2$ | —$CH_2$—$C(CH_3)$=$C(CH_3)$—$CH_2$— | | H | — | 2,5-dimethoxyphenoxy |
| 3.028 | $Q_2$ | H | $CH_3$ | H | — | 2,5-dichlorophenoxy |

TABLE 3-continued
Compounds of the formula Ib:
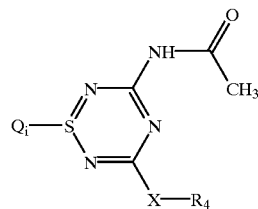
Ib
| Comp. No. | $Q_i$ | $R_{21}$ | $R_{22}$ | $R_{23}$ | $R_{24}$ | $XR_4$ |
|---|---|---|---|---|---|---|
| 3.029 | $Q_2$ | H | H | $SO_2CH_3$ | — | 2,5-difluorophenoxy |
| 3.030 | $Q_2$ | —CH=C(CH$_3$)—C(CH$_3$)=CH— | | H | — | 2-nitrophenoxy |
| 3.031 | $Q_2$ | H | H | $C_2H_5$ | — | 2,5-difluorophenoxy |
| 3.032 | $Q_2$ | H | H | H | — | pentafluorophenoxy |
| 3.033 | $Q_2$ | H | H | t-$C_4H_9$ | — | pentafluorophenoxy |
| 3.034 | $Q_2$ | H | H | n-$C_4H_9$ | — | 2,5-difluorophenoxy |
| 3.035 | $Q_2$ | H | H | I | — | 2,6-dichlorophenoxy |

TABLE 3-continued
Compounds of the formula Ib:
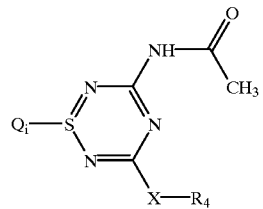
Ib
| Comp. No. | $Q_i$ | $R_{21}$ | $R_{22}$ | $R_{23}$ | $R_{24}$ | $XR_4$ |
|---|---|---|---|---|---|---|
| 3.036 | $Q_2$ | H | H | $SCH_3$ | — | 2,5-difluorophenoxy |
| 3.037 | $Q_2$ | H | —CH=CH—CH=CH— | | — | 2,5-difluorophenoxy |
| 3.038 | $Q_2$ | H | $CH_3$ | F | — | 2-methylphenoxy |
| 3.039 | $Q_2$ | $OCH_3$ | H | H | — | pentafluorophenoxy |
| 3.040 | $Q_3$ | H | H | — | $CH_3$ | 2-fluoropyridin-3-yloxy |
| 3.041 | $Q_3$ | H | H | — | $CON(C_2H_5)_2$ | 4-nitrophenoxy |
| 3.042 | $Q_3$ | H | H | — | Cl | pentafluorophenoxy |

TABLE 3-continued

Compounds of the formula Ib:

Ib

| Comp. No. | $Q_i$ | $R_{21}$ | $R_{22}$ | $R_{23}$ | $R_{24}$ | $XR_4$ |
|---|---|---|---|---|---|---|
| 3.043 | $Q_3$ | H | H | — | $CH_2OCH_3$ | 3-(n-butoxy)phenoxy |
| 3.044 | $Q_3$ | —CH=CH—CH=CH— | | — | $CON(C_2H_5)_2$ | |
| 3.045 | $Q_3$ | H | H | 2-methyl-4,4-dimethyl-oxazoline | — | pentafluorophenoxy |
| 3.046 | $Q_3$ | —CH=CH—CH=CH— | | — | $CH_2N(CH_3)_2$ | 4,6-dibromo-2-(methoxycarbonyl)pyridin-3-yloxy |
| 3.047 | $Q_3$ | —CH=CH—CH=CH— | | — | pyrrolidin-1-ylmethyl | 4-methylthiazol-2-yloxy |
| 3.048 | $Q_4$ | H | H | H | — | pentafluorophenoxy |
| 3.049 | $Q_4$ | H | —CH=CH—CH=CH— | | — | 5-chloro-2-nitrophenoxy |
| 3.050 | $Q_4$ | H | $CH_3$ | F | — | 2-methylphenoxy |

TABLE 3-continued
Compounds of the formula Ib:
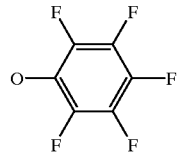
| Comp. No. | $Q_i$ | $R_{21}$ | $R_{22}$ | $R_{23}$ | $R_{24}$ | $XR_4$ |
|---|---|---|---|---|---|---|
| 3.051 | $Q_4$ | $OCH_3$ | H | H | — | 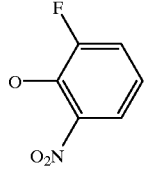 |
| 3.052 | $Q_4$ | H | —CH=CH—CH=CH— | | — | 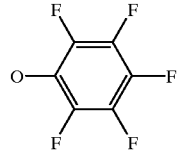 |
| 3.053 | $Q_4$ | H | H | $t\text{-}C_4H_9$ | — | 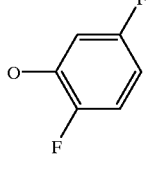 |
| 3.054 | $Q_4$ | H | H | $n\text{-}C_4H_9$ | — | 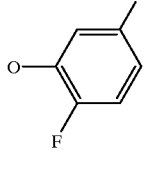 |
| 3.055 | $Q_4$ | H | H | H | — | 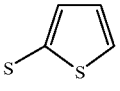 |
| 3.056 | $Q_4$ | H | H | $CH_3$ | — |  |
| 3.057 | $Q_4$ | $CH_3$ | H | H | — |  |

TABLE 3-continued
Compounds of the formula Ib:
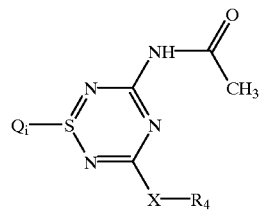
Ib
| Comp. No. | $Q_i$ | $R_{21}$ | $R_{22}$ | $R_{23}$ | $R_{24}$ | $XR_4$ |
|---|---|---|---|---|---|---|
| 3.058 | $Q_4$ | H | H | $C_2H_5$ | — | 2-(trifluoromethyl)-4-nitrophenoxy |
| 3.059 | $Q_4$ | Cl | H | H | — | pentafluorophenoxy |
| 3.060 | $Q_4$ | H | H | n-$C_6H_{13}$ | — | phenoxy |
| 3.061 | $Q_4$ | H | H | t-$C_4H_9$ | — | 2,5-difluorophenoxy |
| 3.062 | $Q_4$ | H | H | I | — | 2,6-dichlorophenoxy |
| 3.063 | $Q_4$ | H | H | 2-thienyl | — | 4-(ethoxycarbonyl)phenoxy |
| 3.064 | $Q_4$ | H | $CH_3$ | H | — | 2,5-dichlorophenoxy |

TABLE 3-continued
Compounds of the formula Ib:
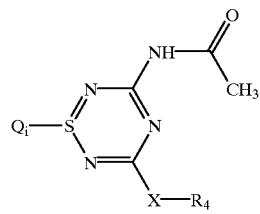
Ib
| Comp. No. | $Q_i$ | $R_{21}$ | $R_{22}$ | $R_{23}$ | $R_{24}$ | $XR_4$ |
|---|---|---|---|---|---|---|
| 3.065 | $Q_4$ | $CH_3$ | H | H | — | pentafluorophenoxy |
| 3.066 | $Q_4$ | —$CH_2$—$CH_2$—$CH_2$—$C(OCH_3)_2$— | | $SCH_3$ | — | 3-cyanophenoxy |
| 3.067 | $Q_4$ | H | H | $C_2H_5$ | — | 2,5-difluorophenoxy |
| 3.068 | $Q_4$ | H | =HC–N(4-methylphenyl)–CH— | | — | 3-(ethoxycarbonyl)phenoxy |
| 3.069 | $Q_4$ | H | H | $COCH_3$ | — | pentafluorophenoxy |
| 3.070 | $Q_4$ | $(CH_3)(H_2C)CH-CH(CH_3)(OC_3H_7)$ | | $SCH_3$ | — | 3-methyl-5-isopropylphenoxy |

TABLE 3-continued
Compounds of the formula Ib:
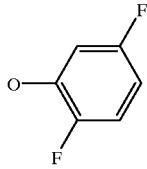
Ib
| Comp. No. | $Q_i$ | $R_{21}$ | $R_{22}$ | $R_{23}$ | $R_{24}$ | $XR_4$ |
|---|---|---|---|---|---|---|
| 3.071 | $Q_4$ | H | H | $CH_3$ | — | 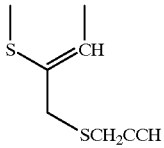 |
| 3.072 | $Q_4$ | H | 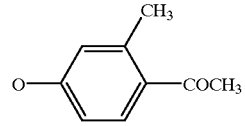 | | — | 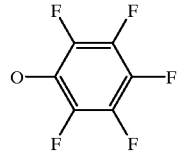 |
| 3.073 | $Q_4$ | H | —CH=CH—CH=CH— | | — | 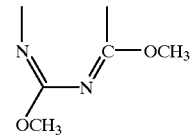 |
| 3.074 | $Q_4$ | $CH_3$ | —C($CH_3$)=C($SCH_3$)—S— | | — | $SC_6H_5$ |
| 3.075 | $Q_4$ | H | 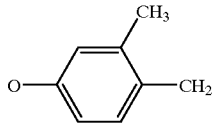 | | — | 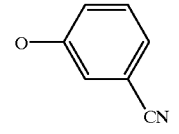 |
| 3.076 | $Q_4$ | H | H | $COOCH_3$ | — | 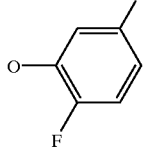 |
| 3.077 | $Q_4$ | H | H | 2-thienyl | — | 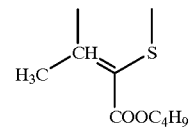 |
| 3.078 | $Q_4$ | $CH_3$ | 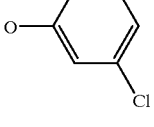 | | — |  |

TABLE 3-continued

Compounds of the formula Ib:

| Comp. No. | $Q_i$ | $R_{21}$ | $R_{22}$ | $R_{23}$ | $R_{24}$ | $XR_4$ |
|---|---|---|---|---|---|---|
| 3.079 | $Q_4$ | H | —CH=CH—CH=CH— | | — | 2,5-difluorophenoxy |
| 3.080 | $Q_4$ | H | H | —C≡CH | — | pentafluorophenoxy |
| 3.081 | $Q_4$ | $CH_3$ | —CH=N—CH=N— | | — | 2-formylphenoxy |
| 3.082 | $Q_4$ | $CH_3$ | —N=CH—N=CH— | | — | (2-oxobicyclo[4.2.0]octa-1,3,5-trien-1-yl)oxy |
| 3.083 | $Q_4$ | H | H | —CH=$CH_2$ | — | pentafluorophenoxy |
| 3.084 | $Q_4$ | H | H | $C_2H_5$ | — | pentafluorophenoxy |
| 3.085 | $Q_4$ | H | H | —CH=$CHCH_3$ | — | 2,5-difluorophenoxy |

TABLE 3-continued
Compounds of the formula Ib:
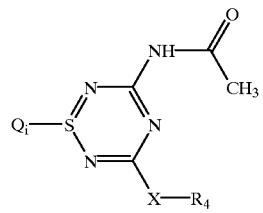
Ib
| Comp. No. | $Q_i$ | $R_{21}$ | $R_{22}$ | $R_{23}$ | $R_{24}$ | $XR_4$ |
|---|---|---|---|---|---|---|
| 3.086 | $Q_4$ | H | H | $CH_3$ | — | O–C6F5 (pentafluorophenoxy) |
| 3.087 | $Q_4$ | —$CH_2$—$C(CH_3)_2$—$CH$=$C(OCH_3)$— | | $SCH_3$ | — | $OCH_2CF_3$ |
| 3.088 | $Q_4$ | $CH_3$ | —$C(CH_3)$=$CH$—$S$— | | — | O–(3,4,5-trimethylphenyl) |
| 3.089 | $Q_4$ | H | H | n-$C_6H_{13}$ | — | O–(2,5-difluorophenyl) |
| 3.090 | $Q_4$ | H | H | $SO_2CH_3$ | — | O–(2,5-difluorophenyl) |
| 3.091 | $Q_4$ | H | H | n-$C_6H_{13}$ | — | O–C6F5 (pentafluorophenoxy) |
| 3.092 | $Q_4$ | H | $CH_3$ | H | — | O–(2,5-difluorophenyl) |

TABLE 3-continued
Compounds of the formula Ib:
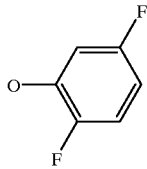
Ib
| Comp. No. | $Q_i$ | $R_{21}$ | $R_{22}$ | $R_{23}$ | $R_{24}$ | $XR_4$ |
|---|---|---|---|---|---|---|
| 3.093 | $Q_4$ | H | H | I | — | 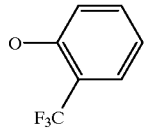 |
| 3.094 | $Q_4$ | H | —CH=CH—CH=C(CH$_3$)— | | — |  |
| 3.095 | $Q_4$ | —(CH$_2$)$_2$NH$_2$ | —CH=CH—C(OCH$_3$)=CH— | | — | 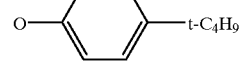 |
| 3.096 | $Q_4$ | —(CH$_2$)$_2$N(CH$_3$)$_2$ | —C(OCH$_3$)=CH—CH=CH— | | — |  |
| 3.097 | $Q_4$ | CH$_3$ | —CH=CF—CH=CH— | | — | OCH$_2$CF$_3$ |
| 3.098 | $Q_4$ | H | H | 2-thienyl | — | 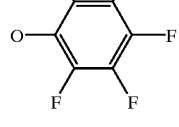 |
| 3.099 | $Q_4$ | OCH$_3$ | 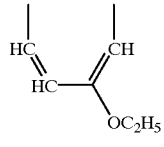 | | — | OC$_6$H$_5$ |
| 3.100 | $Q_4$ | H | H | SCH$_3$ | — |  |

TABLE 3-continued
Compounds of the formula Ib:
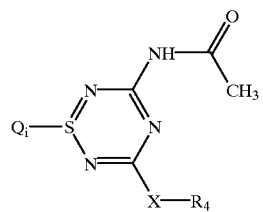
Ib
| Comp. No. | $Q_i$ | $R_{21}$ | $R_{22}$ | $R_{23}$ | $R_{24}$ | $XR_4$ |
|---|---|---|---|---|---|---|
| 3.101 | $Q_4$ | $CH_2CON(CH_3)_2$ | —CH=CH—C(OCH$_3$)=CH— | — | | 3-(N(C$_2$H$_5$)$_2$)-phenoxy |
| 3.102 | $Q_4$ | H | $CH_3$ | H | — | pentafluorophenoxy |
| 3.103 | $Q_4$ | H | H | $OCH_3$ | — | 2,5-difluorophenoxy |
| 3.104 | $Q_4$ | H | —C(OH)=CH—CH=CH— | | — | 2,6-dichlorophenoxy |
| 3.105 | $Q_4$ | H | H | $Sn(n-C_4H_9)_3$ | — | pentafluorophenoxy |
| 3.106 | $Q_4$ | $CH_3$ | —CH=CH—CH=CH— | | — | benzo[1,3]dioxol-5-yloxy |
| 3.107 | $Q_4$ | $CH_2CO_2H$ | —CH=CH—CH=CH— | | — | 3-(SC$_5$H$_{11}$)-phenoxy |

TABLE 3-continued

Compounds of the formula Ib:

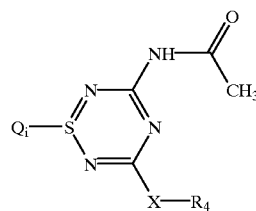

Ib

| Comp. No. | $Q_i$ | $R_{21}$ | $R_{22}$ | $R_{23}$ | $R_{24}$ | $XR_4$ |
|---|---|---|---|---|---|---|
| 3.108 | $Q_4$ | $CH_2CO_2C_2H_5$ | —CH=C(Cl)—CH=CH— | | — | 2,3,5,6-tetrafluorophenoxy |
| 3.109 | $Q_4$ | $CH_3$ | —CH=C(Cl)—CH=CH— | | — | pentafluorophenoxy |
| 3.110 | $Q_4$ | H | —CH=C($CH_3$)—CH=CH— | | — | 4-(trifluoromethyl)phenoxy |
| 3.111 | $Q_4$ | H | H | Cl | — | pentafluorophenoxy |
| 3.112 | $Q_4$ | $CH_3$ | —CH=C($CH_3$)—CH=CH— | | — | 2-ethylphenoxy |
| 3.113 | $Q_4$ | H | H | $n$-$C_4H_9$ | — | pentafluorophenoxy |
| 3.114 | $Q_5$ | H | H | $C_6H_5$ | — | 2,4-bis(trifluoromethyl)phenoxy |

TABLE 3-continued
Compounds of the formula Ib:
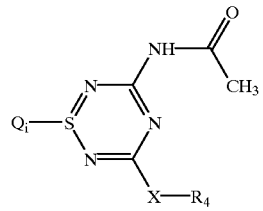
Ib
| Comp. No. | $Q_i$ | $R_{21}$ | $R_{22}$ | $R_{23}$ | $R_{24}$ | $XR_4$ |
|---|---|---|---|---|---|---|
| 3.115 | $Q_5$ | H | $CH_3$ | — | $C_6H_5$ | pentafluorophenoxy |
| 3.116 | $Q_5$ | H | $CH_3$ | — | $CH_2OCH_3$ | 2-naphthyloxy |
| 3.117 | $Q_5$ | $C_6H_5$ | $CH_3$ | — | $CON(CH_3)_2$ | 2,5-difluorophenoxy |
| 3.118 | $Q_5$ | —CH=CH—CH=CH— | | — | $CH_3$ | 2-fluoro-6-methylpyridin-3-yloxy |
| 3.119 | $Q_5$ | H | $C_2H_5$ | — | 2-Cl—$C_6H_4$ | 2-methylphenoxy |
| 3.120 | $Q_5$ | H | $CH_3$ | — | t-$C_4H_9$ | pentafluorophenoxy |
| 3.121 | $Q_5$ | H | $SCH_3$ | — | t-$C_4H_9$ | pentafluorophenoxy |

TABLE 3-continued
Compounds of the formula Ib:
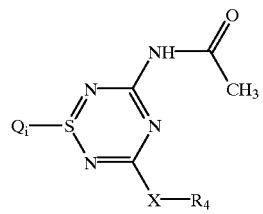
Ib
| Comp. No. | $Q_i$ | $R_{21}$ | $R_{22}$ | $R_{23}$ | $R_{24}$ | $XR_4$ |
|---|---|---|---|---|---|---|
| 3.122 | $Q_5$ | H | 2-Thiazolyl | — | $CH_3$ | 2,5-difluorophenoxy |
| 3.123 | $Q_5$ | $H_2C-CH(CH_3)-O-$ (isopropoxymethyl) | | — | $CH_3$ | 2,5-difluorophenoxy |
| 3.124 | $Q_5$ | H | 3-Cl—$C_6H_4$ | — | $CH_2OC_2H_5$ | 2,5-difluorophenoxy |
| 3.125 | $Q_5$ | H | $CF_3$ | — | $CH_3$ | 4-t-$C_4H_9$-phenoxy |
| 3.126 | $Q_5$ | H | $CH_3$ | — | $C_6H_5$ | 4-(CH$_2$CH$_2$COCH$_3$)-phenoxy |
| 3.127 | $Q_7$ | H | — | $C_6H_5$ | H | 2-$CF_3$-phenoxy |

TABLE 3-continued
Compounds of the formula Ib:
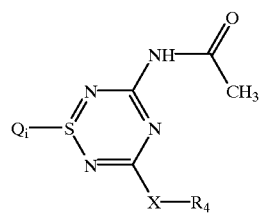
Ib
| Comp. No. | $Q_i$ | $R_{21}$ | $R_{22}$ | $R_{23}$ | $R_{24}$ | $XR_4$ |
|---|---|---|---|---|---|---|
| 3.128 | $Q_7$ | $C_6H_5$ | — | $CH_3$ | H | pentafluorophenoxy |
| 3.129 | $Q_7$ | H | — | $CH_3$ | $C_6H_5$ | 2,5-difluorophenoxy |
| 3.130 | $Q_7$ | H | — | $CH_3$ | $OCH_3$ | 4-(trifluoromethyl)phenoxy |
| 3.131 | $Q_7$ | $OCH_3$ | — | $CH_3$ | H | pentafluorophenoxy |
| 3.132 | $Q_7$ | $N(CH_3)_2$ | — | $t\text{-}C_4H_9$ | $CH_3$ | 2,5-difluorophenoxy |
| 3.133 | $Q_7$ | $CH_3$ | — | $t\text{-}C_4H_9$ | $N(CH_3)_2$ | 2,5-difluorophenoxy |
| 3.134 | $Q_8$ | — | H | H | $CH_2C_6H_5$ | 2,5-difluorophenoxy |

TABLE 3-continued
Compounds of the formula Ib:
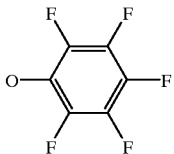
| Comp. No. | $Q_i$ | $R_{21}$ | $R_{22}$ | $R_{23}$ | $R_{24}$ | $XR_4$ |
|---|---|---|---|---|---|---|
| 3.135 | $Q_8$ | — | H | H | $SO_2C_6H_5$ | 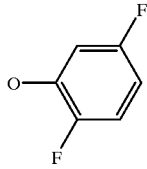 |
| 3.136 | $Q_8$ | — | H | H | $C_6H_5$ | 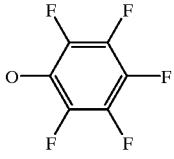 |
| 3.137 | $Q_8$ | — | H | H | $CH_3$ | 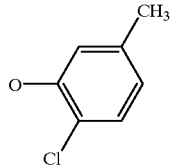 |
| 3.138 | $Q_8$ | — | —CH=CH—CH=CH— | | $n\text{-}C_3H_7$ | 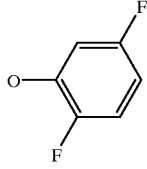 |
| 3.139 | $Q_8$ | — | Cl | Cl | $CH_2C_6H_5$ | 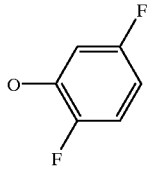 |
| 3.140 | $Q_8$ | — | $CH_3$ | $CH_3$ | $CH_2OCH_3$ | 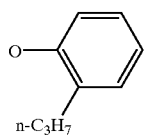 |
| 3.141 | $Q_8$ | — | —$CH_2$—$CH_2$—$CH_2$—$CH_2$— | | $CON(CH_3)_2$ |  |

TABLE 3-continued
Compounds of the formula Ib:
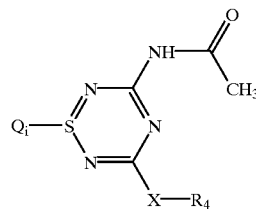
Ib
| Comp. No. | Q_i | R_{21} | R_{22} | R_{23} | R_{24} | XR_4 |
|---|---|---|---|---|---|---|
| 3.142 | $Q_{11}$ | — | —CH=C(CH_3)—CH=CH— | | — | 2,5-difluorophenoxy |
| 3.143 | $Q_{11}$ | — | —CH=CH—C(CH_3)=CH— | | — | 2-hexylphenoxy |
| 3.144 | $Q_{11}$ | — | —CH=CH—C(Cl)=CH— | | — | 7-oxy-3H-isobenzofuran-1-one-3-yl |
| 3.145 | $Q_{11}$ | — | —CH=CH—CH=CH— | | — | 2,5-difluorophenoxy |
| 3.146 | $Q_{11}$ | — | $C_6H_5$ | H | — | pentafluorophenoxy |
| 3.147 | $Q_{11}$ | — | 2-Cl—$C_6H_4$ | H | — | pentafluorophenoxy |
| 3.148 | $Q_{11}$ | — | 2-Furyl | H | — | 3-(trifluoromethyl)phenoxy |

TABLE 3-continued
Compounds of the formula Ib:
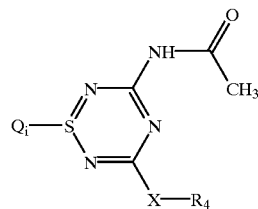
Ib
| Comp. No. | $Q_i$ | $R_{21}$ | $R_{22}$ | $R_{23}$ | $R_{24}$ | $XR_4$ |
|---|---|---|---|---|---|---|
| 3.149 | $Q_{11}$ | — | 2-Thienyl | H | — | 2,3,6-trifluorophenoxy |
| 3.150 | $Q_{11}$ | — | 4-$CF_3$—$C_6H_4$ | $CO_2C_2H_5$ | — | $OC_8H_{17}$ |
| 3.151 | $Q_{11}$ | — | $C_6H_5$ | $CO_2C_2H_5$ | — | pentafluorophenoxy |
| 3.152 | $Q_{11}$ | — | 2,4-Dichlorophenyl | $CO_2C_2H_5$ | — | 2,5-difluorophenoxy |
| 3.153 | $Q_{11}$ | — | 3-Cl—$C_6H_4$ | $CO_2C_2H_5$ | — | 3-methyl-5-isopropylphenoxy |
| 3.154 | $Q_{11}$ | — | t-$C_4H_9$ | $CO_2C_2H_5$ | — | pentafluorophenoxy |
| 3.155 | $Q_{13}$ | H | — | — | H | 4-butoxyphenoxy |
| 3.156 | $Q_{13}$ | $CH_3$ | — | — | $CH_3$ | 2-propylphenoxy |

TABLE 3-continued

Compounds of the formula Ib:

Ib

| Comp. No. | $Q_i$ | $R_{21}$ | $R_{22}$ | $R_{23}$ | $R_{24}$ | $XR_4$ |
|---|---|---|---|---|---|---|
| 3.157 | $Q_{13}$ | $C_6H_5$ | — | — | $CH_3$ | 3-pyridyl-S- |
| 3.158 | $Q_{13}$ | H | — | — | $CH_3$ | 2,5-difluorophenoxy |
| 3.159 | $Q_{13}$ | H | — | — | 2-Thienyl | 2-methylphenoxy |
| 3.160 | $Q_{13}$ | $CH_3$ | — | — | $CON(CH_3)_2$ | 2-(ethylsulfinyl)phenoxy |
| 3.161 | $Q_{13}$ | $CH_3$ | — | — | $CH_2OC_2H_5$ | 4-(2-carboxyethyl)phenoxy |
| 3.162 | $Q_{13}$ | H | — | — | $HC(OCH_3)C_3H_7$ | 2,5-difluorophenoxy |
| 3.163 | $Q_{13}$ | 2,6-dimethyl-4-methoxyphenyl | — | — | $CH_3$ | pentafluorophenoxy |

TABLE 3-continued
Compounds of the formula Ib:
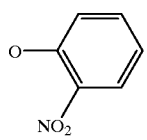
| Comp. No. | $Q_i$ | $R_{21}$ | $R_{22}$ | $R_{23}$ | $R_{24}$ | $XR_4$ |
|---|---|---|---|---|---|---|
| 3.164 | $Q_{13}$ | $C_6H_5$ | — | — | 2-Furyl | 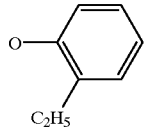 |
| 3.165 | $Q_{13}$ | $C_6H_5$ | — | — | 2,4-Dichlorophenyl | 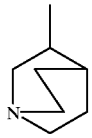 |
| 3.166 | $Q_{13}$ | $CH_3$ | — | — | 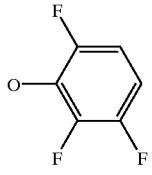 | 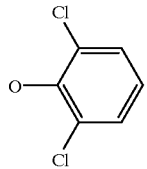 |
| 3.167 | $Q_{13}$ | $(CH_2)_5Cl$ | — | — | $CH_2OCH_3$ | 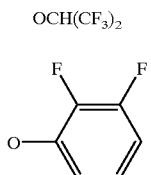 |
| 3.168 | $Q_{13}$ | $N(CH_3)C_6H_5$ | — | — | $t\text{-}C_4H_9$ | $OCH(CF_3)_2$ |
| 3.169 | $Q_{13}$ | 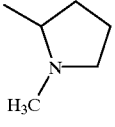 | — | — | $CH_3$ | 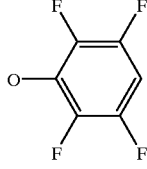 |
| 3.170 | $Q_{13}$ | $CH_3$ | — | — | 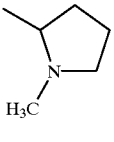 | 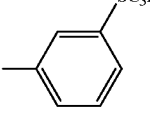 |
| 3.171 | $Q_{13}$ | $CH_3$ | — | — | $CF_3$ | $OCH_2C_7F_{15}$ |
| 3.172 | $Q_{16}$ | $OC_2H_5$ | — | $CH_3$ | — | 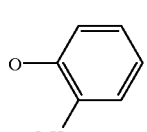 |

TABLE 3-continued

Compounds of the formula Ib:

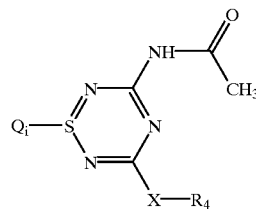

Ib

| Comp. No. | $Q_i$ | $R_{21}$ | $R_{22}$ | $R_{23}$ | $R_{24}$ | $XR_4$ |
|---|---|---|---|---|---|---|
| 3.173 | $Q_{16}$ | $OCH_3$ | — | $t\text{-}C_4H_9$ | — | ![pentafluorophenoxy] |
| 3.174 | $Q_{17}$ | — | H | H | — | $S\text{-}i\text{-}C_3H_7$ |
| 3.175 | $Q_{17}$ | — | H | $CH_3$ | — | $OCH(CF_3)_2$ |
| 3.176 | $Q_{17}$ | — | H | $C_6H_5$ | — | $OCH_2C_6F_5$ |
| 3.177 | $Q_{17}$ | — | H | CN | — | $OC_6H_5$ |
| 3.178 | $Q_{17}$ | — | —CH=CH—CH=CH— | | — | ![4-(trifluoromethyl)phenoxy] |
| 3.179 | $Q_{17}$ | — | —CF=CH—CH=CH— | | — | ![benzodioxole-oxy] |
| 3.180 | $Q_{17}$ | — | —CH=CH—CH=CF— | | — | ![naphthyloxy] |
| 3.181 | $Q_{17}$ | — | —CH=CH—CCl=CH— | | — | ![2-cyanophenoxy] |
| 3.182 | $Q_{17}$ | — | —CH=CH—CH=CH— | | — | ![pentafluorophenoxy] |
| 3.183 | $Q_{17}$ | — | $CH_3$ | H | — | ![2,4,6-trichlorophenoxy] |

TABLE 3-continued
Compounds of the formula Ib:
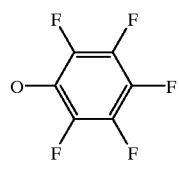
| Comp. No. | $Q_i$ | $R_{21}$ | $R_{22}$ | $R_{23}$ | $R_{24}$ | $XR_4$ |
|---|---|---|---|---|---|---|
| 3.184 | $Q_{18}$ | $CH_2C_6H_5$ | H | — | — | 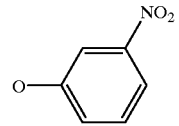 |
| 3.185 | $Q_{18}$ | —CH=CH—CH=CH— | | — | — | 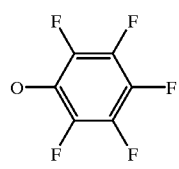 |
| 3.186 | $Q_{18}$ | H | H | — | — |  |
| 3.187 | $Q_{18}$ | H | $CH_3$ | — | — | 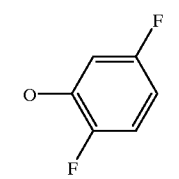 |
| 3.188 | $Q_{18}$ | $CON(C_2H_5)_2$ | H | — | — | 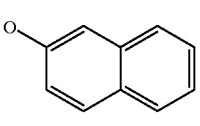 |
| 3.189 | $Q_{18}$ | $C_6H_5$ | $SCH_3$ | — | — | 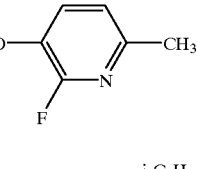 |
| 3.190 | $Q_{18}$ | 4-Tolyl | $SCH_3$ | — | — | 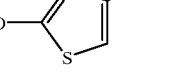 |
| 3.191 | $Q_{18}$ | —$CH_2$—$(CH_2)_3$—$CH_2$— | | — | — |  |

TABLE 3-continued

Compounds of the formula Ib:

| Comp. No. | $Q_i$ | $R_{21}$ | $R_{22}$ | $R_{23}$ | $R_{24}$ | $XR_4$ |
|---|---|---|---|---|---|---|
| 3.192 | $Q_{18}$ | H | O-i-$C_3H_7$ | — | — | 2-ethylphenoxy |
| 3.193 | $Q_{18}$ | $CH_3$ | 4-Tolyl | — | — | 2,5-difluorophenoxy |
| 3.194 | $Q_{18}$ | H | 2-Tolyl | — | — | 2-thienylthio |
| 3.195 | $Q_{18}$ | 4-Cl—$C_6H_4$ | H | — | — | 2-naphthyloxy |
| 3.196 | $Q_{18}$ | —CH=CH—S— | | — | — | pentafluorophenoxy |
| 3.197 | $Q_{18}$ | 4-Cl—$C_6H_4$ | $CON(CH_3)_2$ | — | — | 2-naphthyloxy |
| 3.198 | $Q_{18}$ | —S—CH=CH— | | — | — | 2-methylphenoxy |
| 3.199 | $Q_{18}$ | H | 4-Cl—$C_6H_4$ | — | — | 2,3,5,6-tetrafluorophenoxy |

TABLE 3-continued
Compounds of the formula Ib:
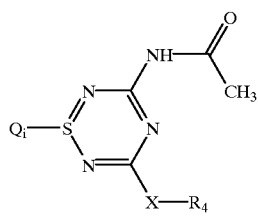
Ib
| Comp. No. | $Q_i$ | $R_{21}$ | $R_{22}$ | $R_{23}$ | $R_{24}$ | $XR_4$ |
|---|---|---|---|---|---|---|
| 3.200 | $Q_{20}$ | — | $CH_3$ | — | $CH_3$ | O-C6H4-CF3 (4-CF3) |
| 3.201 | $Q_{20}$ | — | i-$C_4H_9$ | — | H | O-C6H3-(CF3)2 (3,5-diCF3) |
| 3.202 | $Q_{20}$ | — | i-$C_3H_7$ | — | $CH_3$ | O-C6H3-F2 (2,5-diF) |
| 3.203 | $Q_{20}$ | — | $C_2H_5$ | — | $CH_3$ | O-C6F5 |
| 3.204 | $Q_{20}$ | — | $CH_3$ | — | t-$C_4H_9$ | O-C6H3-F2 (2,5-diF) |
| 3.205 | $Q_{20}$ | — | $CH_3$ | — | $CH_3$ | O-C6F5 |
| 3.206 | $Q_{20}$ | — | $OC_2H_5$ | — | H | O-C6H3-Cl2 (2,6-diCl) |

TABLE 3-continued
Compounds of the formula Ib:
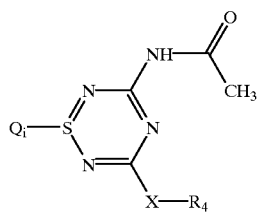
Ib
| Comp. No. | $Q_i$ | $R_{21}$ | $R_{22}$ | $R_{23}$ | $R_{24}$ | $XR_4$ |
|---|---|---|---|---|---|---|
| 3.207 | $Q_{20}$ | — | $CH_3$ | — | CN | 2-($H_3CO_2C$)-phenoxy |
| 3.208 | $Q_{20}$ | — | H | — | $C_6H_5$ | 2,3,6-trifluorophenoxy |
| 3.209 | $Q_{20}$ | — | $CH_3$ | — | 3-Pyridyl | 4-($t$-$C_4H_9$)-phenoxy |
| 3.210 | $Q_{20}$ | — | $C_6H_5$ | — | $CONHCH_3$ | 4-($CH_3$)-phenylthio |
| 3.211 | $Q_{21}$ | H | — | — | $C_6H_5$ | 3-Cl-4-F-phenoxy |
| 3.212 | $Q_{21}$ | $CH_2OCH_3$ | — | — | $C_6H_5$ | 2,5-difluorophenoxy |
| 3.213 | $Q_{21}$ | $CH_3$ | — | — | 4-Cl—$C_6H_4$ | 2-Cl-5-$CH_3$-phenoxy |
| 3.214 | $Q_{30}$ | — | — | $C_6H_5$ | — | 4-phenylphenoxy |

TABLE 3-continued
Compounds of the formula Ib:
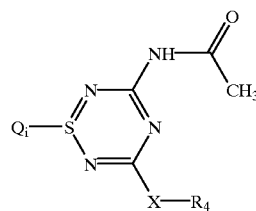
Ib
| Comp. No. | $Q_i$ | $R_{21}$ | $R_{22}$ | $R_{23}$ | $R_{24}$ | $XR_4$ |
|---|---|---|---|---|---|---|
| 3.215 | $Q_{30}$ | — | — | n-$C_4H_9$ | — | 2-nitrophenoxy |
| 3.216 | $Q_{33}$ | $C_6H_5$ | — | — | — | 2-(methoxycarbonyl)phenoxy |
| 3.217 | $Q_{33}$ | t-$C_4H_9$ | — | — | — | 3-nitrophenoxy |
| 3.218 | $Q_{33}$ | i-$C_3H_7$ | — | — | — | 2,4,6-trichlorophenoxy |
| 3.219 | $Q_{33}$ | $C_2H_5$ | — | — | — | 2-hexylphenoxy |
| 3.220 | $Q_{33}$ | $OCH_3$ | — | — | — | pentafluorophenoxy |
| 3.221 | $Q_{33}$ | O-n-$C_4H_9$ | — | — | — | 2-(trifluoromethyl)phenoxy |

TABLE 3-continued
Compounds of the formula Ib:
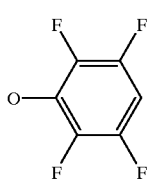
| Comp. No. | $Q_i$ | $R_{21}$ | $R_{22}$ | $R_{23}$ | $R_{24}$ | $XR_4$ |
|---|---|---|---|---|---|---|
| 3.222 | $Q_{33}$ | $N(C_2H_5)_2$ | — | — | — | 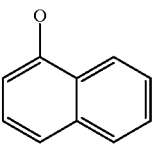 |
| 3.223 | $Q_{33}$ | $SCH_3$ | — | — | — | 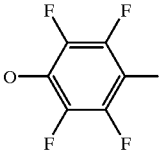 |
| 3.224 | $Q_{33}$ | $S\text{-}c\text{-}C_6H_{11}$ | — | — | — | 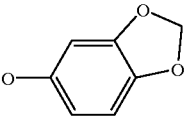 |
| 3.225 | $Q_{39}$ | — | — | — | $CH_3$ | 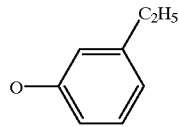 |
| 3.226 | $Q_{39}$ | — | — | — | $n\text{-}C_4H_9$ | 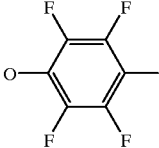 |
| 3.327 | $Q_{20}$ | — | Cl | — | H | 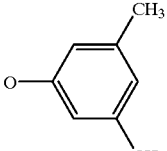 |
| 3.328 | $Q_{20}$ | — | $O\text{—}CH_2CF_3$ | — | H | |

TABLE 3-continued
Compounds of the formula Ib:
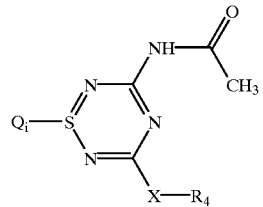
Ib
| Comp. No. | $Q_i$ | $R_{21}$ | $R_{22}$ | $R_{23}$ | $R_{24}$ | $XR_4$ |
|---|---|---|---|---|---|---|
| 3.329 | $Q_{20}$ | — | —CN | — | H | 2,5-dimethylphenoxy |
| 3.330 | $Q_{20}$ | — | 3,5-dimethylphenyl | — | H | pentafluorophenoxy |
| 3.331 | $Q_{20}$ | — | 2,5-difluorophenyl | — | H | 2,5-difluorophenoxy |
| 3.332 | $Q_{20}$ | — | pentafluorophenyl | — | H | pentafluorophenoxy |
| 3.333 | $Q_{20}$ | — | Cl | — | H | $OCH_2CF_3$ |
| 3.334 | $Q_{20}$ | — | $OCH_2CF_3$ | — | H | $OCH_2CF_3$ |
| 3.335 | $Q_{20}$ | — | Cl | — | H | 3-(n-propyl)phenoxy |

TABLE 4

$$\text{H}_3\text{C}-\underset{|}{\text{CH}}=\underset{|}{\text{C}}-\text{S}-\text{CH}_3$$
$$\text{CH}_3 \quad \text{COOC}_4\text{H}_9$$

| Comp. No. | $Q_i$ | $R_{21}$ | $R_{22}$ | $R_{23}$ | $R_{24}$ |
|---|---|---|---|---|---|
| 4.001 | $Q_1$ | H | —CH=CH—CH=N— | | $CH_3$ |
| 4.002 | $Q_1$ | $CH_3$ | —C(Cl)=CH—CH=N— | | $COCH_3$ |
| 4.003 | $Q_1$ | —S—CH=CH— | | H | 4-$CH_3$—$C_6H_4$ |
| 4.004 | $Q_1$ | —CH=CH—S— | | H | 4-$CH_3$—$C_6H_4$ |
| 4.005 | $Q_2$ | H | $CH_3$ | H | — |
| 4.006 | $Q_2$ | H | H | H | — |
| 4.007 | $Q_2$ | H | H | —CH=CHCH$_3$ | — |
| 4.008 | $Q_2$ | H | —CH=CH—CH=CH— | | — |
| 4.009 | $Q_2$ | (2-methyl-4,4-dimethyl-4,5-dihydrooxazol-yl) | H | H | — |
| 4.010 | $Q_2$ | H | H | $SCH_3$ | — |
| 4.011 | $Q_2$ | H | H | $COOCH_3$ | — |
| 4.012 | $Q_2$ | H | H | —CH=CH$_2$ | — |
| 4.013 | $Q_2$ | H | H | $S(O)CH_3$ | — |
| 4.014 | $Q_2$ | H | H | $Si(CH_3)_3$ | — |
| 4.015 | $Q_2$ | H | —C(Cl)=CH—C(Cl)=CH— | | — |
| 4.016 | $Q_2$ | H | H | $COCH_3$ | — |
| 4.017 | $Q_2$ | H | H | $OCH_3$ | — |
| 4.018 | $Q_2$ | H | H | Cl | — |
| 4.019 | $Q_2$ | H | —C(OCH$_3$)=CH—CH=CH— | | — |
| 4.020 | $Q_2$ | $CH_3$ | (substituted diene group with O-i-$C_3H_7$) | | — |
| 4.021 | $Q_2$ | H | —C(CH$_3$)=CH—CH=CH— | | — |
| 4.022 | $Q_2$ | H | —CH=CH—CH=C(CH$_3$)— | | — |
| 4.023 | $Q_2$ | H | H | —C≡CH | — |
| 4.024 | $Q_2$ | OH | —CH=CH—CH=CH— | | — |
| 4.025 | $Q_2$ | $CH_3$ | —CH=C(CH$_3$)—C(CH$_3$)=CH— | | — |
| 4.026 | $Q_2$ | $CH_3$ | H | H | — |
| 4.027 | $Q_2$ | H | H | $C_2H_5$ | — |
| 4.028 | $Q_2$ | Cl | H | H | — |
| 4.029 | $Q_2$ | H | H | n-$C_6H_{13}$ | — |
| 4.030 | $Q_2$ | H | H | $CH_3$ | — |
| 4.031 | $Q_2$ | —CH$_2$—C(CH$_3$)=C(CH$_3$)—CH$_2$— | | H | — |
| 4.032 | $Q_2$ | H | H | Sn(n-$C_4H_9$)$_3$ | — |
| 4.033 | $Q_2$ | H | H | $SO_2CH_3$ | — |
| 4.034 | $Q_2$ | H | H | t-$C_4H_9$ | — |
| 4.035 | $Q_2$ | H | H | n-$C_4H_9$ | — |
| 4.036 | $Q_2$ | H | H | I | — |
| 4.037 | $Q_2$ | H | H | B(OH)$_2$ | — |
| 4.038 | $Q_2$ | H | —CO—NH—CH=CH— | | — |
| 4.039 | $Q_2$ | H | $CH_3$ | F | — |
| 4.040 | $Q_2$ | $OCH_3$ | H | H | — |
| 4.041 | $Q_3$ | H | H | — | $CH_3$ |
| 4.042 | $Q_3$ | H | H | — | CON($C_2H_5$)$_2$ |
| 4.043 | $Q_3$ | H | H | — | Cl |
| 4.044 | $Q_3$ | H | H | — | $OCH_3$ |
| 4.045 | $Q_3$ | H | $Si(CH_3)_3$ | — | CON($C_2H_5$)$_2$ |
| 4.046 | $Q_3$ | H | H | — | $CH_2OCH_3$ |
| 4.047 | $Q_3$ | —CH=CH—CH=CH— | | — | CON($C_2H_5$)$_2$ |
| 4.048 | $Q_3$ | CONH-t-$C_4H_9$ | $CH_3$ | — | $CH_3$ |

TABLE 4-continued

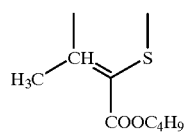

| Comp. No. | $Q_i$ | $R_{21}$ | $R_{22}$ | $R_{23}$ | $R_{24}$ |
|---|---|---|---|---|---|
| 4.049 | $Q_2$ | H | H | 2-methyl-4,4-dimethyl-oxazoline | — |
| 4.050 | $Q_3$ | —CH=CH—CH=CH— | | — | $CH_2N(CH_3)_2$ |
| 4.051 | $Q_3$ | —CH=CH—CH=CH— | | — | $H_2$C-pyrrolidinyl |
| 4.052 | $Q_4$ | H | H | H | — |
| 4.053 | $Q_4$ | H | —CH=CH—CH=CH— | | — |
| 4.054 | $Q_4$ | H | $CH_3$ | F | — |
| 4.055 | $Q_4$ | $OCH_3$ | H | H | — |
| 4.056 | $Q_4$ | H | H | $t\text{-}C_4H_9$ | — |
| 4.057 | $Q_4$ | H | H | $n\text{-}C_4H_9$ | — |
| 4.058 | $Q_4$ | H | H | $CH_3$ | — |
| 4.059 | $Q_4$ | $CH_3$ | H | H | — |
| 4.060 | $Q_4$ | H | H | $C_2H_5$ | — |
| 4.061 | $Q_4$ | Cl | H | H | — |
| 4.062 | $Q_4$ | H | H | $n\text{-}C_6H_{13}$ | — |
| 4.063 | $Q_4$ | H | H | $Si(CH_3)_3$ | — |
| 4.064 | $Q_4$ | H | H | $Sn(n\text{-}C_4H_9)_3$ | — |
| 4.065 | $Q_4$ | H | H | I | — |
| 4.066 | $Q_4$ | H | H | $B(OH)_2$ | — |
| 4.067 | $Q_4$ | H | H | 2-thienyl | — |
| 4.068 | $Q_4$ | H | $CH_3$ | H | — |
| 4.069 | $Q_4$ | —$CH_2$—$CH_2$—$CH_2$—$C(OCH_3)_2$— | | $SCH_3$ | — |
| 4.070 | $Q_4$ | H | =HC–N(p-tolyl)–CH— | | — |
| 4.071 | $Q_4$ | H | H | $COCH_3$ | — |
| 4.072 | $Q_4$ | | $H_2C$-CH(CH_3)-CH(CH_3)-CH_2-OC_3H_7 | $SCH_3$ | — |
| 4.073 | $Q_4$ | H | S–C=CH–CH(CH_3)-SCH_2CCH | | — |
| 4.074 | $Q_4$ | $CH_3$ | —C(CH_3)=C(SCH_3)—S— | | — |

TABLE 4-continued $$\underset{H_3C}{\overset{CH_3}{\diagdown}}CH=\underset{COOC_4H_9}{\overset{SCH_3}{\diagup}}$$

| Comp. No. | $Q_i$ | $R_{21}$ | $R_{22}$ | $R_{23}$ | $R_{24}$ |
|---|---|---|---|---|---|
| 4.075 | $Q_4$ | H | [structure: $CH_3-N=C(OCH_3)-N=C(CH_3)-OCH_3$] | | — |
| 4.076 | $Q_4$ | H | H | $COOCH_3$ | — |
| 4.077 | $Q_4$ | $CH_3$ | [structure: $H_3C-CH=C(SCH_3)-COOC_4H_9$] | | — |
| 4.078 | $Q_4$ | H | —S—CH=CH— | | — |
| 4.079 | $Q_4$ | H | H | —C≡CH | — |
| 4.080 | $Q_4$ | $CH_3$ | —CH=N—CH=N— | | — |
| 4.081 | $Q_4$ | $CH_3$ | —N=CH—N=CH— | | — |
| 4.082 | $Q_4$ | $CH_3$ | [structure: $H-N(CH_3)-CH=N-C(CH_3)=N(CH_3)(CH_2CH_2OH)$] | | — |
| 4.083 | $Q_4$ | H | H | —CH=$CH_2$ | — |
| 4.084 | $Q_4$ | H | [structure: $CH_3-S-C(=CH-CH_3)-C(=O)-O-t-C_4H_9$] | | — |
| 4.085 | $Q_4$ | H | [structure: $CH_3-N=C(CF_3)-N=C(CH_3)-OCH_3$] | | — |
| 4.086 | $Q_4$ | H | H | —CH=$CHCH_3$ | — |
| 4.087 | $Q_4$ | H | [structure: $CH_3O-C(=C(CH_3)(OCH_3))-C(=O)-NHC_2H_5$] | | — |
| 4.088 | $Q_4$ | $C_6H_5$ | [structure: $i-C_3H_7-S-C(CH_3)=N-CH=N-CH_3$] | | — |
| 4.089 | $Q_4$ | —$CH_2$—C($CH_3)_2$—CH=C($OCH_3$)— | | $SCH_3$ | — |
| 4.090 | $Q_4$ | $CH_3$ | —C($CH_3$)=CH—S— | | — |

TABLE 4-continued

| Comp. No. | $Q_i$ | $R_{21}$ | $R_{22}$ | $R_{23}$ | $R_{24}$ |
|---|---|---|---|---|---|
| 4.091 | $Q_4$ | $CH_3$ | | | — |
| 4.092 | $Q_4$ | H | H | $SO_2CH_3$ | — |
| 4.093 | $Q_4$ | $CH_3$ | | | — |
| 4.094 | $Q_4$ | $Si(CH_3)_3$ | H | H | — |
| 4.095 | $Q_4$ | $CH_3$ | | | — |
| 4.096 | $Q_4$ | $CH_3$ | | | — |
| 4.097 | $Q_4$ | H | | | — |
| 4.098 | $Q_4$ | $CH_3$ | | | — |
| 4.099 | $Q_4$ | $CH_3$ | | | — |

TABLE 4-continued
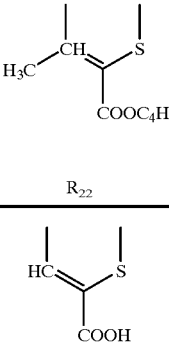
| Comp. No. | $Q_i$ | $R_{21}$ | $R_{22}$ | $R_{23}$ | $R_{24}$ |
|---|---|---|---|---|---|
| 4.100 | $Q_4$ | H | 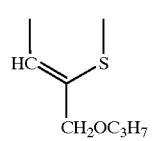 | — | |
| 4.101 | $Q_4$ | H | 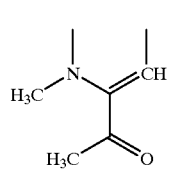 | — | |
| 4.102 | $Q_4$ | H | 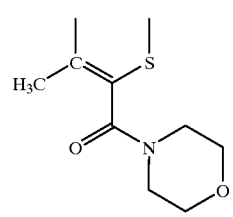 | — | |
| 4.103 | $Q_4$ | H | 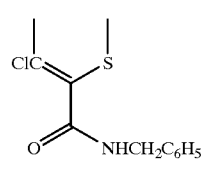 | — | |
| 4.104 | $Q_4$ | H | 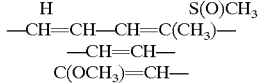 | — | |
| 4.105 | $Q_4$ | H | H | $S(O)CH_3$ | — |
| 4.106 | $Q_4$ | H | —CH=CH—CH=C($CH_3$)— | | — |
| 4.107 | $Q_4$ | —$(CH_2)_2NH_2$ | —CH=CH— | C(OCH_3)=CH— | — |
| 4.108 | $Q_4$ | —$(CH_2)_2N(CH_3)_2$ | —C($OCH_3$)=CH— | CH=CH— | — |
| 4.109 | $Q_4$ | —$(CH_2)_2OH$ | —CH=CH—CH=CH— | | — |
| 4.110 | $Q_4$ | —$CH_2SH$ | —CH=CH—CH=CH— | | — |
| 4.111 | $Q_4$ | $CH_3$ | —CH=CF—CH=CH— | | — |
| 4.112 | $Q_4$ | H | 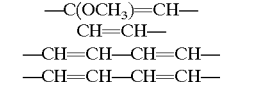 | — | |
| 4.113 | $Q_4$ | $OCH_3$ | 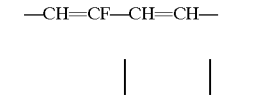 | — | |

TABLE 4-continued $$\underset{H_3C}{\overset{|}{C}H}=\underset{COOC_4H_9}{\overset{|}{C}}S$$

| Comp. No. | $Q_i$ | $R_{21}$ | $R_{22}$ | $R_{23}$ | $R_{24}$ |
|---|---|---|---|---|---|
| 4.114 | $Q_4$ | H | H | $SCH_3$ | — |
| 4.115 | $Q_4$ | H | H | $Sn(CH_3)_3$ | — |
| 4.116 | $Q_4$ | $CH_2CON(CH_3)_2$ | —CH=CH—C($OCH_3$)=CH— | | — |
| 4.117 | $Q_4$ | H | $CH_3$ | H | — |
| 4.118 | $Q_4$ | H | H | $OCH_3$ | — |
| 4.119 | $Q_4$ | H | —C(OH)=CH—CH=CH— | | — |
| 4.120 | $Q_4$ | $CH_3$ | —CH=CH—CH=CH— | | — |
| 4.121 | $Q_4$ | $CH_2CO_2H$ | —CH=CH—CH=CH— | | — |
| 4.122 | $Q_4$ | $CH_2CO_2C_2H_5$ | —CH=C(Cl)—CH=CH— | | — |
| 4.123 | $Q_4$ | $CH_3$ | —CH=C(Cl)—CH=CH— | | — |
| 4.124 | $Q_4$ | H | —CH=C($CH_3$)—CH=CH— | | — |
| 4.125 | $Q_4$ | H | H | Cl | — |
| 4.126 | $Q_4$ | $CH_3$ | —CH=C($CH_3$)—CH=CH— | | — |
| 4.127 | $Q_4$ | H | $Si(CH_3)_3$ | H | — |
| 4.128 | $Q_4$ | $CH_2N(CH_3)_2$ | —CH=CH—CH=CH— | | — |
| 4.129 | $Q_4$ | $CH_2$—N(morpholino) | —CH=CH—CH=CH— | | — |
| 4.130 | $Q_5$ | H | H | — | $C_6H_5$ |
| 4.131 | $Q_5$ | H | $CH_3$ | — | $C_6H_5$ |
| 4.132 | $Q_5$ | H | $CH_3$ | — | $CH_2OCH_3$ |
| 4.133 | $Q_5$ | $C_6H_5$ | $CH_3$ | — | $CON(CH_3)_2$ |
| 4.134 | $Q_5$ | —CH=CH—CH=CH— | | — | $CH_3$ |
| 4.135 | $Q_5$ | H | $C_2H_5$ | — | 2-Cl—$C_6H_4$ |
| 4.136 | $Q_5$ | H | $C(OCH_3)_3$ | — | $i$-$C_3H_7$ |
| 4.137 | $Q_5$ | H | $CH_3$ | — | $t$-$C_4H_9$ |
| 4.138 | $Q_5$ | H | $SCH_3$ | — | $t$-$C_4H_9$ |
| 4.139 | $Q_5$ | H | 2-Thiazolyl | — | $CH_3$ |
| 4.140 | $Q_5$ | $H_2C$—O—CH(CH_3)(iPr) | | — | $CH_3$ |
| 4.141 | $Q_5$ | H | 3-Cl—$C_6H_4$ | — | $CH_2OC_2H_5$ |
| 4.142 | $Q_5$ | H | $CF_3$ | — | $CH_3$ |
| 4.143 | $Q_7$ | H | — | $C_6H_5$ | H |
| 4.144 | $Q_7$ | $C_6H_5$ | — | $CH_3$ | H |
| 4.145 | $Q_7$ | H | — | $CH_3$ | $C_6H_5$ |
| 4.146 | $Q_7$ | $CH_3$ | — | 3,6-dimethylpyridazinyl | $CH_3$ |
| 4.147 | $Q_7$ | H | — | $CH_3$ | $OCH_3$ |
| 4.148 | $Q_7$ | $OCH_3$ | — | $CH_3$ | H |
| 4.149 | $Q_7$ | $N(CH_3)_2$ | — | $t$-$C_4H_9$ | $CH_3$ |
| 4.150 | $Q_7$ | $CH_3$ | — | $t$-$C_4H_9$ | $N(CH_3)_2$ |
| 4.151 | $Q_8$ | — | H | H | $CH_2C_6H_5$ |
| 4.152 | $Q_8$ | — | H | H | $SO_2C_6H_5$ |
| 4.153 | $Q_8$ | — | H | H | $C_6H_5$ |
| 4.154 | $Q_8$ | — | H | H | $CH_3$ |
| 4.155 | $Q_8$ | — | —CH=CH—CH=CH— | | $n$-$C_3H_7$ |
| 4.156 | $Q_8$ | — | Cl | Cl | $CH_2C_6H_5$ |
| 4.157 | $Q_8$ | — | H | H | $CONHCH_3$ |
| 4.158 | $Q_8$ | — | —CH=CH—CH=CH— | | CO-$t$-$C_4H_9$ |
| 4.159 | $Q_8$ | — | —CH=CH—CH=CH— | | CONH$t$-$C_4H_9$ |

TABLE 4-continued

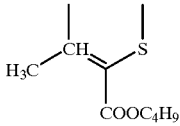

| Comp. No. | $Q_i$ | $R_{21}$ | $R_{22}$ | $R_{23}$ | $R_{24}$ |
|---|---|---|---|---|---|
| 4.160 | $Q_8$ | — | $CH_3$ | $CH_3$ | $CH_2OCH_3$ |
| 4.161 | $Q_8$ | — | —$CH_2$—$CH_2$—$CH_2$—$CH_2$— | | $CON(CH_3)_2$ |
| 4.162 | $Q_8$ | — | H | H | $SO_2N(CH_3)_2$ |
| 4.163 | $Q_{11}$ | — | —CH=C($CH_3$)—CH=CH— | | — |
| 4.164 | $Q_{11}$ | — | —CH=CH—C($CH_3$)=CH— | | — |
| 4.165 | $Q_{11}$ | — | —CH=CH—C(Cl)=CH— | | — |
| 4.166 | $Q_{11}$ | — | —CH=CH—CH=CH— | | — |
| 4.167 | $Q_{11}$ | — | $C_6H_5$ | H | — |
| 4.168 | $Q_{11}$ | — | 2-Cl—$C_6H_4$ | H | — |
| 4.169 | $Q_{11}$ | — | 4-F—$C_6H_4$ | H | — |
| 4.170 | $Q_{11}$ | — | 2-Furyl | H | — |
| 4.171 | $Q_{11}$ | — | 4-Tolyl | H | — |
| 4.172 | $Q_{11}$ | — | 4-Anisyl | H | — |
| 4.173 | $Q_{11}$ | — | 2-Thienyl | H | — |
| 4.174 | $Q_{11}$ | — | 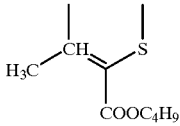 | H | — |
| 4.175 | $Q_{11}$ | — | 4-$CF_3$—$C_6H_4$ | $CO_2C_2H_5$ | — |
| 4.176 | $Q_{11}$ | — | $C_6H_5$ | $CO_2C_2H_5$ | — |
| 4.177 | $Q_{11}$ | — | 2,4-Dichlorophenyl | $CO_2C_2H_5$ | — |
| 4.178 | $Q_{11}$ | — | 3-Cl—$C_6H_4$ | $CO_2C_2H_5$ | — |
| 4.179 | $Q_{11}$ | — | t-$C_4H_9$ | $CO_2C_2H_5$ | — |
| 4.180 | $Q_{13}$ | H | — | — | H |
| 4.181 | $Q_{13}$ | $CH_3$ | — | — | $CH_3$ |
| 4.182 | $Q_{13}$ | $C_6H_5$ | — | — | $CH_3$ |
| 4.183 | $Q_{13}$ | H | — | — | $CH_3$ |
| 4.184 | $Q_{13}$ | H | — | — | 2-Thienyl |
| 4.185 | $Q_{13}$ | $CH_3$ | — | — | $CON(CH_3)_2$ |
| 4.186 | $Q_{13}$ | $CH_3$ | — | — | $CH_2OC_2H_5$ |
| 4.187 | $Q_{13}$ | H | — | — | $CH(OC_2H_5)_2$ |
| 4.188 | $Q_{13}$ | H | — | — | 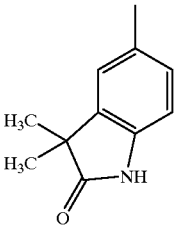 |
| 4.189 | $Q_{13}$ | 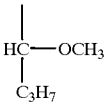 | — | — | $CH_3$ |
| 4.190 | $Q_{13}$ | $C_6H_5$ | — | — | 2-Furyl |
| 4.191 | $Q_{13}$ | 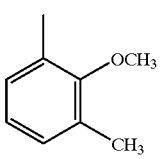 | — | — | 4-Cl-$C_6H_4$ |
| 4.192 | $Q_{13}$ | $C_6H_5$ | — | — | 2,4-Dichlorophenyl |

TABLE 4-continued $$\underset{H_3C}{\overset{|}{CH}}=\underset{COOC_4H_9}{\overset{|}{C}}-S$$

| Comp. No. | $Q_i$ | $R_{21}$ | $R_{22}$ | $R_{23}$ | $R_{24}$ |
|---|---|---|---|---|---|
| 4.193 | $Q_{13}$ | $CH_3$ | — | — | 3-methylquinuclidinyl |
| 4.194 | $Q_{13}$ | $(CH_2)_5Cl$ | — | — | $CH_2OCH_3$ |
| 4.195 | $Q_{13}$ | $N(CH_3)C_8H_5$ | — | — | $t\text{-}C_4H_9$ |
| 4.196 | $Q_{13}$ | 1,2-dimethylpyrrolidin-2-yl | — | — | $CH_3$ |
| 4.197 | $Q_{13}$ | $CH_3$ | — | — | 1,2-dimethylpyrrolidin-2-yl |
| 4.198 | $Q_{13}$ | $CH_3$ | — | — | $CF_3$ |
| 4.199 | $Q_{16}$ | $OC_2H_5$ | — | $CH_3$ | — |
| 4.200 | $Q_{16}$ | $OH$ | — | $i\text{-}C_3H_7$ | — |
| 4.201 | $Q_{16}$ | $OCH_3$ | — | $t\text{-}C_4H_9$ | — |
| 4.202 | $Q_{17}$ | — | H | H | — |
| 4.203 | $Q_{17}$ | — | H | $CH_3$ | — |
| 4.204 | $Q_{17}$ | — | H | $C_6H_5$ | — |
| 4.205 | $Q_{17}$ | — | H | CN | — |
| 4.206 | $Q_{17}$ | — | —CH=CH—CH=CH— | | — |
| 4.207 | $Q_{17}$ | — | —CF=CH—CH=CH— | | — |
| 4.208 | $Q_{17}$ | — | —CH=CH—CH=CF— | | — |
| 4.209 | $Q_{17}$ | — | —CH=CH—CCl=CH— | | — |
| 4.210 | $Q_{17}$ | — | —CH=CH—CH=CH— | | — |
| 4.211 | $Q_{17}$ | — | $Si(CH_3)_3$ | H | — |
| 4.212 | $Q_{17}$ | — | $CH_3$ | H | — |
| 4.213 | $Q_{17}$ | — | $C_6H_5$ | H | — |
| 4.214 | $Q_{17}$ | — | $Si(CH_3)_3$ | $CH_2OCH_3$ | — |
| 4.215 | $Q_{18}$ | $CH_2C_6H_5$ | H | — | — |
| 4.216 | $Q_{18}$ | —CH=CH—CH=CH— | | — | — |
| 4.217 | $Q_{18}$ | H | H | — | — |
| 4.218 | $Q_{18}$ | H | $CH_3$ | — | — |
| 4.219 | $Q_{18}$ | $CON(C_2H_5)_2$ | H | — | — |
| 4.220 | $Q_{18}$ | $NHCOOC_2H_5$ | H | — | — |
| 4.221 | $Q_{18}$ | $NHCOC_6H_5$ | H | — | — |
| 4.222 | $Q_{18}$ | $C_6H_5$ | $SCH_3$ | — | — |
| 4.223 | $Q_{18}$ | $(CH_3)_2C(CONMe_2)$— | $CH_3$ | — | — |
| 4.224 | $Q_{18}$ | 4-Tolyl | $SCH_3$ | — | — |

TABLE 4-continued

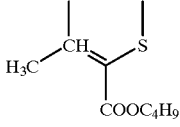

| Comp. No. | $Q_i$ | $R_{21}$ | $R_{22}$ | $R_{23}$ | $R_{24}$ |
|---|---|---|---|---|---|
| 4.225 | $Q_{18}$ | 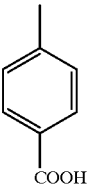 | H | — | — |
| 4.226 | $Q_{18}$ | H | O-n-$C_4H_9$ | — | — |
| 4.227 | $Q_{18}$ | —$CH_2$—$(CH_2)_3$—$CH_2$— | | — | — |
| 4.228 | $Q_{18}$ | H | O-i-$C_3H_7$ | — | — |
| 4.229 | $Q_{18}$ | —$CH_2$—$(CH_2)_4$—$CH_2$— | | — | — |
| 4.230 | $Q_{18}$ | $CH_3$ | 4-Tolyl | — | — |
| 4.231 | $Q_{18}$ | H | 2-Tolyl | — | — |
| 4.232 | $Q_{18}$ | H | $CBr_3$ | — | — |
| 4.233 | $Q_{18}$ | 4-Cl—$C_6H_4$ | H | — | — |
| 4.234 | $Q_{18}$ | —CH=CH—S— | | — | — |
| 4.235 | $Q_{18}$ | $CH(OC_2H_5)_2$ | $CH_3$ | — | — |
| 4.236 | $Q_{18}$ | 4-Cl—$C_6H_4$ | $CON(CH_3)_2$ | — | — |
| 4.237 | $Q_{18}$ | —S—CH=CH— | | — | — |
| 4.238 | $Q_{15}$ | H | 4-Cl-$C_6H_4$ | — | — |
| 4.239 | $Q_{20}$ | — | $CH_3$ | — | $CH_3$ |
| 4.240 | $Q_{20}$ | — | i-$C_4H_9$ | — | H |
| 4.241 | $Q_{20}$ | — | i-$C_3H_7$ | — | $CH_3$ |
| 4.242 | $Q_{20}$ | — | $C_2H_5$ | — | $CH_3$ |
| 4.243 | $Q_{20}$ | — | $CH_3$ | — | t-$C_4H_9$ |
| 4.244 | $Q_{20}$ | — | s-$C_4H_9$ | — | H |
| 4.245 | $Q_{20}$ | — | i-$C_4H_9$ | — | $CH_3$ |
| 4.246 | $Q_{20}$ | — | $Si(CH_3)_3$ | — | H |
| 4.247 | $Q_{20}$ | — | n-$C_3H_7$ | — | H |
| 4.248 | $Q_{20}$ | — | $CH_3$ | — | $CH_3$ |
| 4.249 | $Q_{20}$ | — | $OC_2H_5$ | — | H |
| 4.250 | $Q_{20}$ | — | $CH_3$ | — | CN |
| 4.251 | $Q_{20}$ | — | H | — | $C_6H_5$ |
| 4.252 | $Q_{20}$ | — | $CH_3$ | — | 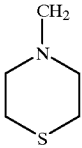 |
| 4.253 | $Q_{20}$ | — | $CH_3$ | — | 3-Pyridyl |
| 4.254 | $Q_{20}$ | — | $C_6H_5$ | — | $CONHCH_3$ |
| 4.255 | $Q_{20}$ | — | $NHCOCH_3$ | — | $CF_3$ |
| 4.256 | $Q_{21}$ | H | — | — | $C_6H_5$ |
| 4.257 | $Q_{21}$ | $CH_2OCH_3$ | — | — | $C_6H_5$ |
| 4.258 | $Q_{21}$ | $CH_3$ | — | — | 4-Cl—$C_6H_4$ |
| 4.259 | $Q_{30}$ | — | — | $C_6H_5$ | — |
| 4.260 | $Q_{30}$ | — | — | n-$C_4H_9$ | — |
| 4.261 | $Q_{33}$ | $C_6H_5$ | — | — | — |
| 4.262 | $Q_{33}$ | t-$C_4H_9$ | — | — | — |
| 4.263 | $Q_{33}$ | i-$C_3H_7$ | — | — | — |
| 4.264 | $Q_{33}$ | $C_2H_5$ | — | — | — |
| 4.265 | $Q_{33}$ | $CH_3$ | — | — | — |
| 4.266 | $Q_{33}$ | $OCH_3$ | — | — | — |
| 4.267 | $Q_{33}$ | O-n-$C_4H_9$ | — | — | — |
| 4.268 | $Q_{33}$ | $N(C_2H_5)_2$ | — | — | — |
| 4.269 | $Q_{33}$ | $SCH_3$ | — | — | — |
| 4.270 | $Q_{33}$ | S-c-$C_6H_{11}$ | — | — | — |

TABLE 4-continued

[Structure: H₃C–CH=C(S–CH₃?)(COOC₄H₉) with a CH(CH₃) group]

| Comp. No. | Q_i | R_21 | R_22 | R_23 | R_24 |
|---|---|---|---|---|---|
| 4.271 | $Q_{33}$ | 4-Cl-C₆H₄-S- | — | — | — |
| 4.272 | $Q_{33}$ | 4-Cl-C₆H₄-SO₂- | — | — | — |
| 4.273 | $Q_{33}$ | 3-CF₃-C₆H₄-O- | — | — | — |
| 4.274 | $Q_{39}$ | — | — | — | CH₃ |
| 4.275 | $Q_{39}$ | — | — | — | C₆H₅ |
| 4.276 | $Q_{39}$ | — | — | — | n-C₄H₉ |
| 4.277 | $Q_{20}$ | — | Cl | — | H |
| 4.278 | $Q_{20}$ | — | O—CH₂CF₃ | — | H |
| 4.279 | $Q_{20}$ | — | —CN | — | H |
| 4.280 | $Q_{20}$ | — | 3,5-(CH₃)₂-C₆H₃-O- | — | H |
| 4.281 | $Q_{20}$ | — | 2,5-F₂-C₆H₃-O- | — | H |
| 4.282 | $Q_{20}$ | — | C₆F₅-O- | — | H |

TABLE 4-continued

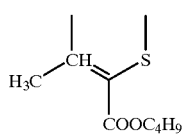

| Comp. No. | $Q_i$ | $R_{21}$ | $R_{22}$ | $R_{23}$ | $R_{24}$ |
|---|---|---|---|---|---|
| 4.283 | $Q_2$ | $CH_3$ | 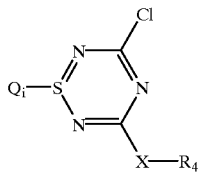 | — |

TABLE 5

Compounds of the formula VIa (VIa)

[structure of formula VIa shown: six-membered ring with S, N, N, N positions; $Q_i$—S, Cl on ring, X—$R_4$ substituent]

| Comp. No. | $Q_i$ | $R_{21}$ | $R_{22}$ | $R_{23}$ | $R_{24}$ | $XR_4$ |
|---|---|---|---|---|---|---|
| 5.001 | $Q_1$ | H | —CH=CH—CH=N— | | $CH_3$ | 2,6-dichlorophenoxy |
| 5.002 | $Q_1$ | $CH_3$ | —C(Cl)=CH—CH=N— | | $COCH_3$ | 3-fluorophenoxy |
| 5.003 | $Q_1$ | | —S—CH=CH— | H | 4-$CH_3$—$C_6H_4$ | phenoxy |
| 5.004 | $Q_1$ | | —CH=CH—S— | H | 4-$CH_3$—$C_6H_4$ | 2,3,5,6-tetrafluoro-4-(trifluoromethyl)phenoxy |
| 5.005 | $Q_2$ | H | $CH_3$ | H | — | 2,5-difluorophenoxy |

TABLE 5-continued
Compounds of the formula VIa
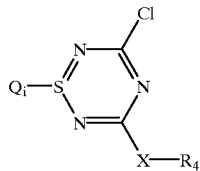
(VIa)
| Comp. No. | $Q_i$ | $R_{21}$ | $R_{22}$ | $R_{23}$ | $R_{24}$ | $XR_4$ |
|---|---|---|---|---|---|---|
| 5.006 | $Q_2$ | H | H | H | — | 4-nitro-2-(trifluoromethyl)phenoxy |
| 5.007 | $Q_2$ | H | H | —CH=CHCH$_3$ | — | 2,5-difluorophenoxy |
| 5.008 | $Q_2$ | H | —CH=CH—CH=CH— | | — | 4-carboxy-2-methoxyphenoxy |
| 5.009 | $Q_2$ | 2-methyl-4,4-dimethyl-4,5-dihydrooxazole | H | H | — | pentafluorophenoxy |
| 5.010 | $Q_2$ | H | H | SCH$_3$ | — | 2,5-difluorophenoxy |
| 5.011 | $Q_2$ | H | H | COOCH$_3$ | — | 3-cyanophenoxy |
| 5.012 | $Q_2$ | H | H | —CH=CH$_2$ | — | pentafluorophenoxy |

TABLE 5-continued
Compounds of the formula VIa
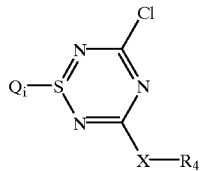
(VIa)
| Comp. No. | $Q_i$ | $R_{21}$ | $R_{22}$ | $R_{23}$ | $R_{24}$ | $XR_4$ |
|---|---|---|---|---|---|---|
| 5.013 | $Q_2$ | H | H | $S(O)CH_3$ | — | ![3,4,5-trimethylphenoxy] |
| 5.014 | $Q_2$ | H | H | $Si(CH_3)_3$ | — | ![2,5-difluorophenoxy] |
| 5.015 | $Q_2$ | H | —C(Cl)=CH—C(Cl)=CH— | | — | ![2,4-dichlorophenoxy] |
| 5.016 | $Q_2$ | H | H | $COCH_3$ | — | ![pentafluorophenoxy] |
| 5.017 | $Q_2$ | H | H | $OCH_3$ | — | ![2,5-difluorophenoxy] |
| 5.018 | $Q_2$ | H | H | Cl | — | ![pentafluorophenoxy] |
| 5.019 | $Q_2$ | H | —C(OCH$_3$)=CH—CH=CH— | | — | ![2,5-dichlorophenoxy] |

TABLE 5-continued
Compounds of the formula VIa
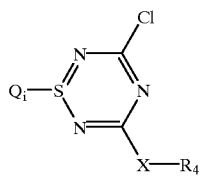
(VIa)
| Comp. No. | $Q_i$ | $R_{21}$ | $R_{22}$ | $R_{23}$ | $R_{24}$ | $XR_4$ |
|---|---|---|---|---|---|---|
| 5.020 | $Q_2$ | $CH_3$ | (structure with CH groups, $H_3C$, $CH_2$, $O\text{-}i\text{-}C_3H_7$) | | — | 2,3,6-trifluorophenoxy |
| 5.021 | $Q_2$ | H | —C(CH$_3$)=CH—CH=CH— | | — | 2,5-difluorophenoxy |
| 5.022 | $Q_2$ | H | —CH=CH—CH=C(CH$_3$)— | | — | 2,5-dimethylphenoxy |
| 5.023 | $Q_2$ | H | H | —C≡CH | — | pentafluorophenoxy |
| 5.024 | $Q_2$ | OH | —CH=CH—CH=CH— | | — | 3-methylphenoxy |
| 5.025 | $Q_2$ | H | —CH=CH—CH=CH— | | — | pentafluorophenoxy |

TABLE 5-continued
Compounds of the formula VIa
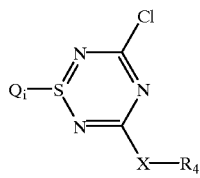
(VIa)
| Comp. No. | $Q_i$ | $R_{21}$ | $R_{22}$ | $R_{23}$ | $R_{24}$ | $XR_4$ |
|---|---|---|---|---|---|---|
| 5.026 | $Q_2$ | $CH_3$ | —CH=C($CH_3$)—C($CH_3$)=CH— | | — | 3,4,5-trimethoxyphenoxy |
| 5.027 | $Q_2$ | H | H | H | — | 2,5-difluorophenoxy |
| 5.028 | $Q_2$ | $CH_3$ | H | H | — | 2,5-difluorophenoxy |
| 5.029 | $Q_2$ | H | H | $C_2H_5$ | — | 4-nitro-2-trifluoromethylphenoxy |
| 5.030 | $Q_2$ | Cl | H | H | — | pentafluorophenoxy |
| 5.031 | $Q_2$ | H | H | n-$C_6H_{13}$ | — | phenoxy |
| 5.032 | $Q_2$ | H | H | $CH_3$ | — | 2,5-difluorophenoxy |

TABLE 5-continued
Compounds of the formula VIa
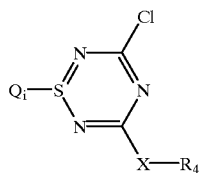
(VIa)
| Comp. No. | $Q_i$ | $R_{21}$ | $R_{22}$ | $R_{23}$ | $R_{24}$ | $XR_4$ |
|---|---|---|---|---|---|---|
| 5.033 | $Q_2$ | —CH$_2$—C(CH$_3$)=C(CH$_3$)—CH$_2$— | | H | — | 2,4-(OCH$_3$)$_2$-phenoxy |
| 5.034 | $Q_2$ | H | H | Sn(n-C$_4$H$_9$)$_3$ | — | 2,5-difluorophenoxy |
| 5.035 | $Q_2$ | H | CH$_3$ | H | — | 2,5-dichlorophenoxy |
| 5.036 | $Q_2$ | H | H | SO$_2$CH$_3$ | — | 2,5-difluorophenoxy |
| 5.037 | $Q_2$ | —CH=C(CH$_3$)—C(CH$_3$)=CH— | | H | — | 2-nitrophenoxy |
| 5.038 | $Q_2$ | H | H | C$_2$H$_5$ | — | phenoxy |
| 5.039 | $Q_2$ | H | H | H | — | pentafluorophenoxy |

TABLE 5-continued
Compounds of the formula VIa
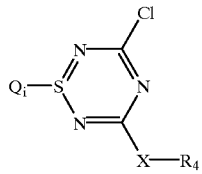
(VIa)
| Comp. No. | $Q_i$ | $R_{21}$ | $R_{22}$ | $R_{23}$ | $R_{24}$ | $XR_4$ |
|---|---|---|---|---|---|---|
| 5.040 | $Q_2$ | H | H | $t\text{-}C_4H_9$ | — | ![pentafluorophenoxy] |
| 5.041 | $Q_2$ | H | H | $n\text{-}C_4H_9$ | — | ![2,5-difluorophenoxy] |
| 5.042 | $Q_2$ | H | H | I | — | ![2,6-dichlorophenoxy] |
| 5.043 | $Q_2$ | H | H | $SCH_3$ | — | ![2,5-difluorophenoxy] |
| 5.044 | $Q_2$ | H | H | $B(OH)_2$ | — | ![4-chloro-tetrafluorophenoxy] |
| 5.045 | $Q_2$ | H | H | $OCH_3$ | — | ![2-fluoro-6-methyl-pyridin-3-yloxy] |
| 5.046 | $Q_2$ | H | —CH═CH—CH═CH— | | — | ![2,5-difluorophenoxy] |

TABLE 5-continued
Compounds of the formula VIa
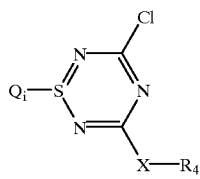
(VIa)
| Comp. No. | $Q_i$ | $R_{21}$ | $R_{22}$ | $R_{23}$ | $R_{24}$ | $XR_4$ |
|---|---|---|---|---|---|---|
| 5.047 | $Q_2$ | H | —CO—NH—CH=CH— | | — | ![o-cresyloxy] |
| 5.048 | $Q_2$ | H | $CH_3$ | F | — | ![o-cresyloxy] |
| 5.049 | $Q_2$ | $OCH_3$ | H | H | — | ![pentafluorophenoxy] |
| 5.050 | $Q_3$ | H | H | — | $CH_3$ | ![2-fluoropyridin-3-yloxy] |
| 5.051 | $Q_3$ | H | H | — | $CON(C_2H_5)_2$ | ![4-nitrophenoxy] |
| 5.052 | $Q_3$ | H | H | — | Cl | ![pentafluorophenoxy] |
| 5.053 | $Q_3$ | H | H | — | $OCH_3$ | ![3,6-difluoropyridin-2-yloxy] |

TABLE 5-continued

Compounds of the formula VIa

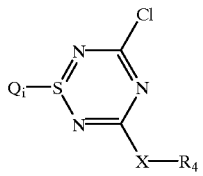

(VIa)

| Comp. No. | $Q_i$ | $R_{21}$ | $R_{22}$ | $R_{23}$ | $R_{24}$ | $XR_4$ |
|---|---|---|---|---|---|---|
| 5.054 | $Q_3$ | H | $Si(CH_3)_3$ | — | $CON(C_2H_5)_2$ | 2,5-difluorophenoxy |
| 5.055 | $Q_3$ | H | H | — | $CH_2OCH_3$ | 3-(n-butoxy)phenoxy |
| 5.056 | $Q_3$ | —CH=CH—CH=CH— | | — | $CON(C_2H_5)_2$ | (2-fluoro-5-fluoropyridin-3-yl)oxy |
| 5.057 | $Q_3$ | $CONH$-$t$-$C_4H_9$ | $CH_3$ | — | $CH_3$ | (3,6-difluoropyridin-2-yl)oxy |
| 5.058 | $Q_2$ | H | H | 2-methyl-4,4-dimethyl-oxazolin-4-yl | — | pentafluorophenoxy |
| 5.059 | $Q_3$ | —CH=CH—CH=CH— | | — | $CH_2N(CH_3)_2$ | (4,6-dibromo-2-methoxycarbonyl-pyridin-3-yl)oxy |
| 5.060 | $Q_3$ | —CH=CH—CH=CH— | | — | $H_2$N-pyrrolidinyl | (4-methylthiazol-2-yl)oxy |

TABLE 5-continued
Compounds of the formula VIa
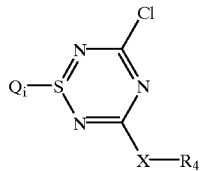
(VIa)
| Comp. No. | $Q_i$ | $R_{21}$ | $R_{22}$ | $R_{23}$ | $R_{24}$ | $XR_4$ |
|---|---|---|---|---|---|---|
| 5.061 | $Q_4$ | H | H | H | — | pentafluorophenoxy |
| 5.062 | $Q_4$ | H | —CH=CH—CH=CH— | | — | 5-chloro-2-nitrophenoxy |
| 5.063 | $Q_4$ | H | $CH_3$ | F | — | 2-methylphenoxy |
| 5.064 | $Q_4$ | $OCH_3$ | H | H | — | pentafluorophenoxy |
| 5.065 | $Q_4$ | H | —CH=CH—CH=CH— | | — | 2-fluoro-6-nitrophenoxy |
| 5.066 | $Q_4$ | H | H | $t\text{-}C_4H_9$ | — | pentafluorophenoxy |
| 5.067 | $Q_4$ | H | H | $n\text{-}C_4H_9$ | — | 2,5-difluorophenoxy |

TABLE 5-continued
Compounds of the formula VIa
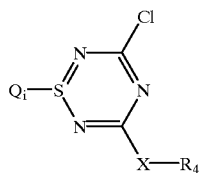
(VIa)
| Comp. No. | $Q_i$ | $R_{21}$ | $R_{22}$ | $R_{23}$ | $R_{24}$ | $XR_4$ |
|---|---|---|---|---|---|---|
| 5.068 | $Q_4$ | H | H | H | — | ![2,5-difluorophenoxy] |
| 5.069 | $Q_4$ | H | H | $CH_3$ | — | ![2-thienylthio] |
| 5.070 | $Q_4$ | $CH_3$ | H | H | — | ![2,5-difluorophenoxy] |
| 5.071 | $Q_4$ | H | H | $C_2H_5$ | — | ![4-nitro-2-trifluoromethylphenoxy] |
| 5.072 | $Q_4$ | Cl | H | H | — | ![pentafluorophenoxy] |
| 5.073 | $Q_4$ | H | H | $n\text{-}C_6H_{13}$ | — | ![phenoxy] |
| 5.074 | $Q_4$ | H | H | $Si(CH_3)_3$ | — | ![pentafluorophenoxy] |

TABLE 5-continued
Compounds of the formula VIa
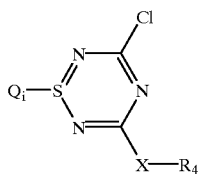
(VIa)
| Comp. No. | $Q_i$ | $R_{21}$ | $R_{22}$ | $R_{23}$ | $R_{24}$ | $XR_4$ |
|---|---|---|---|---|---|---|
| 5.075 | $Q_4$ | H | H | $Sn(n-C_4H_9)_3$ | — | ![2,5-difluorophenoxy] |
| 5.076 | $Q_4$ | H | H | H | — | ![4-(2-carboxyethyl)phenoxy] |
| 5.077 | $Q_4$ | H | H | $t-C_4H_9$ | — | ![2,5-difluorophenoxy] |
| 5.078 | $Q_4$ | H | H | I | — | ![2,6-dichlorophenoxy] |
| 5.079 | $Q_4$ | H | H | $B(OH)_2$ | — | ![4-chloro-2,3,5,6-tetrafluorophenoxy] |
| 5.080 | $Q_4$ | H | H | 2-thienyl | — | ![4-(ethoxycarbonyl)phenoxy] |

TABLE 5-continued
Compounds of the formula VIa
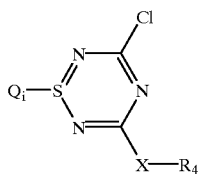
(VIa)
| Comp. No. | $Q_i$ | $R_{21}$ | $R_{22}$ | $R_{23}$ | $R_{24}$ | $XR_4$ |
|---|---|---|---|---|---|---|
| 5.081 | $Q_4$ | H | $CH_3$ | H | — | 2,5-dichlorophenoxy |
| 5.082 | $Q_4$ | $CH_3$ | H | H | — | pentafluorophenoxy |
| 5.083 | $Q_4$ | —$CH_2$—$CH_2$—$CH_2$—$C(OCH_3)_2$— | | $SCH_3$ | — | 3-cyanophenoxy |
| 5.084 | $Q_4$ | H | H | $C_2H_5$ | — | 2,5-difluorophenoxy |
| 5.085 | $Q_4$ | H | =HC–N(4-methylphenyl)–CH= | | — | 3-(ethoxycarbonyl)phenoxy |
| 5.086 | $Q_4$ | H | H | $COCH_3$ | — | pentafluorophenoxy |

TABLE 5-continued

Compounds of the formula VIa

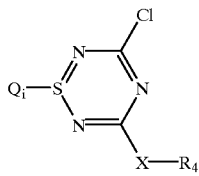

(VIa)

| Comp. No. | $Q_i$ | $R_{21}$ | $R_{22}$ | $R_{23}$ | $R_{24}$ | $XR_4$ |
|---|---|---|---|---|---|---|
| 5.087 | $Q_4$ | H₂C−C(CH₃)₂−CH(OC₃H₇)− | | $SCH_3$ | — | 3-methyl-5-isopropylphenoxy |
| 5.088 | $Q_4$ | H | H | $CH_3$ | — | 2,5-difluorophenoxy |
| 5.089 | $Q_4$ | H | −C(SCH₃)=CH−SCH₂CCH | | — | 4-methyl-3-acetylphenoxy (O−C₆H₃(CH₃)−COCH₃) |
| 5.090 | $Q_4$ | H | —CH═CH—CH═CH— | | — | pentafluorophenoxy |
| 5.091 | $Q_4$ | $CH_3$ | —C(CH₃)═C(SCH₃)—S— | | — | $SC_6H_5$ |
| 5.092 | $Q_4$ | H | −N(CH₃)−C(OCH₃)=N−C(OCH₃)= | | — | 3,4-dimethylphenoxy |
| 5.093 | $Q_4$ | H | H | $COOCH_3$ | — | 3-cyanophenoxy |
| 5.094 | $Q_4$ | H | H | 2-thienyl | — | 2,5-difluorophenoxy |

TABLE 5-continued

Compounds of the formula VIa

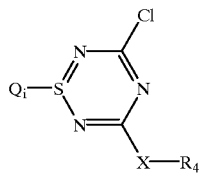
(VIa)

| Comp. No. | $Q_i$ | $R_{21}$ | $R_{22}$ | $R_{23}$ | $R_{24}$ | $XR_4$ |
|---|---|---|---|---|---|---|
| 5.095 | $Q_4$ | $CH_3$ | $\begin{array}{c}\phantom{x}\\H_3C-CH\\\phantom{x}\end{array}\!\!=\!\!\begin{array}{c}\phantom{x}\\S-\\COOC_4H_9\end{array}$ | | — | 3-chlorophenoxy |
| 5.096 | $Q_4$ | H | —S—CH=CH— | | — | 4-amino-2,3,5,6-tetrafluorophenoxy |
| 5.097 | $Q_4$ | H | —CH=CH—CH=CH— | | — | 2,5-difluorophenoxy |
| 5.098 | $Q_4$ | H | H | —C≡CH | — | pentafluorophenoxy |
| 5.099 | $Q_4$ | $CH_3$ | —CH=N—CH=N— | | — | 2-formylphenoxy |
| 5.100 | $Q_4$ | $CH_3$ | —N=CH—N=CH— | | — | benzocyclobutenone-oxy |
| 5.101 | $Q_4$ | $CH_3$ | $\begin{array}{c}\phantom{x}\\N\\\|\\N=C\\\|\\H\end{array}\!\!\!\begin{array}{c}\phantom{x}\\\phantom{x}\\C\!-\!N\\\|\\CH_3\end{array}\!\!\!\begin{array}{c}CH_2-CH_2-OH\\\phantom{x}\\\phantom{x}\end{array}$ | | — | 2,6-difluorophenoxy |

TABLE 5-continued

Compounds of the formula VIa

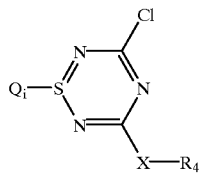

(VIa)

| Comp. No. | $Q_i$ | $R_{21}$ | $R_{22}$ | $R_{23}$ | $R_{24}$ | $XR_4$ |
|---|---|---|---|---|---|---|
| 5.102 | $Q_4$ | H | H | —CH=CH$_2$ | — | pentafluorophenoxy |
| 5.103 | $Q_4$ | H | H | Si(CH$_3$)$_3$ | — | 2,5-difluorophenoxy |
| 5.104 | $Q_4$ | H | C(SCH$_3$)=CH—C(O)O-t-C$_4$H$_9$ | | — | 3-cyanophenoxy |
| 5.105 | $Q_4$ | H | H | C$_2$H$_5$ | — | pentafluorophenoxy |
| 5.106 | $Q_4$ | H | N(CH$_3$)=C(OCH$_3$)—N=C(CF$_3$)— | | — | phthalimido-N-oxy |
| 5.107 | $Q_4$ | H | H | —CH=CHCH$_3$ | — | 2,5-difluorophenoxy |
| 5.108 | $Q_4$ | H | C(OCH$_3$)=C(OCH$_3$)—C(O)NHC$_2$H$_5$ | | — | 4-(2-methylbutan-2-yl)phenoxy |

TABLE 5-continued
Compounds of the formula VIa
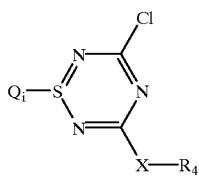
(VIa)
| Comp. No. | $Q_i$ | $R_{21}$ | $R_{22}$ | $R_{23}$ | $R_{24}$ | $XR_4$ |
|---|---|---|---|---|---|---|
| 5.109 | $Q_4$ | $C_6H_5$ | i-$C_3H_7$-S-C(=N-)-N(CH_3)-CH=N-H | — | — | -O-C_6H_4-SCH_3 (para) |
| 5.110 | $Q_4$ | H | H | $CH_3$ | — | -O-C_6F_5 |
| 5.111 | $Q_4$ | —$CH_2$—$C(CH_3)_2$—CH=C(OCH_3)— | | $SCH_3$ | — | $OCH_2CF_3$ |
| 5.112 | $Q_4$ | $CH_3$ | —C($CH_3$)=CH—S— | | — | -O-(3,4,5-tri-CH_3-C_6H_2) |
| 5.113 | $Q_4$ | H | H | n-$C_6H_{13}$ | — | -O-(2,5-di-F-C_6H_3) |
| 5.114 | $Q_4$ | $CH_3$ | pyrrolidin-1-yl-C(=N-)-N(CH_3)-CH=N-H | | — | -O-(2,3,5,6-tetra-F-4-NO_2-C_6) |
| 5.115 | $Q_4$ | H | H | $SO_2CH_3$ | — | -O-(2,5-di-F-C_6H_3) |

TABLE 5-continued
Compounds of the formula VIa
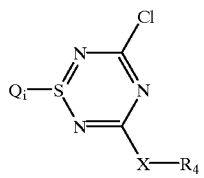
(VIa)
| Comp. No. | $Q_i$ | $R_{21}$ | $R_{22}$ | $R_{23}$ | $R_{24}$ | $XR_4$ |
|---|---|---|---|---|---|---|
| 5.116 | $Q_4$ | $CH_3$ | SCH_3) | | — | 2,5-dimethylphenoxy |
| 5.117 | $Q_4$ | $Si(CH_3)_3$ | H | H | — | 2,5-difluorophenoxy |
| 5.118 | $Q_4$ | $CH_3$ | =N-CH=N-CH_3) | | — | 4-chloro-2,3,5,6-tetrafluorophenoxy |
| 5.119 | $Q_4$ | H | =CH-N(NHCH_3)-C(=O)CH_3) | | — | 3,4,5-trimethylphenoxy |
| 5.120 | $Q_4$ | H | H | $n\text{-}C_6H_{13}$ | — | pentafluorophenoxy |
| 5.121 | $Q_4$ | $CH_3$ | =C(SCH_3)-C(=O)-morpholine) | | — | 2-n-propylphenoxy |

TABLE 5-continued

Compounds of the formula VIa

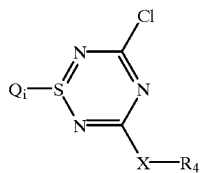
(VIa)

| Comp. No. | $Q_i$ | $R_{21}$ | $R_{22}$ | $R_{23}$ | $R_{24}$ | $XR_4$ |
|---|---|---|---|---|---|---|
| 5.122 | $Q_4$ | H | | $H_5C_2-\overset{|}{\underset{HO}{C}}-CH_2-S-$ (with methyl) | — | pentafluorophenoxy |
| 5.123 | $Q_4$ | $CH_3$ | | $H_3C-\underset{COOCH_3}{\overset{CH_3}{C}}=C-S-CH_3$ | — | 2-chloro-4-nitrophenoxy |
| 5.124 | $Q_4$ | $CH_3$ | | (N,N-methylformamidino)(4-chlorophenylthio)methyl | — | pentafluorophenoxy |
| 5.125 | $Q_4$ | H | | $HC=\underset{COOH}{C}-S-CH_3$ (with CH_3) | — | 2-(trifluoromethyl)phenoxy |
| 5.126 | $Q_4$ | H | $CH_3$ | H | — | 2,5-difluorophenoxy |
| 5.127 | $Q_4$ | H | | $HC=C-S-CH_3$ with $CH_2OC_3H_7$ | — | $OC_6H_5$ |
| 5.128 | $Q_4$ | H | | $\underset{H_3C}{\overset{H_3C}{N}}-C(=CH-CH_3)-C(=O)-CH_3$ | — | 2,5-difluorophenoxy |

TABLE 5-continued

Compounds of the formula VIa

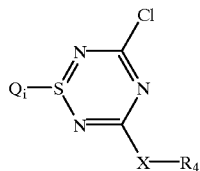

(VIa)

| Comp. No. | $Q_i$ | $R_{21}$ | $R_{22}$ | $R_{23}$ | $R_{24}$ | $XR_4$ |
|---|---|---|---|---|---|---|
| 5.129 | $Q_4$ | H | (H₃C)₂C=C(SCH₃)–C(O)–N(morpholine) | | — | 3,3,5,5-tetramethylcyclohexyloxy |
| 5.130 | $Q_4$ | H | H | I | — | 2,5-difluorophenoxy |
| 5.131 | $Q_4$ | H | ClC(=C(SCH₃))–C(O)–NHCH₂C₆H₅ | | — | 4-(t-C₄H₉-methyl)phenoxy |
| 5.132 | $Q_4$ | H | H | S(O)CH₃ | — | 3,4,5-trimethylphenoxy |
| 5.133 | $Q_4$ | H | —CH=CH—CH=C(CH₃)— | | — | 2-(CF₃)phenoxy |
| 5.134 | $Q_4$ | —(CH₂)₂NH₂ | —CH=CH—C(OCH₃)=CH— | | — | 2,5-difluorophenoxy |
| 5.135 | $Q_4$ | —(CH₂)₂N(CH₃)₂ | —C(OCH₃)=CH—CH=CH— | | — | 4-(t-C₄H₉)phenoxy |

TABLE 5-continued

Compounds of the formula VIa

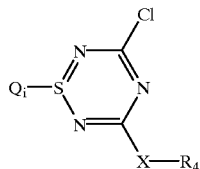

(VIa)

| Comp. No. | $Q_i$ | $R_{21}$ | $R_{22}$ | $R_{23}$ | $R_{24}$ | $XR_4$ |
|---|---|---|---|---|---|---|
| 5.136 | $Q_4$ | H | H | $B(OH)_2$ | — | pentafluorophenoxy |
| 5.137 | $Q_4$ | —$(CH_2)_2OH$ | —CH=CH—CH=CH— | | — | 4-carboxyphenoxy |
| 5.138 | $Q_4$ | —$CH_2SH$ | —CH=CH—CH=CH— | | — | 2,6-dimethylpyridin-4-yloxy |
| 5.139 | $Q_4$ | $CH_3$ | —CH=CF—CH=CH— | | — | $OCH_2CF_3$ |
| 5.140 | $Q_4$ | H | ethyl 3-methylpenta-2,4-dienoate substituent | | — | $SCH_2C_6H_5$ |
| 5.141 | $Q_4$ | H | H | 2-thienyl | — | pentafluorophenoxy |
| 5.142 | $Q_4$ | $OCH_3$ | 3-ethoxy-penta-2,4-dienyl substituent | | — | $OC_6H_5$ |
| 5.143 | $Q_4$ | H | H | $SCH_3$ | — | 2,5-difluorophenoxy |

TABLE 5-continued

Compounds of the formula VIa

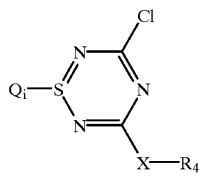

(VIa)

| Comp. No. | $Q_i$ | $R_{21}$ | $R_{22}$ | $R_{23}$ | $R_{24}$ | $XR_4$ |
|---|---|---|---|---|---|---|
| 5.144 | $Q_4$ | $(CH_2)_2OCOCH_3$ | \[2,2-dimethyl-4,5-bis(ethylidene)-1,3-dioxolane\] | | — | $OCH_2C_7F_{15}$ |
| 5.145 | $Q_4$ | H | H | $Sn(CH_3)_3$ | — | 2,5-difluorophenoxy |
| 5.146 | $Q_4$ | $CH_2CON(CH_3)_2$ | —CH=CH—C(OCH$_3$)=CH— | | — | 3-(N,N-diethylamino)phenoxy |
| 5.147 | $Q_4$ | H | $CH_3$ | H | — | pentafluorophenoxy |
| 5.148 | $Q_4$ | \[H$_3$CO—C(CH$_3$)(C$_2$H$_5$)(OCH$_3$)\] | —CH=CH—CH=CH— | | — | 2-naphthyloxy |
| 5.149 | $Q_4$ | H | H | $OCH_3$ | — | 2,5-difluorophenoxy |
| 5.150 | $Q_4$ | H | —C(OH)=CH—CH=CH— | | — | 2,6-dichlorophenoxy |

TABLE 5-continued

Compounds of the formula VIa

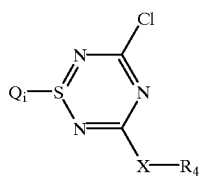

(VIa)

| Comp. No. | $Q_i$ | $R_{21}$ | $R_{22}$ | $R_{23}$ | $R_{24}$ | $XR_4$ |
|---|---|---|---|---|---|---|
| 5.151 | $Q_4$ | H | H | $Sn(n-C_4H_9)_3$ | — | pentafluorophenoxy |
| 5.152 | $Q_4$ | $CH_3$ | | —CH=CH—CH=CH— | — | benzo[1,3]dioxol-5-yloxy |
| 5.153 | $Q_4$ | $CH_2CO_2H$ | | —CH=CH—CH=CH— | — | 3-(pentylthio)phenoxy |
| 5.154 | $Q_4$ | $CH_2CO_2C_2H_5$ | | —CH=C(Cl)—CH=CH— | — | 2,3,5,6-tetrafluorophenoxy |
| 5.155 | $Q_4$ | $CH_3$ | | —CH=C(Cl)—CH=CH— | — | pentafluorophenoxy |
| 5.156 | $Q_4$ | H | | —CH=C($CH_3$)—CH=CH— | — | 4-(trifluoromethyl)phenoxy |
| 5.157 | $Q_4$ | H | H | Cl | — | pentafluorophenoxy |

TABLE 5-continued

Compounds of the formula VIa

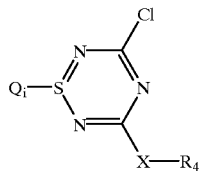

(VIa)

| Comp. No. | $Q_i$ | $R_{21}$ | $R_{22}$ | $R_{23}$ | $R_{24}$ | $XR_4$ |
|---|---|---|---|---|---|---|
| 5.158 | $Q_4$ | $CH_3$ | —CH=C($CH_3$)—CH=CH— | — | | o-ethylphenoxy |
| 5.159 | $Q_4$ | H | Si($CH_3$)$_3$ | H | — | pentafluorophenoxy |
| 5.160 | $Q_4$ | $NHC_4H_9$ | —CH=CH—CH=CH— | | — | pentafluorophenoxy |
| 5.161 | $Q_4$ | $CH_2N(CH_3)_2$ | —CH=CH—CH=CH— | | — | o-n-propylphenoxy |
| 5.162 | $Q_4$ | $CH_2$-morpholino | —CH=CH—CH=CH— | | — | 2,3,5,6-tetrafluorophenoxy |
| 5.163 | $Q_4$ | H | H | n-$C_4H_9$ | — | pentafluorophenoxy |
| 5.164 | $Q_5$ | H | H | — | $C_6H_5$ | 2,4-bis(trifluoromethyl)phenoxy |

TABLE 5-continued

Compounds of the formula VIa

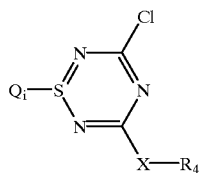

(VIa)

| Comp. No. | $Q_i$ | $R_{21}$ | $R_{22}$ | $R_{23}$ | $R_{24}$ | $XR_4$ |
|---|---|---|---|---|---|---|
| 5.165 | $Q_5$ | H | $CH_3$ | — | $C_6H_5$ | pentafluorophenoxy |
| 5.166 | $Q_5$ | H | $CH_3$ | — | $CH_2OCH_3$ | 2-naphthyloxy |
| 5.167 | $Q_5$ | $C_6H_5$ | $CH_3$ | — | $CON(CH_3)_2$ | 2,5-difluorophenoxy |
| 5.168 | $Q_5$ | —CH=CH—CH=CH— | | — | $CH_3$ | 2-fluoro-6-methylpyridin-3-yloxy |
| 5.169 | $Q_5$ | H | $C_2H_5$ | — | 2-Cl—$C_6H_4$ | 2-methylphenoxy |
| 5.170 | $Q_5$ | H | 3-($NH_2$)—$C_6H_4$ | — | $CH_3$ | 5-chloro-3-fluoropyridin-2-yloxy |
| 5.171 | $Q_5$ | H | $C(OCH_3)_3$ | — | $i$-$C_3H_7$ | 4-chloro-1-methyl-3-trifluoromethylpyrazol-5-yloxy |

TABLE 5-continued
Compounds of the formula VIa
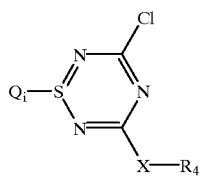
(VIa)
| Comp. No. | $Q_i$ | $R_{21}$ | $R_{22}$ | $R_{23}$ | $R_{24}$ | $XR_4$ |
|---|---|---|---|---|---|---|
| 5.172 | $Q_5$ | H | $CH_3$ | — | $t$-$C_4H_9$ | pentafluorophenoxy |
| 5.173 | $Q_5$ | H | $SCH_3$ | — | $t$-$C_4H_9$ | pentafluorophenoxy |
| 5.174 | $Q_5$ | H | 2-Thiazolyl | — | $CH_3$ | 2,5-difluorophenoxy |
| 5.175 | $Q_5$ | $H_2C{-}O{-}CH(CH_3)$ (isopropoxymethyl) | | — | $CH_3$ | 2,5-difluorophenoxy |
| 5.176 | $Q_5$ | H | 3-Cl—$C_6H_4$ | — | $CH_2OC_2H_5$ | 2,5-difluorophenoxy |
| 5.177 | $Q_5$ | H | $CF_3$ | — | $CH_3$ | 4-$t$-$C_4H_9$-phenoxy |

TABLE 5-continued
Compounds of the formula VIa
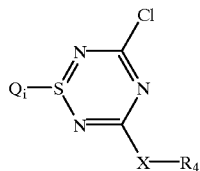
(VIa)
| Comp. No. | $Q_i$ | $R_{21}$ | $R_{22}$ | $R_{23}$ | $R_{24}$ | $XR_4$ |
|---|---|---|---|---|---|---|
| 5.178 | $Q_5$ | H | $CH_3$ | — | $C_6H_5$ | 4-(COCH$_3$CH$_2$CH$_2$)-C$_6$H$_4$-O- |
| 5.179 | $Q_7$ | H | — | $C_6H_5$ | H | 2-(CF$_3$)-C$_6$H$_4$-O- |
| 5.180 | $Q_7$ | $C_6H_5$ | — | $CH_3$ | H | C$_6$F$_5$-O- |
| 5.181 | $Q_7$ | H | — | $CH_3$ | $C_6H_5$ | 2,5-F$_2$-C$_6$H$_3$-O- |
| 5.182 | $Q_7$ | $CH_3$ | — | 3,6-dimethylpyridazinyl | $CH_3$ | C$_6$F$_5$-O- |
| 5.183 | $Q_7$ | H | — | $CH_3$ | $OCH_3$ | 4-(CF$_3$)-C$_6$H$_4$-O- |
| 5.184 | $Q_7$ | $OCH_3$ | — | $CH_3$ | H | C$_6$F$_5$-O- |

TABLE 5-continued
Compounds of the formula VIa
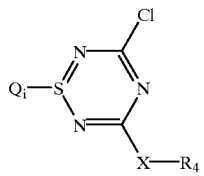
(VIa)
| Comp. No. | $Q_i$ | $R_{21}$ | $R_{22}$ | $R_{23}$ | $R_{24}$ | $XR_4$ |
|---|---|---|---|---|---|---|
| 5.185 | $Q_7$ | $N(CH_3)_2$ | — | $t-C_4H_9$ | $CH_3$ | 2,5-difluorophenoxy |
| 5.186 | $Q_7$ | $CH_3$ | — | $t-C_4H_9$ | $N(CH_3)_2$ | 2,5-difluorophenoxy |
| 5.187 | $Q_8$ | — | H | H | $CH_2C_6H_5$ | 2,5-difluorophenoxy |
| 5.188 | $Q_8$ | — | H | H | $SO_2C_6H_5$ | pentafluorophenoxy |
| 5.189 | $Q_8$ | — | H | H | $COO-t-C_4H_9$ | 3-chloro-4-fluorophenoxy |
| 5.190 | $Q_8$ | — | H | H | $CONHt-C_4H_9$ | pentafluorophenoxy |
| 5.191 | $Q_8$ | — | H | H | $C_6H_5$ | 2,5-difluorophenoxy |

TABLE 5-continued
Compounds of the formula VIa
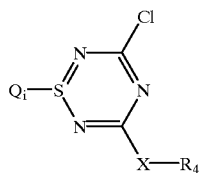
(VIa)
| Comp. No. | $Q_i$ | $R_{21}$ | $R_{22}$ | $R_{23}$ | $R_{24}$ | $XR_4$ |
|---|---|---|---|---|---|---|
| 5.192 | $Q_8$ | — | H | H | $CH_3$ | pentafluorophenoxy |
| 5.193 | $Q_8$ | — | —CH=CH—CH=CH— | | $n\text{-}C_3H_7$ | 2-chloro-5-methylphenoxy |
| 5.194 | $Q_8$ | — | Cl | Cl | $CH_2C_6H_5$ | 2,5-difluorophenoxy |
| 5.195 | $Q_8$ | — | H | H | $CONHCH_3$ | pentafluorophenoxy |
| 5.196 | $Q_8$ | — | —CH=CH—CH=CH— | | $CO\text{-}t\text{-}C_4H_9$ | pentafluorophenoxy |
| 5.197 | $Q_8$ | — | —CH=CH—CH=CH— | | $CONHt\text{-}C_4H_9$ | 2,6-difluorophenoxy |

TABLE 5-continued
Compounds of the formula VIa
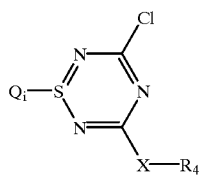
(VIa)
| Comp. No. | $Q_i$ | $R_{21}$ | $R_{22}$ | $R_{23}$ | $R_{24}$ | $XR_4$ |
|---|---|---|---|---|---|---|
| 5.198 | $Q_8$ | — | $CH_3$ | $CH_3$ | $CH_2OCH_3$ | 2,5-difluorophenoxy |
| 5.199 | $Q_8$ | — | —$CH_2$—$CH_2$—$CH_2$—$CH_2$— | | $CON(CH_3)_2$ | 2-(n-$C_3H_7$)phenoxy |
| 5.200 | $Q_8$ | — | H | H | $SO_2NH_2$ | pentafluorophenoxy |
| 5.201 | $Q_{11}$ | — | —CH=C($CH_3$)—CH=CH— | | — | 2,5-difluorophenoxy |
| 5.202 | $Q_{11}$ | — | —CH=CH—C($CH_3$)=CH— | | — | 2-$C_6H_{13}$-phenoxy |
| 5.203 | $Q_{11}$ | — | —CH=CH—C(Cl)=CH— | | — | phthalide-oxy |
| 5.204 | $Q_{11}$ | — | —CH=CH—CH=CH— | | — | 2,5-difluorophenoxy |

TABLE 5-continued
Compounds of the formula VIa
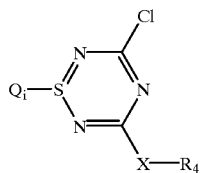
(VIa)
| Comp. No. | $Q_i$ | $R_{21}$ | $R_{22}$ | $R_{23}$ | $R_{24}$ | $XR_4$ |
|---|---|---|---|---|---|---|
| 5.205 | $Q_{11}$ | — | 3-$NH_2$—$C_6H_4$ | H | — | 2,5-difluorophenoxy |
| 5.206 | $Q_{11}$ | — | $C_6H_5$ | H | — | pentafluorophenoxy |
| 5.207 | $Q_{11}$ | — | 2-Cl—$C_6H_4$ | H | — | pentafluorophenoxy |
| 5.208 | $Q_{11}$ | — | 4-F—$C_6H_4$ | H | — | 3,3,5,5-tetramethylcyclohexyloxy |
| 5.209 | $Q_{11}$ | — | 2-Furyl | H | — | 3-$CF_3$-phenoxy |
| 5.210 | $Q_{11}$ | — | 4-Tolyl | H | — | 2,6-dimethylpyridin-4-yloxy |
| 5.211 | $Q_{11}$ | — | 4-Anisyl | H | — | 2-ethylphenoxy |

TABLE 5-continued

Compounds of the formula VIa

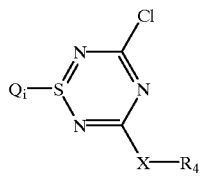

(VIa)

| Comp. No. | $Q_i$ | $R_{21}$ | $R_{22}$ | $R_{23}$ | $R_{24}$ | $XR_4$ |
|---|---|---|---|---|---|---|
| 5.212 | $Q_{11}$ | — | 2-Thienyl | H | — | 2,3,6-trifluorophenoxy |
| 5.213 | $Q_{11}$ | — | 3,3-dimethyl-5-methyl-2-oxoindolin-1-yl | H | — | 3-(tert-butylthio)phenoxy |
| 5.214 | $Q_{11}$ | — | 4-$CF_3$—$C_6H_4$ | $CO_2C_2H_5$ | — | $OC_8H_{17}$ |
| 5.215 | $Q_{11}$ | — | $C_6H_5$ | $CO_2C_2H_5$ | — | pentafluorophenoxy |
| 5.216 | $Q_{11}$ | — | 2,4-Dichlorophenyl | $CO_2C_2H_5$ | — | 2,5-difluorophenoxy |
| 5.217 | $Q_{11}$ | — | 3-Cl—$C_6H_4$ | $CO_2C_2H_5$ | — | 3-methyl-5-isopropylphenoxy |
| 5.218 | $Q_{11}$ | — | t-$C_4H_9$ | $CO_2C_2H_5$ | — | pentafluorophenoxy |

TABLE 5-continued
Compounds of the formula VIa
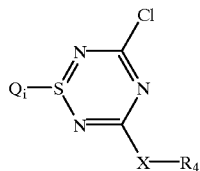
(VIa)
| Comp. No. | $Q_i$ | $R_{21}$ | $R_{22}$ | $R_{23}$ | $R_{24}$ | $XR_4$ |
|---|---|---|---|---|---|---|
| 5.219 | $Q_{13}$ | H | — | — | H | ![O-C6H4-OC4H9] |
| 5.220 | $Q_{13}$ | NHCOOt-$C_4H_9$ | — | — | $CH_3$ | ![O-C6H4(2-COO-c-C5H9)] |
| 5.221 | $Q_{13}$ | $CH_3$ | — | — | $CH_3$ | ![O-C6H4(2-C3H7)] |
| 5.222 | $Q_{13}$ | $C_6H_5$ | — | — | $CH_3$ | ![S-3-pyridyl] |
| 5.223 | $Q_{13}$ | H | — | — | $CH_3$ | ![O-2,5-difluorophenyl] |
| 5.224 | $Q_{13}$ | H | — | — | 2-Thienyl | ![O-C6H4(2-CH3)] |
| 5.225 | $Q_{13}$ | $CH_3$ | — | — | $CON(CH_3)_2$ | ![O-C6H4(2-SO2-C2H5)] |
| 5.226 | $Q_{13}$ | $CH_3$ | — | — | $CH_2OC_2H_5$ | ![O-C6H4(4-COOH via CH2CH2)] |

TABLE 5-continued
Compounds of the formula VIa
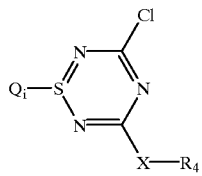
(VIa)
| Comp. No. | $Q_i$ | $R_{21}$ | $R_{22}$ | $R_{23}$ | $R_{24}$ | $XR_4$ |
|---|---|---|---|---|---|---|
| 5.227 | $Q_{13}$ | H | — | — | $CH(OC_2H_5)_2$ | |
| 5.228 | $Q_{13}$ | H | — | — | | |
| 5.229 | $Q_{13}$ | | — | — | $CH_3$ | |
| 5.230 | $Q_{13}$ | $C_6H_5$ | — | — | 2-Furyl | |
| 5.231 | $Q_{13}$ | | — | — | 4-Cl—$C_6H_4$ | |
| 5.232 | $Q_{13}$ | $C_6H_5$ | — | — | 2,4-Dichlorophenyl | |
| 5.233 | $Q_{13}$ | $CH_3$ | — | — | | |

TABLE 5-continued

Compounds of the formula VIa

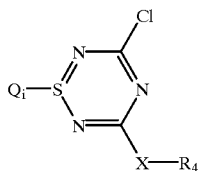

(VIa)

| Comp. No. | $Q_i$ | $R_{21}$ | $R_{22}$ | $R_{23}$ | $R_{24}$ | $XR_4$ |
|---|---|---|---|---|---|---|
| 5.234 | $Q_{13}$ | $(CH_2)_5Cl$ | — | — | $CH_2OCH_3$ | 2,6-dichlorophenoxy |
| 5.235 | $Q_{13}$ | $N(CH_3)C_6H_5$ | — | — | $t\text{-}C_4H_9$ | $OCH(CF_3)_2$ |
| 5.236 | $Q_{13}$ | 1-methyl-2-methylpyrrolidinyl | — | — | $CH_3$ | 2,3,5,6-tetrafluorophenoxy |
| 5.237 | $Q_{13}$ | $CH_3$ | — | — | 1-methyl-2-methylpyrrolidinyl | 3-($SC_5H_{11}$)phenoxy |
| 5.238 | $Q_{13}$ | $CH_3$ | — | — | $CF_3$ | $OCH_2C_7F_{15}$ |
| 5.239 | $Q_{16}$ | $OC_2H_5$ | — | $CH_3$ | — | 2-ethylphenoxy |
| 5.240 | $Q_{16}$ | $OH$ | — | $i\text{-}C_3H_7$ | — | 2,5-difluorophenoxy |
| 5.241 | $Q_{16}$ | $OCH_3$ | — | $t\text{-}C_4H_9$ | — | pentafluorophenoxy |
| 5.242 | $Q_{17}$ | — | H | H | — | $S\text{-}i\text{-}C_3H_7$ |
| 5.243 | $Q_{17}$ | — | H | $CH_3$ | — | $OCH(CF_3)_2$ |
| 5.244 | $Q_{17}$ | — | H | $C_6H_5$ | — | $OCH_2C_6F_5$ |
| 5.245 | $Q_{17}$ | — | H | CN | — | $OC_6H_5$ |

TABLE 5-continued
Compounds of the formula VIa
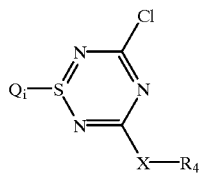
(VIa)
| Comp. No. | $Q_i$ | $R_{21}$ | $R_{22}$ | $R_{23}$ | $R_{24}$ | $XR_4$ |
|---|---|---|---|---|---|---|
| 5.246 | $Q_{17}$ | — | —CH=CH—CH=CH— | | — | |
| 5.247 | $Q_{17}$ | — | —CF=CH—CH=CH— | | — | benzodioxole-O- |
| 5.248 | $Q_{17}$ | — | —CH=CH—CH=CF— | | — | 1-naphthyloxy |
| 5.249 | $Q_{17}$ | — | —CH=CH—CCl=CH— | | — | 2-cyanophenoxy |
| 5.250 | $Q_{17}$ | — | —CH=CH—CH=CH— | | — | pentafluorophenoxy |
| 5.251 | $Q_{17}$ | — | Si(CH$_3$)$_3$ | H | — | OCH$_2$C$_3$F$_7$ |
| 5.252 | $Q_{17}$ | — | CH$_3$ | H | — | 2,4,6-trichlorophenoxy |
| 5.253 | $Q_{17}$ | — | C$_6$H$_5$ | H | — | propargyl 4-oxybenzoate |

TABLE 5-continued
Compounds of the formula VIa
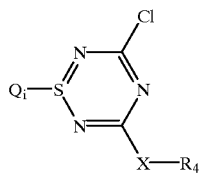
(VIa)
| Comp. No. | $Q_i$ | $R_{21}$ | $R_{22}$ | $R_{23}$ | $R_{24}$ | $XR_4$ |
|---|---|---|---|---|---|---|
| 5.254 | $Q_{17}$ | — | $Si(CH_3)_3$ | $CH_2OCH_3$ | — | pentafluorophenoxy |
| 5.255 | $Q_{18}$ | $CH_2C_6H_5$ | H | — | — | pentafluorophenoxy |
| 5.256 | $Q_{18}$ | H | NHCOO-t-$C_4H_9$ | — | — | 2,3,5,6-tetrafluorophenoxy |
| 5.257 | $Q_{18}$ | $C_6H_5$ | NHCO-t-$C_4H_9$ | — | — | 2-propargyloxyphenoxy (O-C$_6$H$_4$-CH$_2$C≡CH) |
| 5.258 | $Q_{18}$ | $C_6H_5$ | $CONHN(CH_3)_2$ | — | — | 4-nitrophenoxy |
| 5.259 | $Q_{18}$ | —CH=CH—CH=CH— | | — | — | 3-nitrophenoxy |
| 5.260 | $Q_{18}$ | H | H | — | — | pentafluorophenoxy |

TABLE 5-continued
Compounds of the formula VIa
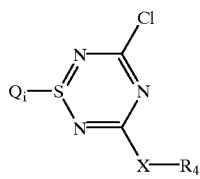
(VIa)
| Comp. No. | $Q_i$ | $R_{21}$ | $R_{22}$ | $R_{23}$ | $R_{24}$ | $XR_4$ |
|---|---|---|---|---|---|---|
| 5.261 | $Q_{18}$ | H | $CH_3$ | — | — | 2,5-difluorophenoxy |
| 5.262 | $Q_{18}$ | $NH_2$ | H | — | — | pentafluorophenoxy |
| 5.263 | $Q_{18}$ | $NH_2$ | $CH_3$ | — | — | 3-(N(C$_2$H$_5$)$_2$)phenoxy |
| 5.264 | $Q_{18}$ | $CON(C_2H_5)_2$ | H | — | — | 2,5-difluorophenoxy |
| 5.265 | $Q_{18}$ | $NHCOOC_2H_5$ | H | — | — | 2,4-bis(CF$_3$)phenoxy |
| 5.266 | $Q_{18}$ | $NHCOC_6H_5$ | H | — | — | pentafluorophenoxy |
| 5.267 | $Q_{18}$ | $C_6H_5$ | $SCH_3$ | — | — | 2-naphthyloxy |

TABLE 5-continued

Compounds of the formula VIa

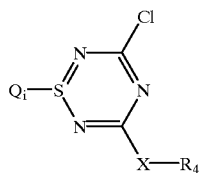

(VIa)

| Comp. No. | $Q_i$ | $R_{21}$ | $R_{22}$ | $R_{23}$ | $R_{24}$ | $XR_4$ |
|---|---|---|---|---|---|---|
| 5.268 | $Q_{18}$ | 2-methyl-1,3-dioxolan-2-yl (CH₃) | CH₃ | — | — | 2,5-difluorophenoxy |
| 5.269 | $Q_{18}$ | 4-Tolyl | SCH₃ | — | — | 2-fluoro-6-methylpyridin-3-yloxy |
| 5.270 | $Q_{18}$ | 4-carboxyphenyl | H | — | — | 5-chloro-3-fluoropyridin-2-yloxy |
| 5.271 | $Q_{18}$ | H | O-n-C₄H₉ | — | — | 1-methyl-5-trifluoromethyl-pyrazol-3-yloxy |
| 5.272 | $Q_{18}$ | —CH₂—(CH₂)₃—CH₂— | | — | — | 4-isopropylthiazol-2-yloxy |
| 5.273 | $Q_{18}$ | H | O-i-C₃H₇ | — | — | 2-ethylphenoxy |
| 5.274 | $Q_{18}$ | —CH₂—(CH₂)₄—CH₂— | | — | — | 2,6-dimethylpyridin-4-yloxy |

TABLE 5-continued
Compounds of the formula VIa
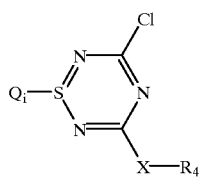
(VIa)
| Comp. No. | $Q_i$ | $R_{21}$ | $R_{22}$ | $R_{23}$ | $R_{24}$ | $XR_4$ |
|---|---|---|---|---|---|---|
| 5.275 | $Q_{18}$ | $CH_3$ | 4-Tolyl | — | — | 2,5-difluorophenoxy |
| 5.276 | $Q_{18}$ | H | 2-Tolyl | — | — | 2-thienylthio |
| 5.277 | $Q_{18}$ | H | $CBr_3$ | — | — | $OCH_2CH(CF_3)_2$ |
| 5.278 | $Q_{18}$ | 4-Cl—$C_6H_4$ | H | — | — | 2-naphthyloxy |
| 5.279 | $Q_{18}$ | —CH=CH—S— | | — | — | pentafluorophenoxy |
| 5.280 | $Q_{18}$ | $CH(OC_2H_5)_2$ | $CH_3$ | — | — | 2,5-difluorophenoxy |
| 5.281 | $Q_{18}$ | 4-Cl—$C_6H_4$ | $CON(CH_3)_2$ | — | — | 2-naphthyloxy |
| 5.282 | $Q_{18}$ | —S—CH=CH— | | — | — | 2-methylphenoxy |

TABLE 5-continued
Compounds of the formula VIa
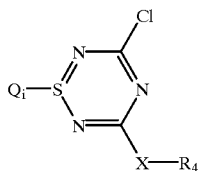
(VIa)
| Comp. No. | $Q_i$ | $R_{21}$ | $R_{22}$ | $R_{23}$ | $R_{24}$ | $XR_4$ |
|---|---|---|---|---|---|---|
| 5.283 | $Q_{18}$ | H | 4-Cl—$C_6H_4$ | — | — | 2,3,5,6-tetrafluorophenoxy |
| 5.284 | $Q_{20}$ | — | $CH_3$ | — | $CH_3$ | 4-($CF_3$)phenoxy |
| 5.285 | $Q_{20}$ | — | NHCOO-t-$C_4H_9$ | — | H | 2-Cl-5-$CH_3$-phenoxy |
| 5.286 | $Q_{20}$ | — | NHCOO-t-$C_4H_9$ | — | $CH_3$ | 3-($i$-$C_3H_7$)-5-$CH_3$-phenoxy |
| 5.287 | $Q_{20}$ | — | $i$-$C_4H_9$ | — | H | 3,5-bis($CF_3$)phenoxy |
| 5.288 | $Q_{20}$ | — | $i$-$C_3H_7$ | — | $CH_3$ | 2,5-difluorophenoxy |
| 5.289 | $Q_{20}$ | — | $C_2H_5$ | — | $CH_3$ | pentafluorophenoxy |

TABLE 5-continued

Compounds of the formula VIa

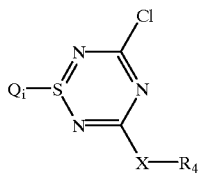

(VIa)

| Comp. No. | $Q_i$ | $R_{21}$ | $R_{22}$ | $R_{23}$ | $R_{24}$ | $XR_4$ |
|---|---|---|---|---|---|---|
| 5.290 | $Q_{20}$ | — | $NH_2$ | — | (4-F-2,5-dimethylphenyl) | (4-hydroxymethyl-phenyl with COOH) |
| 5.291 | $Q_{20}$ | — | $NH_2$ | — | $4\text{-Cl}—C_6H_4$ | (3-oxo-1,3-dihydro-isobenzofuran-1-yl, 7-oxy) |
| 5.292 | $Q_{20}$ | — | $CH_3$ | — | $t\text{-}C_4H_9$ | (2,5-difluorophenoxy) |
| 5.293 | $Q_{20}$ | — | $s\text{-}C_4H_9$ | — | H | (pentafluorophenoxy) |
| 5.294 | $Q_{20}$ | — | $i\text{-}C_4H_9$ | — | $CH_3$ | $O\text{-}i\text{-}C_3H_7$ |
| 5.295 | $Q_{20}$ | — | $Si(CH_3)_3$ | — | H | (2-methoxyphenoxy) |
| 5.296 | $Q_{20}$ | — | $n\text{-}C_3H_7$ | — | H | $O\text{-}c\text{-}C_6H_{11}$ |
| 5.297 | $Q_{20}$ | — | $CH_3$ | — | $CH_3$ | (pentafluorophenoxy) |

TABLE 5-continued

Compounds of the formula VIa

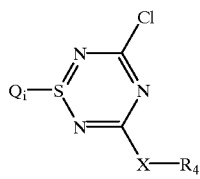

(VIa)

| Comp. No. | $Q_i$ | $R_{21}$ | $R_{22}$ | $R_{23}$ | $R_{24}$ | $XR_4$ |
|---|---|---|---|---|---|---|
| 5.298 | $Q_{20}$ | — | $OC_2H_5$ | — | H | 2,6-dichlorophenoxy |
| 5.299 | $Q_{20}$ | — | $CH_3$ | — | CN | 2-(methoxycarbonyl)phenoxy |
| 5.300 | $Q_{20}$ | — | H | — | $C_6H_5$ | 2,3,6-trifluorophenoxy |
| 5.301 | $Q_{20}$ | — | $CH_3$ | — | $CH_2$-thiomorpholin-4-yl | 2,5-difluorophenoxy |
| 5.302 | $Q_{20}$ | — | $CH_3$ | — | 3-Pyridyl | 4-tert-butylphenoxy |
| 5.303 | $Q_{20}$ | — | $C_6H_5$ | — | $CONHCH_3$ | 4-methylphenylthio |
| 5.304 | $Q_{20}$ | — | $NHCOCH_3$ | — | $CF_3$ | 2-(trifluoromethyl)phenoxy |
| 5.305 | $Q_{21}$ | H | — | — | $C_6H_5$ | 3-chloro-4-fluorophenoxy |

TABLE 5-continued
Compounds of the formula VIa
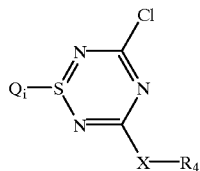
(VIa)
| Comp. No. | $Q_i$ | $R_{21}$ | $R_{22}$ | $R_{23}$ | $R_{24}$ | $XR_4$ |
|---|---|---|---|---|---|---|
| 5.306 | $Q_{21}$ | $CH_2OCH_3$ | — | — | $C_6H_5$ | 2,5-difluorophenoxy |
| 5.307 | $Q_{21}$ | $CH_3$ | — | — | 4-Cl—$C_6H_4$ | 2-chloro-5-methylphenoxy |
| 5.308 | $Q_{30}$ | — | — | $C_6H_5$ | — | 4-phenylphenoxy |
| 5.309 | $Q_{30}$ | — | — | $n$-$C_4H_9$ | — | 2-nitrophenoxy |
| 5.310 | $Q_{33}$ | $C_6H_5$ | — | — | — | 2-(methoxycarbonyl)phenoxy |
| 5.311 | $Q_{33}$ | $t$-$C_4H_9$ | — | — | — | 3-nitrophenoxy |
| 5.312 | $Q_{33}$ | $i$-$C_3H_7$ | — | — | — | 2,4,6-trichlorophenoxy |
| 5.313 | $Q_{33}$ | $C_2H_5$ | — | — | — | 2-hexylphenoxy |

TABLE 5-continued
Compounds of the formula VIa
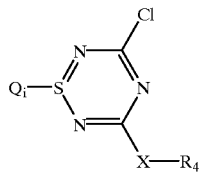
(VIa)
| Comp. No. | $Q_i$ | $R_{21}$ | $R_{22}$ | $R_{23}$ | $R_{24}$ | $XR_4$ |
|---|---|---|---|---|---|---|
| 5.314 | $Q_{33}$ | $CH_3$ | — | — | — | ![4-(3-pyridyl)phenoxy] |
| 5.315 | $Q_{33}$ | $OCH_3$ | — | — | — | ![pentafluorophenoxy] |
| 5.316 | $Q_{33}$ | $O$-n-$C_4H_9$ | — | — | — | ![2-(trifluoromethyl)phenoxy] |
| 5.317 | $Q_{33}$ | $N(C_2H_5)_2$ | — | — | — | ![pentafluorophenoxy] |
| 5.318 | $Q_{33}$ | $SCH_3$ | — | — | — | ![1-naphthyloxy] |
| 5.319 | $Q_{33}$ | $S$-c-$C_6H_{11}$ | — | — | — | ![pentafluorophenoxy] |
| 5.320 | $Q_{33}$ | ![4-chlorophenylthio] | — | — | — | $OC_8H_{17}$ |

TABLE 5-continued
Compounds of the formula VIa
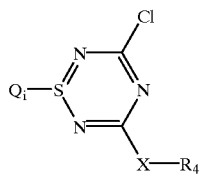
(VIa)
| Comp. No. | $Q_i$ | $R_{21}$ | $R_{22}$ | $R_{23}$ | $R_{24}$ | $XR_4$ |
|---|---|---|---|---|---|---|
| 5.321 | $Q_{33}$ | 4-chlorophenyl-SO$_2$-CH$_3$ | — | — | — | 2,6-dichlorophenoxy |
| 5.322 | $Q_{33}$ | 3-(trifluoromethyl)-methoxyphenyl | — | — | — | 2,3,5,6-tetrafluorophenoxy |
| 5.323 | $Q_{39}$ | — | — | — | $CH_3$ | benzo[1,3]dioxol-5-yloxy |
| 5.324 | $Q_{39}$ | — | — | — | $C_6H_5$ | 3,3,5,5-tetramethylcyclohexyloxy |
| 5.325 | $Q_{39}$ | — | — | — | $n\text{-}C_4H_9$ | 3-ethylphenoxy |
| 5.326 | $Q_{20}$ | — | Cl | — | H | pentafluorophenoxy |

TABLE 5-continued
Compounds of the formula VIa
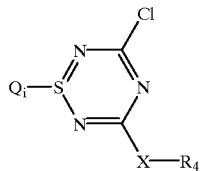
(VIa)
| Comp. No. | $Q_i$ | $R_{21}$ | $R_{22}$ | $R_{23}$ | $R_{24}$ | $XR_4$ |
|---|---|---|---|---|---|---|
| 5.327 | $Q_{20}$ | — | O—CH$_2$CF$_3$ | — | H | 3,5-dimethylphenoxy |
| 5.328 | $Q_{20}$ | — | —CN | — | H | 2,5-dimethylphenoxy |
| 5.329 | $Q_{20}$ | — | 3,5-dimethylphenoxy | — | H | pentafluorophenoxy |
| 5.330 | $Q_{20}$ | — | 2,5-difluorophenoxy | — | H | 2,5-difluorophenoxy |
| 5.331 | $Q_{20}$ | — | pentafluorophenoxy | — | H | pentafluorophenoxy |
| 5.332 | $Q_{20}$ | — | Cl | — | H | OCH$_2$CF$_3$ |
| 5.333 | $Q_{20}$ | — | OCH$_2$CF$_3$ | — | H | OCH$_2$CF$_3$ |
| 5.334 | $Q_{20}$ | — | Cl | — | H | 3-n-propylphenoxy |

TABLE 6

Compounds of the formula VIIIa

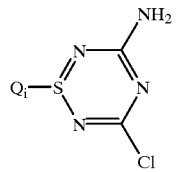

| Comp. No. | $Q_1$ | $R_{21}$ | $R_{22}$ | $R_{23}$ | $R_{24}$ |
|---|---|---|---|---|---|
| 6.001 | $Q_1$ | H | —CH=CH—CH=N— | | $CH_3$ |
| 6.002 | $Q_1$ | $CH_3$ | —C(Cl)=CH—CH=N— | | $COCH_3$ |
| 6.003 | $Q_1$ | —S—CH=CH— | | H | 4-$CH_3$—$C_6H_4$ |
| 6.004 | $Q_1$ | —CH=CH—S— | | H | 4-$CH_3$—$C_6H_4$ |
| 6.005 | $Q_2$ | H | $CH_3$ | H | — |
| 6.006 | $Q_2$ | H | H | H | — |
| 6.007 | $Q_2$ | H | H | —CH=CHCH$_3$ | |
| 6.008 | $Q_2$ | H | —CH=CH—CH=CH— | | — |
| 6.009 | $Q_2$ | (2-methyl-4,4-dimethyl-oxazoline) | H | H | — |
| 6.010 | $Q_2$ | H | H | $SCH_3$ | — |
| 6.011 | $Q_2$ | H | H | $COOCH_3$ | — |
| 6.012 | $Q_2$ | H | H | —CH=CH$_2$ | — |
| 6.013 | $Q_2$ | H | H | $S(O)CH_3$ | — |
| 6.014 | $Q_2$ | H | H | $Si(CH_3)_3$ | — |
| 6.015 | $Q_2$ | H | —C(Cl)=CH—C(Cl)=CH— | | — |
| 6.016 | $Q_2$ | H | H | $COCH_3$ | — |
| 6.017 | $Q_2$ | H | H | $OCH_3$ | — |
| 6.018 | $Q_2$ | H | H | Cl | — |
| 6.019 | $Q_2$ | H | —C(OCH$_3$)=CH—CH=CH— | | — |
| 6.020 | $Q_2$ | $CH_3$ | (substituted diene group with $H_3C$, $CH_2$, O-i-$C_3H_7$) | | — |
| 6.021 | $Q_2$ | H | —C(CH$_3$)=CH—CH=CH— | | — |
| 6.022 | $Q_2$ | H | —CH=CH—CH=C(CH$_3$)— | | — |
| 6.023 | $Q_2$ | H | H | —C≡CH | — |
| 6.024 | $Q_2$ | OH | —CH=CH—CH=CH— | | — |
| 6.025 | $Q_2$ | $CH_3$ | —CH=C(CH$_3$)—C(CH$_3$)=CH— | | — |
| 6.026 | $Q_2$ | $CH_3$ | H | H | — |
| 6.027 | $Q_2$ | H | H | $C_2H_5$ | — |
| 6.028 | $Q_2$ | Cl | H | H | — |
| 6.029 | $Q_2$ | H | H | n-$C_6H_{13}$ | — |
| 6.030 | $Q_2$ | H | H | $CH_3$ | — |
| 6.031 | $Q_2$ | —CH$_2$—C(CH$_3$)=C(CH$_3$)—CH$_2$— | | H | — |
| 6.032 | $Q_2$ | H | H | Sn(n-$C_4H_9$)$_3$ | — |
| 6.033 | $Q_2$ | H | H | $SO_2CH_3$ | — |
| 6.034 | $Q_2$ | H | H | t-$C_4H_9$ | — |
| 6.035 | $Q_2$ | H | H | n-$C_4H_9$ | — |
| 6.036 | $Q_2$ | H | H | I | — |
| 6.037 | $Q_2$ | H | H | B(OH)$_2$ | — |
| 6.038 | $Q_2$ | H | —CO—NH—CH=CH— | | — |
| 6.039 | $Q_2$ | H | $CH_3$ | F | — |
| 6.040 | $Q_2$ | $OCH_3$ | H | H | — |
| 6.041 | $Q_3$ | H | H | — | $CH_3$ |
| 6.042 | $Q_3$ | H | H | — | CON($C_2H_5$)$_2$ |
| 6.043 | $Q_3$ | H | H | — | Cl |
| 6.044 | $Q_3$ | H | H | — | $OCH_3$ |
| 6.045 | $Q_3$ | H | Si(CH$_3$)$_3$ | — | CON($C_2H_5$)$_2$ |
| 6.046 | $Q_3$ | H | H | — | $CH_2OCH_3$ |

TABLE 6-continued

Compounds of the formula VIIIa

| Comp. No. | $Q_1$ | $R_{21}$ | $R_{22}$ | $R_{23}$ | $R_{24}$ |
|---|---|---|---|---|---|
| 6.047 | $Q_3$ | —CH=CH—CH=CH— | | — | $CON(C_2H_5)_2$ |
| 6.048 | $Q_3$ | CONH-t-$C_4H_9$ | $CH_3$ | — | $CH_3$ |
| 6.049 | $Q_2$ | H | H | 2-methyl-4,4-dimethyl-oxazoline | — |
| 6.050 | $Q_3$ | —CH=CH—CH=CH— | | — | $CH_2N(CH_3)_2$ |
| 6.051 | $Q_3$ | —CH=CH—CH=CH— | | — | $H_2C$-pyrrolidinyl |
| 6.052 | $Q_4$ | H | H | H | — |
| 6.053 | $Q_4$ | H | —CH=CH—CH=CH— | | — |
| 6.054 | $Q_4$ | H | $CH_3$ | F | — |
| 6.055 | $Q_4$ | $OCH_3$ | H | H | — |
| 6.056 | $Q_4$ | H | H | $t-C_4H_9$ | — |
| 6.057 | $Q_4$ | H | H | $n-C_4H_9$ | — |
| 6.058 | $Q_4$ | H | H | $CH_3$ | — |
| 6.059 | $Q_4$ | $CH_3$ | H | H | — |
| 6.060 | $Q_4$ | H | H | $C_2H_5$ | — |
| 6.061 | $Q_4$ | Cl | H | H | — |
| 6.062 | $Q_4$ | H | H | $n-C_6H_{13}$ | — |
| 6.063 | $Q_4$ | H | H | $Si(CH_3)_3$ | — |
| 6.064 | $Q_4$ | H | H | $Sn(n-C_4H_9)_3$ | — |
| 6.065 | $Q_4$ | H | H | I | — |
| 6.066 | $Q_4$ | H | H | $B(OH)_2$ | — |
| 6.067 | $Q_4$ | H | H | 2-thienyl | — |
| 6.068 | $Q_4$ | H | $CH_3$ | H | — |
| 6.069 | $Q_4$ | —$CH_2$—$CH_2$—$CH_2$—$C(OCH_3)_2$— | | $SCH_3$ | — |
| 6.070 | $Q_4$ | H | =HC–N(4-tolyl)–CH= | — | — |
| 6.071 | $Q_4$ | H | H | $COCH_3$ | — |
| 6.072 | $Q_4$ | neopentyl-$OC_3H_7$ group | | $SCH_3$ | — |

TABLE 6-continued

Compounds of the formula VIIIa

[Structure: 1,2,4,6-thiatriazine ring with $Q_1$–S, $NH_2$ and Cl substituents]

| Comp. No. | $Q_1$ | $R_{21}$ | $R_{22}$ | $R_{23}$ | $R_{24}$ |
|---|---|---|---|---|---|
| 6.073 | $Q_4$ | H | \\ S–C(=CH–)–CH₂–SCH₂CCH (bridged $R_{22}$–$R_{23}$) | | — |
| 6.074 | $Q_4$ | $CH_3$ | —C($CH_3$)=C($SCH_3$)—S— | | — |
| 6.075 | $Q_4$ | H | —N=C(OCH₃)–N=C(OCH₃)— (bridged) | | — |
| 6.076 | $Q_4$ | H | H | $COOCH_3$ | — |
| 6.077 | $Q_4$ | $CH_3$ | $H_3C$–CH=C(S–)(COOC₄H₉)– (bridged) | | — |
| 6.078 | $Q_4$ | H | —S—CH=CH— | | — |
| 6.079 | $Q_4$ | H | H | —C≡CH | — |
| 6.080 | $Q_4$ | $CH_3$ | —CH=N—CH=N— | | — |
| 6.081 | $Q_4$ | $CH_3$ | —N=CH—N=CH— | | — |
| 6.082 | $Q_4$ | $CH_3$ | —N=CH–N=C–N(CH₂CH₂OH)(CH₃)— (bridged) | | — |
| 6.083 | $Q_4$ | H | H | —CH=CH₂ | — |
| 6.084 | $Q_4$ | H | \\S–C(=CH–)–C(=O)O-t-C₄H₉ (bridged $R_{22}$–$R_{23}$) | | — |
| 6.085 | $Q_4$ | H | —N=C(CF₃)–N=C(OCH₃)— (bridged) | | — |
| 6.086 | $Q_4$ | H | H | —CH=CHCH₃ | — |

TABLE 6-continued

Compounds of the formula VIIIa

[Structure: 1,2,4,6-thiatriazine ring with $Q_1$–S, NH$_2$ and Cl substituents]

| Comp. No. | $Q_1$ | $R_{21}$ | $R_{22}$ | $R_{23}$ | $R_{24}$ |
|---|---|---|---|---|---|
| 6.087 | $Q_4$ | H | [structure: =C(OCH$_3$)–C(CH$_3$)(OCH$_3$)–C(=O)NHC$_2$H$_5$] | | — |
| 6.088 | $Q_4$ | $C_6H_5$ | [structure: i-C$_3$H$_7$–S–C(CH$_3$)=N–N(CH$_3$)–CH=NH (or similar formamidine)] | | — |
| 6.089 | $Q_4$ | —CH$_2$—C(CH$_3$)$_2$—CH=C(OCH$_3$)— | | SCH$_3$ | — |
| 6.090 | $Q_4$ | CH$_3$ | —C(CH$_3$)=CH—S— | | — |
| 6.091 | $Q_4$ | CH$_3$ | [structure: pyrrolidin-1-yl–C(CH$_3$)=N–N(CH$_3$)–CH=NH] | | — |
| 6.092 | $Q_4$ | H | H | SO$_2$CH$_3$ | — |
| 6.093 | $Q_4$ | CH$_3$ | [structure: CH$_3$SC(CH$_3$)=N–N(CH$_3$)–CH=NH formamidine] | | — |
| 6.094 | $Q_4$ | Si(CH$_3$)$_3$ | H | H | — |
| 6.095 | $Q_4$ | CH$_3$ | [structure: H$_3$CS–C(CH$_3$)=N–N(CH$_3$)–CH=NH] | | — |
| 6.096 | $Q_4$ | CH$_3$ | [structure: (H$_3$C)(H$_3$C)C=C(SCH$_3$)–C(=O)–N(morpholino)] | | — |
| 6.097 | $Q_4$ | H | [structure: H$_5$C$_2$–C(OH)(CH$_3$)–CH$_2$–S–CH$_3$] | | — |

TABLE 6-continued

Compounds of the formula VIIIa

[Structure: 1,2,4,6-thiatriazine ring with $Q_1$—S, $NH_2$ group, and Cl substituent]

| Comp. No. | $Q_1$ | $R_{21}$ | $R_{22}$ | $R_{23}$ | $R_{24}$ |
|---|---|---|---|---|---|
| 6.098 | $Q_4$ | $CH_3$ | [structure: $H_3C$, $CH_3$, C=C, S, $COOCH_3$] | | — |
| 6.099 | $Q_4$ | $CH_3$ | [structure: $CH_3$N=CH—N=C($CH_3$)—S—C$_6$H$_4$Cl] | | — |
| 6.100 | $Q_4$ | H | [structure: HC=C($CH_3$)(S$CH_3$), COOH] | | — |
| 6.101 | $Q_4$ | H | [structure: HC=C(C$_2$H$_5$)(S$CH_3$), $CH_2OC_3H_7$] | | — |
| 6.102 | $Q_4$ | H | [structure: $H_3C$—N($CH_3$)—C(=CH$CH_3$)—C(=O)$CH_3$] | | — |
| 6.103 | $Q_4$ | H | [structure: $H_3C$, $CH_3$, C=C, S$CH_3$, C(=O)-morpholine] | | — |
| 6.104 | $Q_4$ | H | [structure: ClC(CH$_3$)=C(SCH$_3$)—C(=O)NHCH$_2$C$_6$H$_5$] | | — |
| 6.105 | $Q_4$ | H | H | $S(O)CH_3$ | — |
| 6.106 | $Q_4$ | H | —CH=CH—CH=C(CH$_3$)— | | — |
| 6.107 | $Q_4$ | —(CH$_2$)$_2$NH$_2$ | —CH=CH— | | — |

TABLE 6-continued

Compounds of the formula VIIIa

| Comp. No. | $Q_1$ | $R_{21}$ | $R_{22}$ | $R_{23}$ | $R_{24}$ |
|---|---|---|---|---|---|
| 6.108 | $Q_4$ | —(CH$_2$)$_2$N(CH$_3$)$_2$ | C(OCH$_3$)=CH—<br>—C(OCH$_3$)=CH—<br>CH=CH— | | — |
| 6.109 | $Q_4$ | —(CH$_2$)$_2$OH | —CH=CH—CH=CH— | | — |
| 6.110 | $Q_4$ | —CH$_2$SH | —CH=CH—CH=CH— | | — |
| 6.111 | $Q_4$ | CH$_3$ | —CH=CF—CH=CH— | | — |
| 6.112 | $Q_4$ | H | CH$_2$C(=O)OC$_2$H$_5$ group with CH=CH | | — |
| 6.113 | $Q_4$ | OCH$_3$ | HC=CH-C(OC$_2$H$_5$)=CH group | | — |
| 6.114 | $Q_4$ | H | H | SCH$_3$ | — |
| 6.115 | $Q_4$ | H | H | Sn(CH$_3$)$_3$ | — |
| 6.116 | $Q_4$ | CH$_2$CON(CH$_3$)$_2$ | —CH=CH—<br>C(OCH$_3$)=CH— | | — |
| 6.117 | $Q_4$ | H | CH$_3$ | H | — |
| 6.118 | $Q_4$ | H | H | OCH$_3$ | — |
| 6.119 | $Q_4$ | H | —C(OH)=CH—CH=CH— | | — |
| 6.120 | $Q_4$ | CH$_3$ | —CH=CH—CH=CH— | | — |
| 6.121 | $Q_4$ | CH$_2$CO$_2$H | —CH=CH—CH=CH— | | — |
| 6.122 | $Q_4$ | CH$_2$CO$_2$C$_2$H$_5$ | —CH=C(Cl)—CH=CH— | | — |
| 6.123 | $Q_4$ | CH$_3$ | —CH=C(Cl)—CH=CH— | | — |
| 6.124 | $Q_4$ | H | —CH=C(CH$_3$)—CH=CH— | | — |
| 6.125 | $Q_4$ | H | H | Cl | — |
| 6.126 | $Q_4$ | CH$_3$ | —CH=C(CH$_3$)—CH=CH— | | — |
| 6.127 | $Q_4$ | H | Si(CH$_3$)$_3$ | H | — |
| 6.128 | $Q_4$ | CH$_2$N(CH$_3$)$_2$ | —CH=CH—CH=CH— | | — |
| 6.129 | $Q_4$ | CH$_2$-morpholinyl | —CH=CH—CH=CH— | | — |
| 6.130 | $Q_5$ | H | H | — | C$_6$H$_5$ |
| 6.131 | $Q_5$ | H | CH$_3$ | — | C$_6$H$_5$ |
| 6.132 | $Q_5$ | H | CH$_3$ | — | CH$_2$OCH$_3$ |
| 6.133 | $Q_5$ | C$_6$H$_5$ | CH$_3$ | — | CON(CH$_3$)$_2$ |
| 6.134 | $Q_5$ | —CH=CH—CH=CH— | | — | CH$_3$ |
| 6.135 | $Q_5$ | H | C$_2$H$_5$ | — | 2-Cl—C$_6$H$_4$ |
| 6.136 | $Q_5$ | H | C(OCH$_3$)$_3$ | — | i-C$_3$H$_7$ |
| 6.137 | $Q_5$ | H | CH$_3$ | — | t-C$_4$H$_9$ |
| 6.138 | $Q_5$ | H | SCH$_3$ | — | t-C$_4$H$_9$ |
| 6.139 | $Q_5$ | H | 2-Thiazolyl | — | CH$_3$ |
| 6.140 | $Q_5$ | H$_2$C—O—CH(CH$_3$) group | | — | CH$_3$ |
| 6.141 | $Q_5$ | H | 3-Cl—C$_6$H$_4$ | — | CH$_2$OC$_2$H$_5$ |
| 6.142 | $Q_5$ | H | CF$_3$ | — | CH$_3$ |

TABLE 6-continued

Compounds of the formula VIIIa

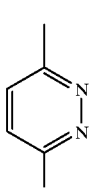

| Comp. No. | $Q_1$ | $R_{21}$ | $R_{22}$ | $R_{23}$ | $R_{24}$ |
|---|---|---|---|---|---|
| 6.143 | $Q_7$ | H | — | $C_6H_5$ | H |
| 6.144 | $Q_7$ | $C_6H_5$ | — | $CH_3$ | H |
| 6.145 | $Q_7$ | H | — | $CH_3$ | $C_6H_5$ |
| 6.146 | $Q_7$ | $CH_3$ | — | 3-methyl-6-methyl-pyridazinyl | $CH_3$ |
| 6.147 | $Q_7$ | H | — | $CH_3$ | $OCH_3$ |
| 6.148 | $Q_7$ | $OCH_3$ | — | $CH_3$ | H |
| 6.149 | $Q_7$ | $N(CH_3)_2$ | — | $t\text{-}C_4H_9$ | $CH_3$ |
| 6.150 | $Q_7$ | $CH_3$ | — | $t\text{-}C_4H_9$ | $N(CH_3)_2$ |
| 6.151 | $Q_8$ | — | H | H | $CH_2C_6H_5$ |
| 6.152 | $Q_8$ | — | H | H | $SO_2C_6H_5$ |
| 6.153 | $Q_8$ | — | H | H | $C_6H_5$ |
| 6.154 | $Q_8$ | — | H | H | $CH_3$ |
| 6.155 | $Q_8$ | — | —CH=CH—CH=CH— | | $n\text{-}C_3H_7$ |
| 6.156 | $Q_8$ | — | Cl | Cl | $CH_2C_6H_5$ |
| 6.157 | $Q_8$ | — | H | H | $CONHCH_3$ |
| 6.158 | $Q_8$ | — | —CH=CH—CH=CH— | | $CO\text{-}t\text{-}C_4H_9$ |
| 6.159 | $Q_8$ | — | —CH=CH—CH=CH— | | $CONHt\text{-}C_4H_9$ |
| 6.160 | $Q_8$ | — | $CH_3$ | $CH_3$ | $CH_2OCH_3$ |
| 6.161 | $Q_8$ | — | —$CH_2$—$CH_2$—$CH_2$—$CH_2$— | | $CON(CH_3)_2$ |
| 6.162 | $Q_8$ | — | H | H | $SO_2(CH3)_2$ |
| 6.163 | $Q_{11}$ | — | —CH=C($CH_3$)—CH=CH— | | — |
| 6.164 | $Q_{11}$ | — | —CH=CH—C($CH_3$)=CH— | | — |
| 6.165 | $Q_{11}$ | — | —CH=CH—C(Cl)=CH— | | — |
| 6.166 | $Q_{11}$ | — | —CH=CH—CH=CH— | | — |
| 6.167 | $Q_{11}$ | — | $C_6H_5$ | H | — |
| 6.168 | $Q_{11}$ | — | $2\text{-Cl}\text{-}C_6H_4$ | H | — |
| 6.169 | $Q_{11}$ | — | $4\text{-F}\text{-}C_6H_4$ | H | — |
| 6.170 | $Q_{11}$ | — | 2-Furyl | H | — |
| 6.171 | $Q_{11}$ | — | 4-Tolyl | H | — |
| 6.172 | $Q_{11}$ | — | 4-Anisyl | H | — |
| 6.173 | $Q_{11}$ | — | 2-Thienyl | H | — |
| 6.174 | $Q_{11}$ | — | 3,3-dimethyl-5-methyl-indolin-2-one | H | — |
| 6.175 | $Q_{11}$ | — | $4\text{-CF}_3\text{-}C_6H_4$ | $CO_2C_2H_5$ | — |
| 6.176 | $Q_{11}$ | — | $C_6H_5$ | $CO_2C_2H_5$ | — |
| 6.177 | $Q_{11}$ | — | 2,4-Dichlorophenyl | $CO_2C_2H_5$ | — |
| 6.178 | $Q_{11}$ | — | $3\text{-Cl}\text{-}C_6H_4$ | $CO_2C_2H_5$ | — |
| 6.179 | $Q_{11}$ | — | $t\text{-}C_4H_9$ | $CO_2C_2H_5$ | — |
| 6.180 | $Q_{13}$ | H | — | — | H |
| 6.181 | $Q_{13}$ | $CH_3$ | — | — | $CH_3$ |

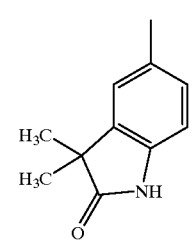

TABLE 6-continued

Compounds of the formula VIIIa

| Comp. No. | $Q_1$ | $R_{21}$ | $R_{22}$ | $R_{23}$ | $R_{24}$ |
|---|---|---|---|---|---|
| 6.182 | $Q_{13}$ | $C_6H_5$ | — | — | $CH_3$ |
| 6.183 | $Q_{13}$ | H | — | — | $CH_3$ |
| 6.184 | $Q_{13}$ | H | — | — | 2-Thienyl |
| 6.185 | $Q_{13}$ | $CH_3$ | — | — | $CON(CH_3)_2$ |
| 6.186 | $Q_{13}$ | $CH_3$ | — | — | $CH_2OC_2H_5$ |
| 6.187 | $Q_{13}$ | H | — | — | $CH(OC_2H_5)_2$ |
| 6.188 | $Q_{13}$ | H | — | — | $HC(C_3H_7)-OCH_3$ |
| 6.189 | $Q_{13}$ | 2,6-dimethyl-methoxyphenyl | — | — | $CH_3$ |
| 6.190 | $Q_{13}$ | $C_6H_5$ | — | — | 2-Furyl |
| 6.191 | $Q_{13}$ | $(CH_3)_2C(CON(CH_3)_2)$ | — | — | 4-Cl—$C_6H_4$ |
| 6.192 | $Q_{13}$ | $C_6H_5$ | — | — | 2,4-Dichloro-phenyl |
| 6.193 | $Q_{13}$ | $CH_3$ | — | — | methyl-quinuclidinyl |
| 6.194 | $Q_{13}$ | $(CH_2)_5Cl$ | — | — | $CH_2OCH_3$ |
| 6.195 | $Q_{13}$ | $N(CH_3)C_6H_5$ | — | — | $t\text{-}C_4H_9$ |
| 6.196 | $Q_{13}$ | 1-methyl-2-pyrrolidinyl | — | — | $CH_3$ |
| 6.197 | $Q_{13}$ | $CH_3$ | — | — | 1-methyl-2-pyrrolidinyl |
| 6.198 | $Q_{13}$ | $CH_3$ | — | — | $CF_3$ |
| 6.199 | $Q_{16}$ | $OC_2H_5$ | — | $CH_3$ | — |
| 6.200 | $Q_{16}$ | OH | — | $i\text{-}C_3H_7$ | — |
| 6.201 | $Q_{16}$ | $OCH_3$ | — | $t\text{-}C_4H_9$ | — |

TABLE 6-continued

Compounds of the formula VIIIa

| Comp. No. | $Q_1$ | $R_{21}$ | $R_{22}$ | $R_{23}$ | $R_{24}$ |
|---|---|---|---|---|---|
| 6.202 | $Q_{17}$ | — | H | H | — |
| 6.203 | $Q_{17}$ | — | H | $CH_3$ | — |
| 6.204 | $Q_{17}$ | — | H | $C_6H_5$ | — |
| 6.205 | $Q_{17}$ | — | H | CN | — |
| 6.206 | $Q_{17}$ | — | —CH=CH—CH=CH— | | — |
| 6.207 | $Q_{17}$ | — | —CF=CH—CH=CH— | | — |
| 6.208 | $Q_{17}$ | — | —CH=CH—CH=CF— | | — |
| 6.209 | $Q_{17}$ | — | —CH=CH—CCl=CH— | | — |
| 6.210 | $Q_{17}$ | — | —CH=CH—CH=CH— | | — |
| 6.211 | $Q_{17}$ | — | $Si(CH_3)_3$ | H | — |
| 6.212 | $Q_{17}$ | — | $CH_3$ | H | — |
| 6.213 | $Q_{17}$ | — | $C_6H_5$ | H | — |
| 6.214 | $Q_{17}$ | — | $Si(CH_3)_3$ | $CH_2OCH_3$ | — |
| 6.215 | $Q_{18}$ | $CH_2C_6H_5$ | H | — | — |
| 6.216 | $Q_{18}$ | —CH=CH—CH=CH— | | — | — |
| 6.217 | $Q_{18}$ | H | H | — | — |
| 6.218 | $Q_{18}$ | H | $CH_3$ | — | — |
| 6.219 | $Q_{18}$ | $CON(C_2H_5)_2$ | H | — | — |
| 6.220 | $Q_{18}$ | $NHCOOC_2H_5$ | H | — | — |
| 6.221 | $Q_{18}$ | $NHCOC_6H_5$ | H | — | — |
| 6.222 | $Q_{18}$ | $C_6H_5$ | $SCH_3$ | — | — |
| 6.223 | $Q_{18}$ | 2-methyl-1,3-dioxolan-2-yl | $CH_3$ | — | — |
| 6.224 | $Q_{18}$ | 4-Tolyl | $SCH_3$ | — | — |
| 6.225 | $Q_{18}$ | 4-(COOH)-phenyl | H | — | — |
| 6.226 | $Q_{18}$ | H | O-n-$C_4H_9$ | — | — |
| 6.227 | $Q_{18}$ | —CH2—$(CH_2)_3$—$CH_2$— | | — | — |
| 6.228 | $Q_{18}$ | H | O-i-$C_3H_7$ | — | — |
| 6.229 | $Q_{18}$ | —$CH_2$—$(CH_2)_4$—$CH_2$— | | — | — |
| 6.230 | $Q_{18}$ | $CH_3$ | 4-Tolyl | — | — |
| 6.231 | $Q_{18}$ | H | 2-Tolyl | — | — |
| 6.232 | $Q_{18}$ | H | $CBr_3$ | — | — |
| 6.233 | $Q_{18}$ | 4-Cl—$C_6H_4$ | H | — | — |
| 6.234 | $Q_{18}$ | —CH=CH—S— | | — | — |
| 6.235 | $Q_{18}$ | $CH(OC_2H_5)_2$ | $CH_3$ | — | — |
| 6.236 | $Q_{18}$ | 4-Cl—$C_6H_4$ | $CON(CH_3)_2$ | — | — |
| 6.237 | $Q_{18}$ | —S—CH=CH— | | — | — |
| 6.238 | $Q_{18}$ | H | 4-Cl—$C_6H_4$ | — | — |
| 6.239 | $Q_{20}$ | — | $CH_3$ | — | $CH_3$ |
| 6.240 | $Q_{20}$ | — | i-$C_4H_9$ | — | H |
| 6.241 | $Q_{20}$ | — | i-$C_3H_7$ | — | $CH_3$ |
| 6.242 | $Q_{20}$ | — | $C_2H_5$ | — | $CH_3$ |
| 6.243 | $Q_{20}$ | — | $CH_3$ | — | t-$C_4H_9$ |
| 6.244 | $Q_{20}$ | — | s-$C_4H_9$ | — | H |
| 6.245 | $Q_{20}$ | — | i-$C_4H_9$ | — | $CH_3$ |
| 6.246 | $Q_{20}$ | — | $Si(CH_3)_3$ | — | H |
| 6.247 | $Q_{20}$ | — | n-$C_3H_7$ | — | H |
| 6.248 | $Q_{20}$ | — | $CH_3$ | — | $CH_3$ |

TABLE 6-continued
Compounds of the formula VIIIa
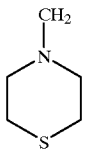
| Comp. No. | $Q_1$ | $R_{21}$ | $R_{22}$ | $R_{23}$ | $R_{24}$ |
|---|---|---|---|---|---|
| 6.249 | $Q_{20}$ | — | $OC_2H_5$ | — | H |
| 6.250 | $Q_{20}$ | — | $CH_3$ | — | CN |
| 6.251 | $Q_{20}$ | — | H | — | $C_6H_5$ |
| 6.252 | $Q_{20}$ | — | $CH_3$ | — |  |
| 6.253 | $Q_{20}$ | — | $CH_3$ | — | 3-Pyridyl |
| 6.254 | $Q_{20}$ | — | $C_6H_5$ | — | $CONHCH_3$ |
| 6.255 | $Q_{20}$ | — | $NHCOCH_3$ | — | $CF_3$ |
| 6.256 | $Q_{21}$ | H | — | — | $C_6H_5$ |
| 6.257 | $Q_{21}$ | $CH_2OCH_3$ | — | — | $C_6H_5$ |
| 6.258 | $Q_{21}$ | $CH_3$ | — | — | 4-Cl—$C_6H_4$ |
| 6.259 | $Q_{30}$ | — | — | $C_6H_5$ | — |
| 6.260 | $Q_{30}$ | — | — | n-$C_4H_9$ | — |
| 6.261 | $Q_{33}$ | $C_6H_5$ | — | — | — |
| 6.262 | $Q_{33}$ | t-$C_4H_9$ | — | — | — |
| 6.263 | $Q_{33}$ | i-$C_3H_7$ | — | — | — |
| 6.264 | $Q_{33}$ | $C_2H_5$ | — | — | — |
| 6.265 | $Q_{33}$ | $CH_3$ | — | — | — |
| 6.266 | $Q_{33}$ | $OCH_3$ | — | — | — |
| 6.267 | $Q_{33}$ | O-n-$C_4H_9$ | — | — | — |
| 6.268 | $Q_{33}$ | $N(C_2H_5)_2$ | — | — | — |
| 6.269 | $Q_{33}$ | $SCH_3$ | — | — | — |
| 6.270 | $Q_{33}$ | S-c-$C_6H_{11}$ | — | — | — |
| 6.271 | $Q_{33}$ | 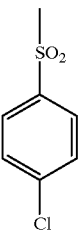 | — | — | — |
| 6.272 | $Q_{33}$ | 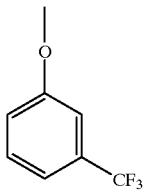 | — | — | — |
| 6.273 | $Q_{33}$ |  | — | — | — |

TABLE 6-continued

Compounds of the formula VIIIa

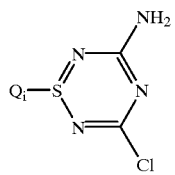

| Comp. No. | $Q_1$ | $R_{21}$ | $R_{22}$ | $R_{23}$ | $R_{24}$ |
|---|---|---|---|---|---|
| 6.274 | $Q_{39}$ | — | — | — | $CH_3$ |
| 6.275 | $Q_{39}$ | — | — | — | $C_6H_5$ |
| 6.276 | $Q_{39}$ | — | — | — | $n\text{-}C_4H_9$ |
| 6.277 | $Q_{20}$ | — | Cl | — | H |
| 6.278 | $Q_{20}$ | — | $O\text{—}CH_2CF_3$ | — | H |
| 6.279 | $Q_{20}$ | — | —CN | — | H |
| 6.280 | $Q_{20}$ | — | 3,5-dimethylphenoxy | — | H |
| 6.281 | $Q_{20}$ | — | 2,5-difluorophenoxy | — | H |
| 6.282 | $Q_{20}$ | — | pentafluorophenoxy | — | H |
| 6.283 | $Q_2$ | $CH_3$ | $-CH=C(CH_3)-C(N\text{-pyrrolyl})=CH-$ | — | — |

TABLE 7

Physical data of the compounds from Tables 2–6:

| Compound No. | Physical data Melting point |
|---|---|
| 2.006 | 195–196° C. |
| 2.008 | 185° C. (decomposition) |
| 2.009 | 195–196° C. |
| 2.025 | 232° C. (decomposition) |
| 2.027 | 202–203° C. (decomposition) |
| 2.039 | 166–167° C. (decomposition) |
| 2.046 | 230° C. (decomposition) |
| 2.058 | 125–127° C. |
| 2.061 | 179–180° C. |
| 2.062 | 213° C. (decomposition) |
| 2.066 | 144–147° C. |
| 2.067 | 174–176° C. |
| 2.068 | 203° C. (decomposition) |

TABLE 7-continued

Physical data of the compounds from Tables 2–6:

| Compound No. | Physical data Melting point |
|---|---|
| 2.076 | 214–215° C. (decomposition) |
| 2.077 | 192–200° C. (decomposition) |
| 2.082 | 165–167° C. (decomposition) |
| 2.084 | 208–209° C. |
| 2.088 | 206–207° C. (decomposition) |
| 2.090 | 250° C. (decomposition) |
| 2.094 | 231° C. (decomposition) |
| 2.097 | 258° C. (decomposition) |
| 2.105 | 167–168° C. |
| 2.110 | 162–163° C. |
| 2.113 | 165–166° C. |
| 2.120 | 146–147° C. |
| 2.126 | 189–190° C. |
| 2.141 | 230° C. (decomposition) |
| 2.147 | 159–160° C. (decomposition) |
| 2.149 | 210° C. (decomposition) |
| 2.157 | 169–170° C. |
| 2.163 | 170–173° C. |
| 2.192 | 205–206° C. |
| 2.250 | 211° C. (decomposition) |
| 2.260 | 198–199° C. (decomposition) |
| 2.297 | 188–189° C. (decomposition) |
| 2.326 | 157–158° C. (decomposition) |
| 2.327 | 193–194° C. |
| 4.008 | 128° C. |
| 4.009 | not determined |
| 4.049 | not determined |
| 4.052 | 100–103° C. (decomposition) |
| 4.053 | 122–123° C. (decomposition) |
| 4.056 | 124–129° C. (decomposition) |
| 4.057 | oil |
| 4.058 | 86–87° C. |
| 4.059 | 118–120° C. (decomposition) |
| 4.060 | 61–62° C. |
| 4.062 | oil |
| 4.067 | 118–119° C. (decomposition) |
| 4.068 | 86° C. |
| 4.118 | 105–106° C. (decomposition) |
| 4.125 | 112–112° C. (decomposition) |
| 4.206 | 211° C. (decomposition) |
| 4.217 | solid |
| 6.006 | 215° C. (decomposition) |
| 6.008 | 216° C. (decomposition) |
| 6.009 | 158° C. (decomposition) |
| 6.049 | 157° C. (decomposition) |
| 6.052 | 217° C. (decomposition) |
| 6.053 | 224° C. (decomposition) |
| 6.056 | 167–168° C. (decomposition) |
| 6.057 | 146–148° C. (decomposition) |
| 6.058 | 222° C. (decomposition) |
| 6.059 | 200° C. (decomposition) |
| 6.060 | 172° C. (decomposition) |
| 6.062 | 85° C. (decomposition) |
| 6.067 | 235° C. (decomposition) |
| 6.068 | 192° C. (decomposition) |
| 6.118 | 185° C. (decomposition) |
| 6.125 | 223° C. (decomposition) |
| 6.206 | 232° C. (decomposition) |
| 6.217 | solid |
| 6.239 | 181° C. (decomposition) |
| 2.200 | 179–180° C. |
| 2.337 | 223–224° C. |
| 2.102 | 158–160° C. |
| 2.332 | 205–207° C. |
| 2.333 | 172–173° C. |
| 2.328 | 159–160° C. |
| 4.154 | 115° C. (decomposition) |
| 4.162 | >200° C. |
| 4.083 | crystalline |
| 4.283 | 156° C. (decomposition) |
| 4.277 | 112–120° C. (decomposition) |
| 5.326 | crystalline |
| 6.154 | 164° C. |
| 6.162 | 168–170° C. |
| 6.083 | crystalline |
| 6.283 | crystalline |
| 6.278 | 211° C. (decomposition) |

Formulation Examples for Active Substances of the Formula I (%=per cent by weight)

| F1. Emulsion concentrate | a) | b) | c) | d) |
|---|---|---|---|---|
| Active substance according to Tables 2–3 | 5% | 10% | 25% | 50% |
| Ca dodecylbenzenesulfonate | 6% | 8% | 6% | 8% |
| Castor oil polyglycol ether (36 mol of EO) | 4% | — | 4% | 4% |
| Octylphenol polyglycol ether (7–8 mol of EO) | — | 4% | — | 2% |
| Cyclohexanone | — | — | 10% | 20% |
| Aromatic hydrocarbon mixture $C_9$–$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| Active substance according to Tables 2–3 | 5% | 10% | 50% | 90% |
| 1-Methoxy-3-(3-methoxy-propoxy)-propane | — | 20% | 20% | — |
| Polyethylene glycol MW 400 | 20% | 10% | — | — |
| N-Methyl-2-pyrrolidone | — | — | 30% | 10% |
| Aromatic hydrocarbon mixture $C_9$–$C_{12}$ | 75% | 60% | — | — |

The solutions are suitable for use in the form of tiny drops.

| F3. Wettable powders | a) | b) | c) | d) |
|---|---|---|---|---|
| Active substance according to Tables 2–3 | 5% | 25% | 50% | 80% |
| Sodium ligninsulfonate | 4% | — | 3% | — |
| Sodium lauryl sulfate | 2% | 3% | — | 4% |
| Sodium diisobutyl-naphthalene-sulfonate | — | 6% | 5% | 6% |
| Octylphenol polyglycol ether (7–8 mol of EO) | — | 1% | 2% | — |
| Highly disperse silicic acid | 1% | 3% | 5% | 10% |
| Kaolin | 88% | 62% | 35% | — |

The active substance is mixed thoroughly with the additives and the mixture is ground thoroughly in a suitable mill. Wettable powders which can be diluted with water to give suspensions of any desired concentration are obtained.

| F4. Coated granules | a) | b) | c) |
|---|---|---|---|
| Active substance according to Tables 2–3 | 0.1% | 5% | 15% |
| Highly disperse silicic acid | 0.9% | 2% | 2% |
| Inorganic carrier material (Ø 0.1–1 mm) for exampie $CaCO_3$ or $SiO_2$ | 99.0% | 93% | 83% |

The active substance is dissolved in methylene chloride, the solution is sprayed onto the carrier and the solvent is then evaporated off in vacuo.

| F5. Coated granules | a) | b) | c) |
|---|---|---|---|
| Active substance according to Tables 2–3 | 0.1% | 5% | 15% |
| Polyethylene glycol MW 200 | 1.0% | 2% | 3% |
| Highly disperse silicic acid | 0.9% | 1% | 2% |
| Inorganic carrier material (Ø 0.1–1 mm) for example $CaCO_3$ or $SiO_2$ | 98.0% | 92% | 80% |

The finely ground active substance is applied uniformly to the carrier material, which is moistened with polyethylene glycol, in a mixer. Dust-free coated granules are obtained in this manner.

| F6. Extruded granules | a) | b) | c) | d) |
|---|---|---|---|---|
| Active substance according to Tables 2–3 | 0.1% | 3% | 5% | 15% |
| Sodium ligninsulfonate | 1.5% | 2% | 3% | 4% |
| Carboxymethylcellulose | 1.4% | 2% | 2% | 2% |
| Kaolin | 97.0% | 93% | 90% | 79% |

The active substance is mixed with the additives and the mixture is ground and moistened with water. This mixture is extruded and then dried in a stream of air.

| F7. Dusts | a) | b) | c) |
|---|---|---|---|
| Active substance according to Tables 2–3 | 0.1% | 1% | 5% |
| Talc | 39.9% | 49% | 35% |
| Kaolin | 60.0% | 50% | 60% |

Ready-to-use dusts are obtained by mixing the active substance with the carriers and grinding the mixture on a suitable mill.

| F8. Suspension Concentrates | a) | b) | c) | d) |
|---|---|---|---|---|
| Active substance according to Tables 2–3 | 3% | 10% | 25% | 50% |
| Ethylene glycol | 5% | 5% | 5% | 5% |
| Nonylphenol polyglycol ether (15 mol of EO) | — | 1% | 2% | |
| Sodium ligninsulfonate | 3% | 3% | 4% | 5% |
| Carboxymethylcellulose | 1% | 1% | 1% | 1% |
| 37% strength aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active substance is mixed intimately with the additives. A suspension concentrate from which suspensions of any desired concentration can be prepared by dilution with water is thus obtained.

Biological Examples

EXAMPLE B1

Herbicidal Action Before the Emergence of the Plants (Pre-emergence Action)

Monocotyledon and dicotyledon test plants are sown in standard soil in plastic pots. Immediately after sowing, the test substances are sprayed on as an aqueous suspension (prepared from a 25% wettable powder (Example F3, b)) or as an emulsion (prepared from a 25% emulsion concentrate (Example F1, c)) in a dosage corresponding to 2 kg of AS/ha (500 l of water/ha). The test plants are then grown under optimum conditions in a greenhouse. After a test duration of 3 weeks, the test is evaluated by a nine-level scale of ratings (1=complete damage, 9=no action). Rating values of 1 to 4 (in particular 1 to 3) mean a good to very good herbicidal action. In this test, the compounds of the formula I show a good herbicidal action. Examples of the herbicidal action of the compounds of the formula I are given in Table B1:

TABLE B1

Pre-emergence action of the compounds of the formula I:

| Compound No. | Avena | Setaria | Sinapis | Stellaria |
|---|---|---|---|---|
| 2.025 | 2 | 1 | 1 | 1 |
| 2.039 | 2 | 1 | 1 | 1 |
| 2.061 | 2 | 1 | 1 | 1 |
| 2.066 | 3 | 1 | 1 | 1 |
| 2.082 | 2 | 1 | 1 | 1 |
| 2.088 | 3 | 2 | 1 | 1 |
| 2.090 | 4 | 2 | 1 | 1 |
| 2.105 | 3 | 2 | 1 | i |
| 2.110 | 2 | 1 | 1 | 1 |
| 2.147 | 2 | 1 | i | 1 |
| 2.297 | 1 | 1 | 1 | 1 |

EXAMPLE B2

Post-emergence Herbicidal Action

Monocotyledon and dicotyledon test plants are grown in plastic pots with standard soil in a greenhouse and, in the 4- to 6-leaf stage, are sprayed with an aqueous suspension of the test substances of the formula I, prepared from a 25% wettable powder (Example F3, b)) or with an emulsion of the test substances of the formula I, prepared from a 25% emulsion concentrate (Example F1, c)), in a dosage corresponding to 2 kg of AS/ha (500 l of water/ha). The test plants are then grown further under optimum conditions in a greenhouse. After a test duration of about 18 days, the test is evaluated with a nine-level scale of ratings (1=complete damage, 9=no action). Rating values of 1 to 4 (in particular 1 to 3) mean a good to very good herbicidal action. In this test also, the compounds of the formula I show a potent herbicidal action. Examples of the herbicidal action of the compounds of the formula I are given in Table B2:

TABLE B2

Post-emergence action of the compounds of the formula I:

| Compound No. | Avena | Setaria | Sinapis | Stellaria |
|---|---|---|---|---|
| 2.025 | 1 | 4 | 2 | 3 |
| 2.039 | 2 | 4 | 2 | 4 |
| 2.061 | 1 | 4 | 2 | 2 |
| 2.066 | 1 | 6 | 1 | 3 |
| 2.082 | 2 | 4 | 3 | 2 |
| 2.088 | 2 | 5 | 2 | 3 |
| 2.090 | 1 | 6 | 1 | 2 |
| 2.105 | 1 | 3 | 1 | 2 |
| 2.110 | 1 | 2 | 2 | 1 |
| 2.147 | 1 | 3 | 1 | 2 |
| 2.297 | 1 | 2 | 1 | 2 |

What is claimed is:
1. A compound of the formula I

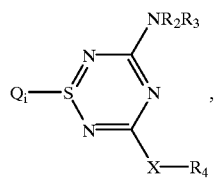

(I)

in which $Q_i$ is the group $Q_2$

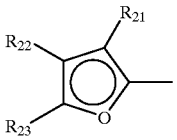

$Q_4$

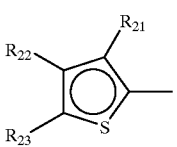

$Q_8$

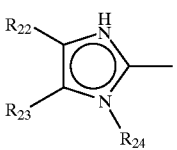

$Q_{17}$

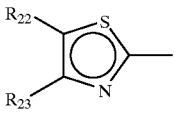

$Q_{18}$

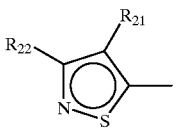  or $Q_{20}$

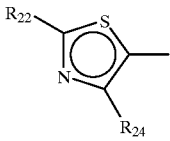

X is oxygen;

$R_2$ and $R_3$ are hydrogen;

$R_4$ is phenyl substituted by nitro, $C_1$–$C_{10}$-halogenalkyl, COOH, —$CH_2$—$CH_2$—COOH, $C_1$–$C_{10}$-alkoxy or halogen;

$R_{21}$, $R_{22}$, $R_{23}$ and $R_{24}$ independently of one another are hydrogen,

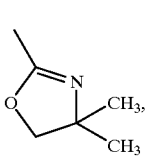 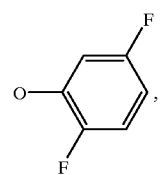

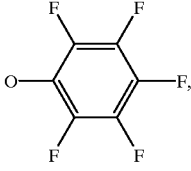 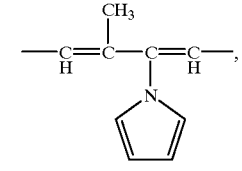

2-thienyl, $C_2$–$C_8$-alkenyl, halogen, $SO_2N(CH_3)_2$ or $C_1$–$C_{10}$-alkyl, which $C_1$–$C_{10}$-alkyl in turn can be substituted by OR$_5$, wherein R$_5$ is C$_1$–C$_6$-alkyl, or R$_{22}$ and R$_{23}$ together are —CH═CH—CH═CH—, or an agronomically tolerated salt/N-oxide/isomer/enantiomer of this compound.

2. A composition for use as a herbicide or plant growth inhibitor which comprises a herbicidally effective or plant growth inhibiting effective amount of a compound of the formula I according to claim 1 and an inert carrier.

3. The composition according to claim 2, which comprises between 0.1% and 95% of the compound of the formula I.

4. A method of controlling unwanted plant growth, which comprises applying an effective controlling amount of the compound of the formula I according to claim 1 or a composition comprising this compound to the plants, plant parts, seeds or their environment.

5. A method according to claim 4, wherein the compound is applied in an amount of between 0.001 and 4 kg per hectare.

6. A method of inhibiting plant growth, which comprises applying the compound of the formula I according to claim 1 or a composition comprising this compound to the plants, plant parts, seeds or their environment in a herbicidally effective amount.

* * * * *